(12) United States Patent
Ghods et al.

(10) Patent No.: US 12,265,063 B2
(45) Date of Patent: Apr. 1, 2025

(54) EMBEDDED SENSOR DEVICES AND METHODS

(71) Applicant: GIATEC SCIENTIFIC INC., Nepean (CA)

(72) Inventors: Pouria Ghods, Gloucester (CA); Rouhollah Alizadeh, Nepean (CA); Andrew Fahim, Ottawa (CA); Sarah De Carufel, Clarence Creek (CA); Mustafa Salehi, Nepean (CA)

(*) Notice: Subject to any disclaimer, the term of this patent is extended or adjusted under 35 U.S.C. 154(b) by 806 days.

(21) Appl. No.: 17/593,964

(22) PCT Filed: Apr. 3, 2020

(86) PCT No.: PCT/CA2020/050440
§ 371 (c)(1),
(2) Date: Sep. 29, 2021

(87) PCT Pub. No.: WO2020/198872
PCT Pub. Date: Oct. 8, 2020

(65) Prior Publication Data
US 2022/0107251 A1 Apr. 7, 2022

Related U.S. Application Data

(60) Provisional application No. 62/828,585, filed on Apr. 3, 2019.

(51) Int. Cl.
*G01N 3/62* (2006.01)
*G01N 3/06* (2006.01)
(Continued)

(52) U.S. Cl.
CPC ............... *G01N 3/066* (2013.01); *G01N 3/62* (2013.01); *G01N 33/383* (2013.01); *H04W 4/80* (2018.02)

(58) Field of Classification Search
CPC ........ G01N 3/066; G01N 3/62; G01N 33/383; H04W 4/80
See application file for complete search history.

(56) References Cited

U.S. PATENT DOCUMENTS

2002/0154029 A1  10/2002  Watters et al.
2004/0153270 A1   8/2004  Yamashita et al.
(Continued)

FOREIGN PATENT DOCUMENTS

CN   103852488 A   6/2014
EP      3293509 A1   3/2018

OTHER PUBLICATIONS

Perry, M. et al. "Wireless Concrete Strength Monitoring of Wind Turbine Foundations", Sensors, vol. 17, No. 12, Dec. 16, 2017.

*Primary Examiner* — Jamel E Williams
(74) *Attorney, Agent, or Firm* — Rosenberg, Klein & Lee

(57) ABSTRACT

Many construction materials are chemically active materials whose structural properties parameters, physical-mechanical properties, etc. need to be determined. By exploiting embedded wireless sensors within these materials from initial wet manufactured state to final solid capillary-porous material assessment of initial and subsequent properties can be established allowing determination of current and future performance of the construction material. Embedded sensors can also monitor lifetime properties to identify performance degradations in the construction material as well as other construction elements embedded within or around the construction material. Further, the data accumulated from initial manufacturing to extended lifetime allows for additional assessments and improvements with respect to selection of construction material mix for a particular project at a particular location and time, improving the assessment of proactive repair and/or remedial work, quality control monitoring, cost reduction etc.

12 Claims, 26 Drawing Sheets

(51) Int. Cl.
*G01N 33/38* (2006.01)
*H04W 4/80* (2018.01)

(56) References Cited

U.S. PATENT DOCUMENTS

| | | |
|---|---|---|
| 2007/0046479 A1 | 3/2007 | Hines |
| 2015/0335284 A1 | 11/2015 | Nuovo et al. |
| 2017/0000415 A1 | 1/2017 | Lapetina et al. |
| 2017/0284996 A1 | 10/2017 | Ghods et al. |
| 2022/0022748 A1* | 1/2022 | Al-Ali .................... A61B 5/021 |
| 2023/0028745 A1* | 1/2023 | Al-Ali .................. A61B 5/6824 |
| 2023/0384825 A1* | 11/2023 | Connor ................ G04G 17/083 |

* cited by examiner

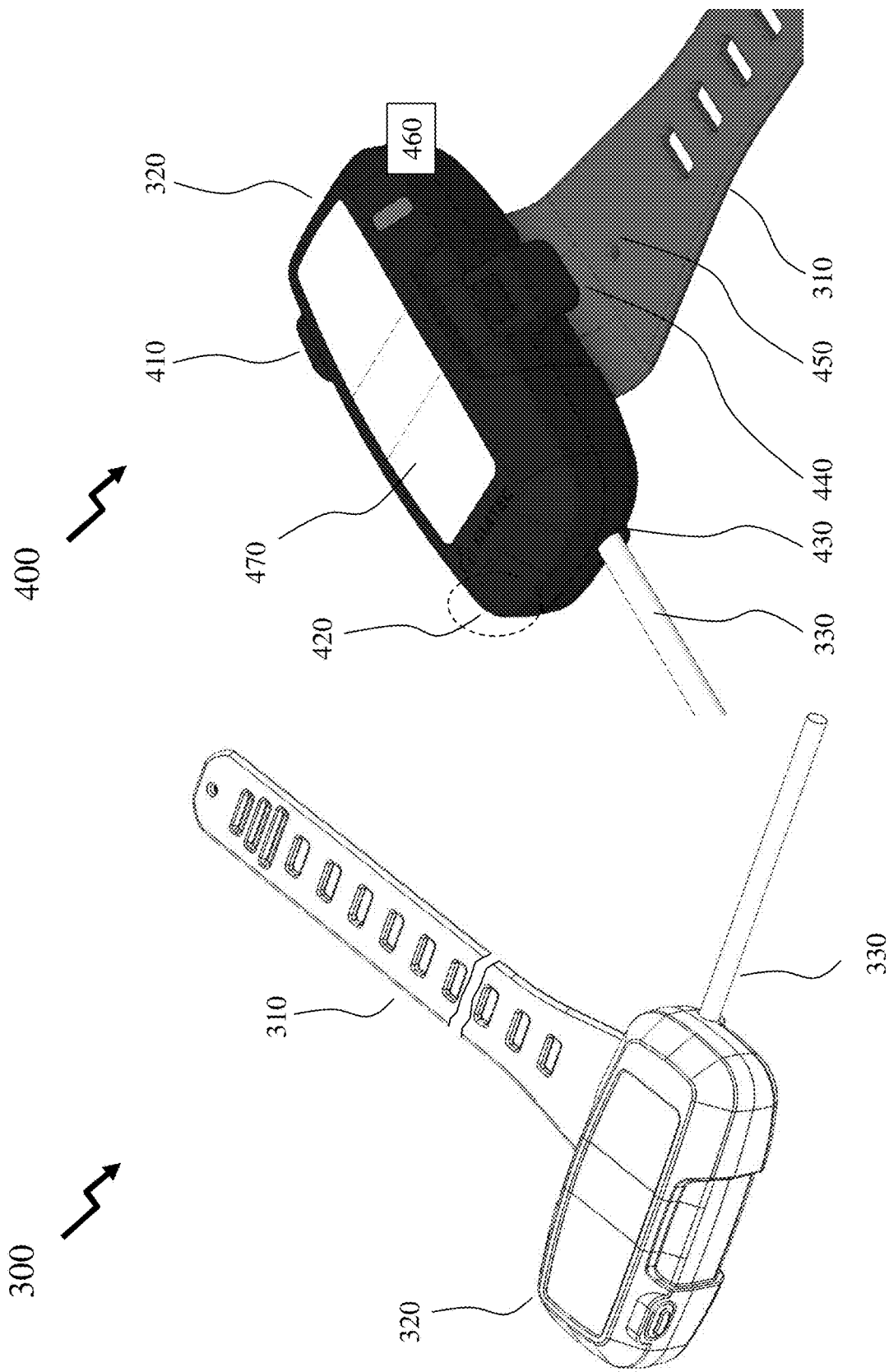

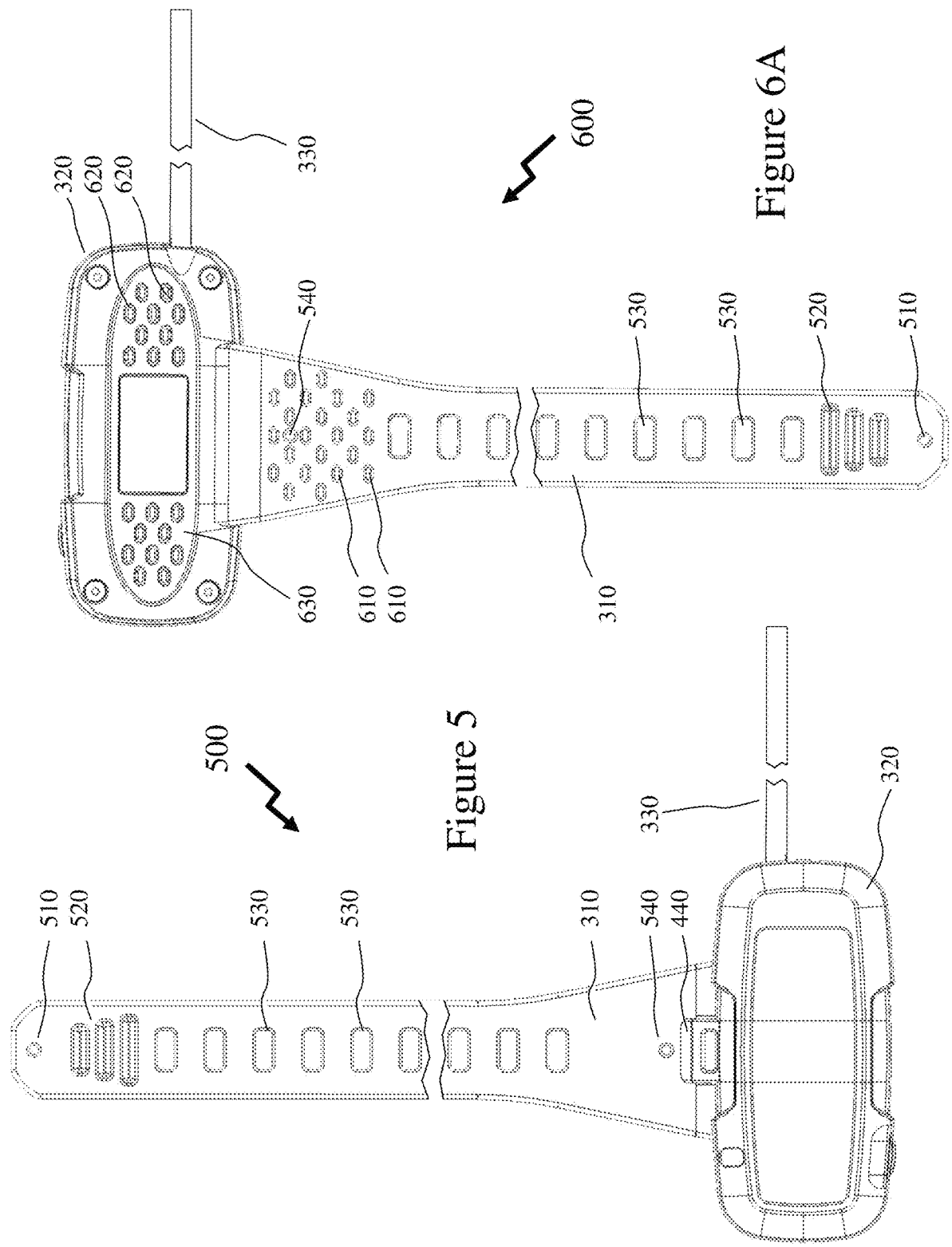

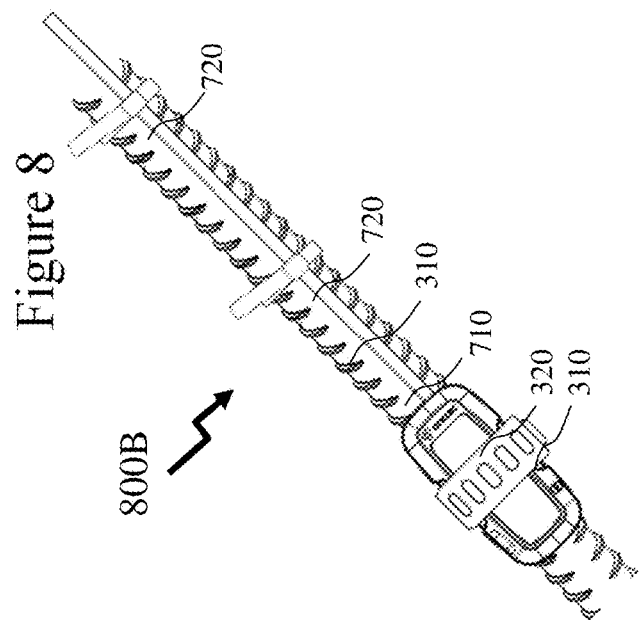
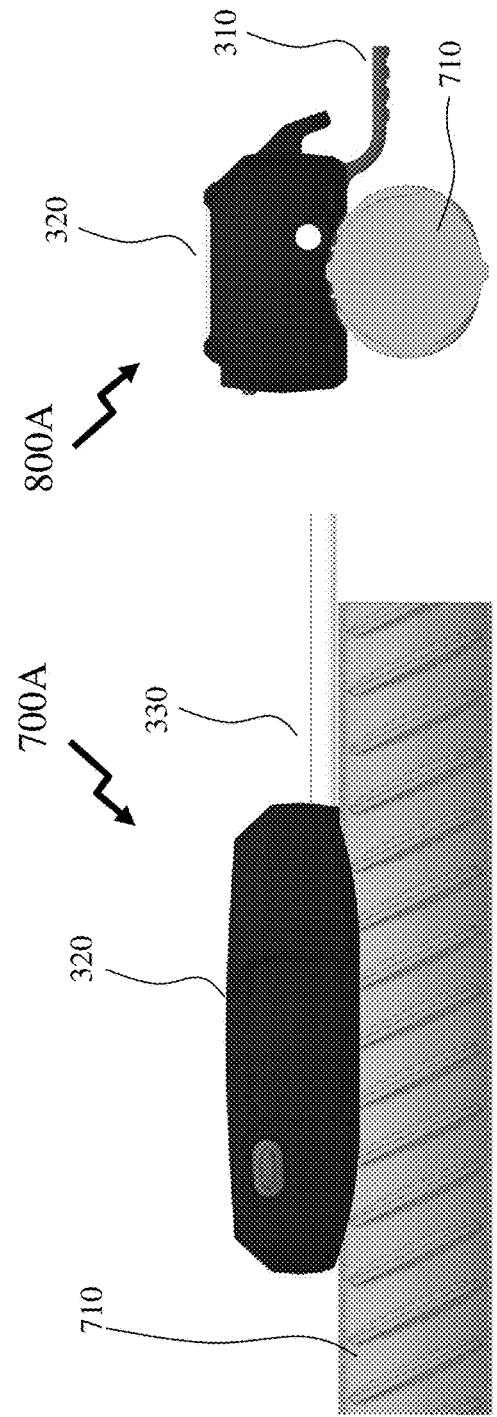
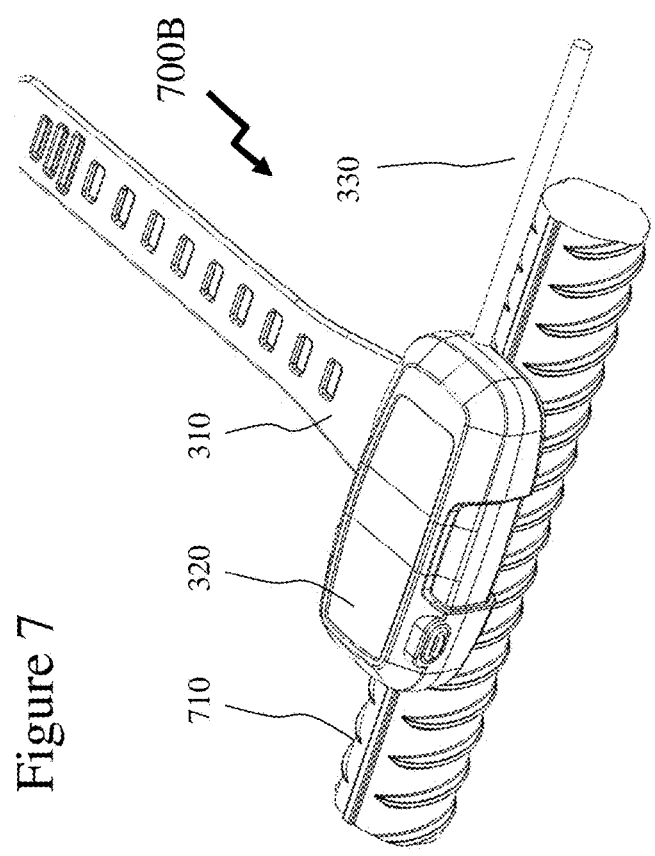
Figure 7
Figure 8

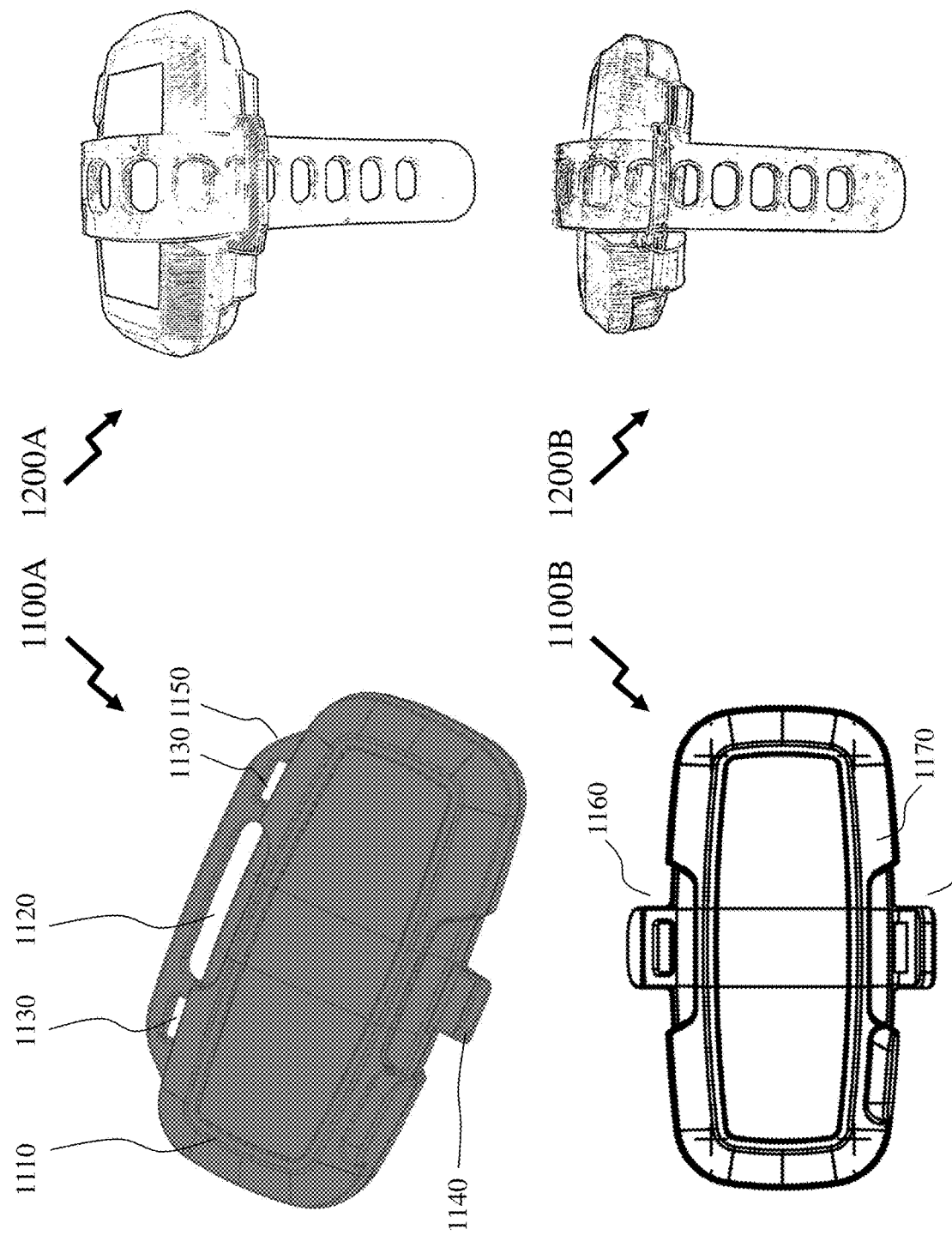

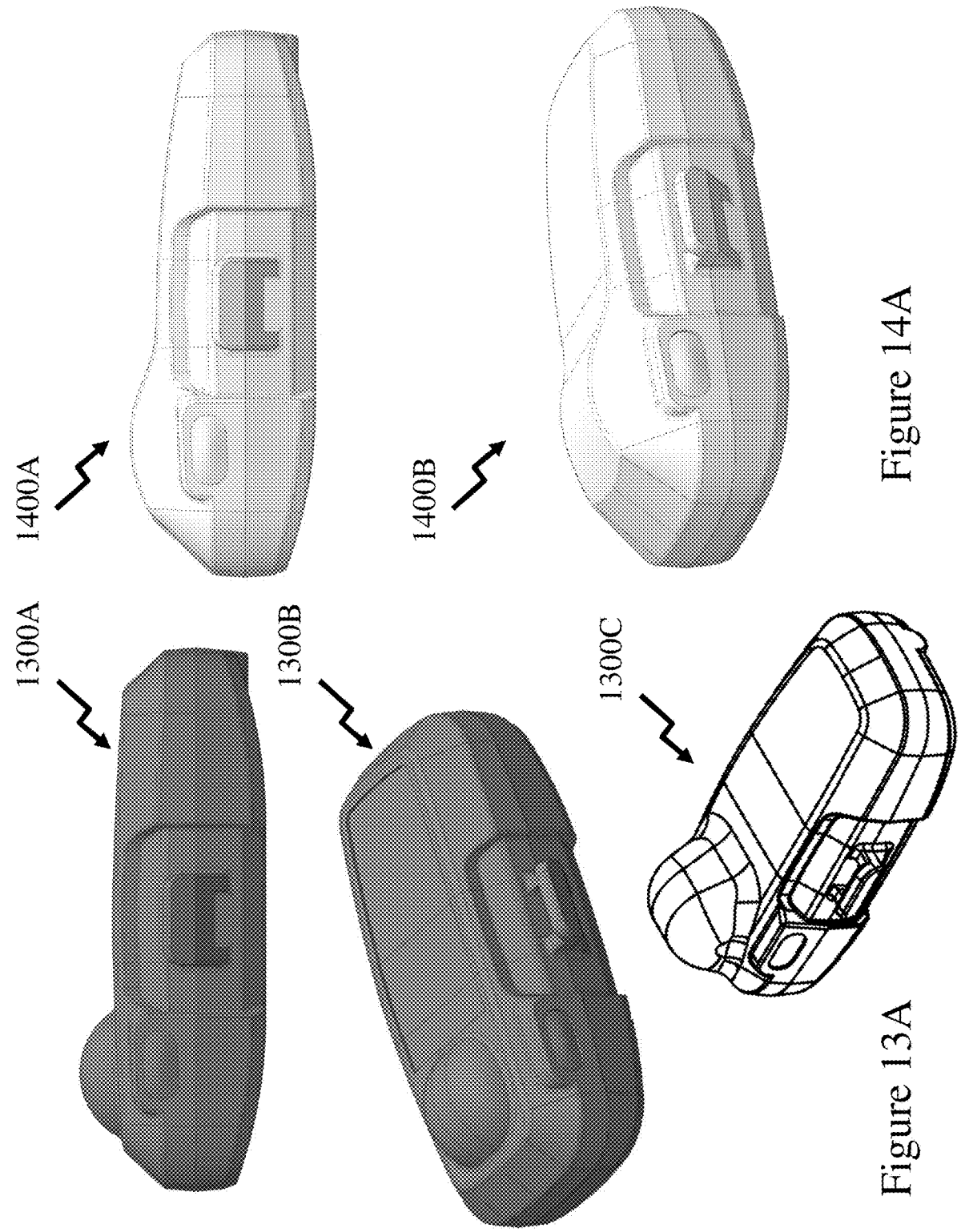

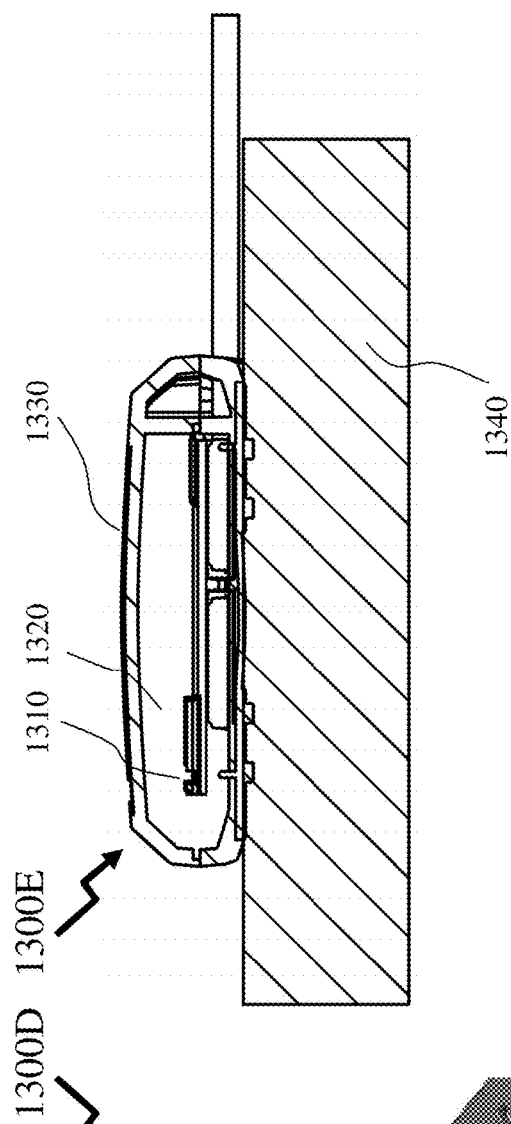
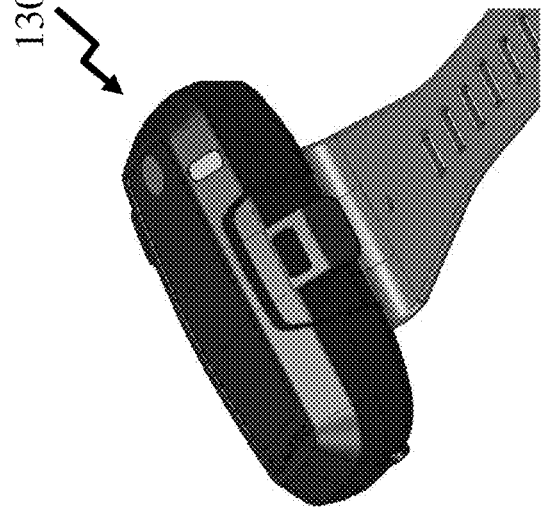
Figure 13B
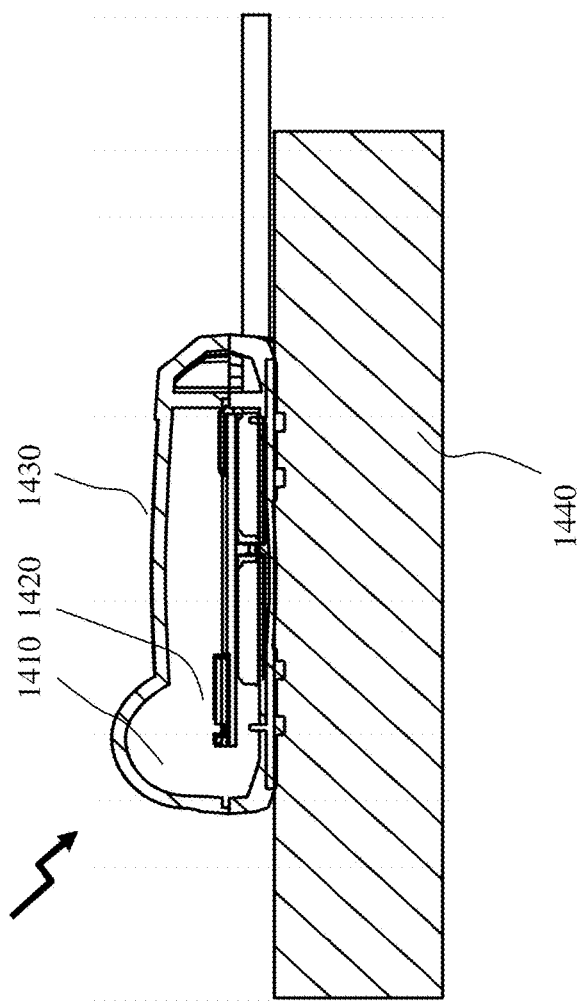
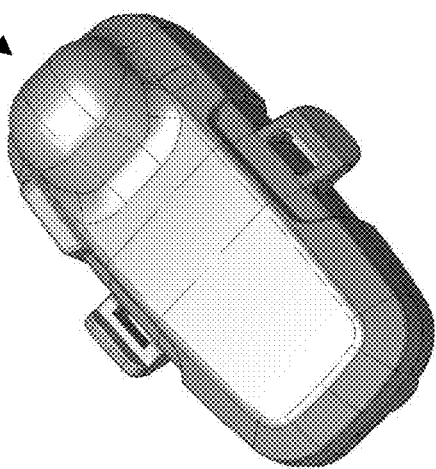
Figure 14B ns and Methods

EMBEDDED SENSOR DEVICES AND METHODS

CROSS-REFERENCE TO RELATED APPLICATIONS

This application claims the benefit of priority as a 371 National Phase entry application of PCT/CA2020/050440 filed Apr. 3, 2020; which itself claims the benefit of priority from U.S. Provisional Patent Application 62/828,585 filed Apr. 3, 2019; the entire contents of these being incorporated herein by reference.

FIELD OF THE INVENTION

The present inventions relate to sensors and more particularly to embedded sensors for construction material testing, construction material characterization, construction material monitoring and construction material selection.

BACKGROUND OF THE INVENTION

Globally, the construction industry output is forecast to rise from US$10.8 trillion in 2017 to US$12.9 trillion in 2022. Concrete and other cement-based materials represent the dominant material system within this industry with global cement production expected to increase from approximately 3.25 billion metric tons in 2010 to approximately 4.8 billion metric tons in 2030. In contrast the global gypsum market is approximately 250 million.

These materials and others employed within the construction industry are chemically active materials that often need to be analyzed so as to determine the structural properties parameters, particularly strength and other physical-mechanical properties of the final cured product, such as its potential for shrinkage. The final strength of a chemically active capillary-porous material is determined by the mixing and compacting conditions, and by its specific composition such as, but not limited to, mineral binder-to-aggregate ratio, water-to-cement, water-to-aggregate ratio and the like. Accordingly, it would be beneficial for construction companies, raw material suppliers, infrastructure owners, etc. to employ embedded sensors within these construction materials to allow for assessment of initial deployment of the construction material as well as its subsequent properties to provide these parties and/or other parties with data relating to the current and future performance of the construction material.

Further, such construction materials exhibit performance degradations as a result of direct changes in the construction material as well as other elements such as reinforcing bar (rebar) etc. embedded within or around the construction material. It would be beneficial therefore to provide embedded sensors designed to monitor and/or address corrosion-related degradation from specific parameters such as, for example, chloride, water and temperature, or gross measurements of physical properties such as conductivity and porosity.

Further, with the accumulation of data from traditional construction material testing, e.g. slump test, compression testing, etc., and embedded sensors it would be beneficial to provide these interested parties with additional services including, but not limited to, improving the selection of construction material mix for a particular project at a particular location and time, improving the assessment of proactive repair and/or remedial work, quality control monitoring etc.

Accordingly, it would be beneficial to provide construction companies, engineering companies, infrastructure owners, regulators, etc. with means to automated testing/characterization of construction materials during at least one of its manufacture, deployment in construction and subsequent infrastructure life. It would be further beneficial for such automated methods to exploit self-contained data acquisition/logging modules allowing them to be employed with ease at the different points in the life cycle of a construction material and/or construction project. It would be further beneficial for the accumulated data to be analyzed/assessed to provide automatic identification of features within the accumulated data that are characteristic of specific events or specific characteristics of the material.

Other aspects and features of the present invention will become apparent to those ordinarily skilled in the art upon review of the following description of specific embodiments of the invention in conjunction with the accompanying figures.

SUMMARY OF THE INVENTION

It is an object of the present invention to address limitations within the prior art relating to sensors and more particularly to embedded sensors for construction material testing, construction material characterization, construction material monitoring and construction material selection.

In accordance with an embodiment of the invention there is provided a sensor device comprising:
 a body comprising an electronic circuit and either a wireless transmitter or a wireless transceiver operating according to a predetermined wireless standard;
 a cable connecting one or more sensors to the electronic circuit;
 a strap attached at a first predetermined location on the body; and
 a hook disposed at a second predetermined location on the body.

In accordance with an embodiment of the invention there is provided a sensor device comprising:
 a body comprising an electronic circuit and either a wireless transmitter or a wireless transceiver operating according to a predetermined wireless standard;
 one or more slots within a sidebar disposed on a first side of the body, each slot having a dimension to accept either an elastomeric strap or a retaining strap; wherein
 a bottom surface of the body comprises:
 a contoured portion dimensioned to engage one or more elements to which the sensor device is to be attached when the strap is wrapped around the element; and
 a plurality of features disposed upon the contoured portion, the features for engaging a surface of an element the sensor device is to be attached to when the strap is wrapped around the element.

In accordance with an embodiment of the invention there is provided a sensor device comprising:
 a body comprising an electronic circuit, either a wireless transmitter or a wireless transceiver operating according to a predetermined wireless standard, and an antenna supporting operation at microwave or radio frequency frequencies according to the predetermined wireless standard;
 one or more slots within a sidebar disposed on a first side of the body, each slot having a dimension to accept either an elastomeric strap or a retaining strap; wherein
 an upper surface of the body comprises a domed or raised region within which the antenna is disposed;

a bottom surface of the body comprises:
   a contoured portion dimensioned to engage one or more elements to which the sensor device is to be attached when the strap is wrapped around the element; and
   a plurality of features disposed upon the contoured portion, the features for engaging a surface of an element the sensor device is to be attached to when the strap is wrapped around the element.

In accordance with an embodiment of the invention there is provided a sensor device comprising:
   a body comprising an electronic circuit, either a wireless transmitter or a wireless transceiver operating according to a predetermined wireless standard, and an antenna supporting operation at microwave or radio frequency frequencies according to the predetermined wireless standard;
   a first flex member attached at a first end of the body; and
   a second flex member attached at a second end of the body; wherein
   a bottom surface of the body comprises:
      a contoured portion dimensioned to engage one or more elements to which the sensor device is to be attached when the strap is wrapped around the element; and
      a plurality of features disposed upon the contoured portion, the features for engaging a surface of an element the sensor device is to be attached to when the strap is wrapped around the element.

In accordance with an embodiment of the invention there is provided a sensor device comprising:
   a body comprising an electronic circuit, either a wireless transmitter or a wireless transceiver operating according to a predetermined wireless standard, and an antenna supporting operation at microwave or radio frequency frequencies according to the predetermined wireless standard; wherein
   the antenna is disposed beneath a portion of the body which comprises a dome or protrusion within a cover of the body.

In accordance with an embodiment of the invention there is provided a method comprising:
   providing a first portion of the sensor device comprising at least a body formed from one or more resilient materials;
   providing a second portion of the sensor device formed from an elastomeric material comprising a first region and a second region; and
   attaching the second portion of the sensor device to the first portion of the sensor device such that the second region of the second portion of the sensor device is attached to a bottom surface of the first portion of the sensor device and the first region of the second portion of the sensor device extends to one side of the body; wherein
   the first region provides a strap for attaching the body to a reinforcing bar;
   the bottom surface of the first portion of the sensor device is contoured to surround a predetermined portion of the reinforcing bar; and
   the second region of the second portion of the sensor device comprises a plurality of first features for engaging a surface of the reinforcing bar when the sensor device is attached to the reinforcing bar.

In accordance with an embodiment of the invention there is provided a method comprising:
   measuring a plurality of temperatures of concrete with a sensor over a period of time from a first point in time prior to the sensor being embedded within the concrete to a second point in time after the sensor has been embedded within the concrete;
   processing plurality of temperature measurements to establish the presence of a characteristic within the plurality of temperature measurements; and
   establishing a time within the period of time associated with the characteristic established as being present within the plurality of temperature measurements.

In accordance with an embodiment of the invention there is provided a method comprising:
   establishing a threshold characteristic of a characteristic of a construction material with a predetermined material composition;
   extracting data acquired from a plurality of sensors embedded within a deployment of the construction material with the predetermined material composition where the performance characteristic of the construction material exceeds the threshold characteristic;
   iteratively varying aspects of the material composition of the construction material to establish projected performance characteristics and storing those varied material compositions exceeding the threshold characteristic;
   establishing for each stored varied material composition a cost associated with that composition;
   determining a stored varied material composition with lowest cost;
   establishing the stored varied material composition with lowest cost as the new material composition for subsequent batches of the construction material with the predetermined material composition.

In accordance with an embodiment of the invention there is provided a method comprising:
   establishing a threshold with respect to a characteristic of a construction material with a predetermined material composition;
   extracting data acquired from a plurality of sensors embedded within a deployment of the construction material with the predetermined material composition;
   executing at least one of a machine learning process and an artificial intelligent process upon the extracted data to determine at least one of achieved performance and projected performance of the characteristic of the construction material;
   determining whether the at least one of achieved performance and projected performance of the characteristic of the construction material exceeds the threshold with respect to the characteristic of the construction material with the predetermined material composition;
   upon a positive determination triggering an action.

Other aspects and features of the present invention will become apparent to those ordinarily skilled in the art upon review of the following description of specific embodiments of the invention in conjunction with the accompanying figures.

BRIEF DESCRIPTION OF THE DRAWINGS

Embodiments of the present invention will now be described, by way of example only, with reference to the attached Figures, wherein:

FIGS. 3 and 4 depict a sensor according to an embodiment of the invention;

FIGS. 5 and 6 depict a sensor according to an embodiment of the invention;

FIGS. 7 and 8 depict a sensor according to an embodiment of the invention employed in conjunction with a rebar;

FIGS. 11 and 12 depict sensors according to embodiments of the invention;

FIGS. 13A and 13B depict a sensor according to an embodiment of the invention;

FIGS. 14A and 14B depict a sensor according to an embodiment of the invention;

DETAILED DESCRIPTION

Figure 1:
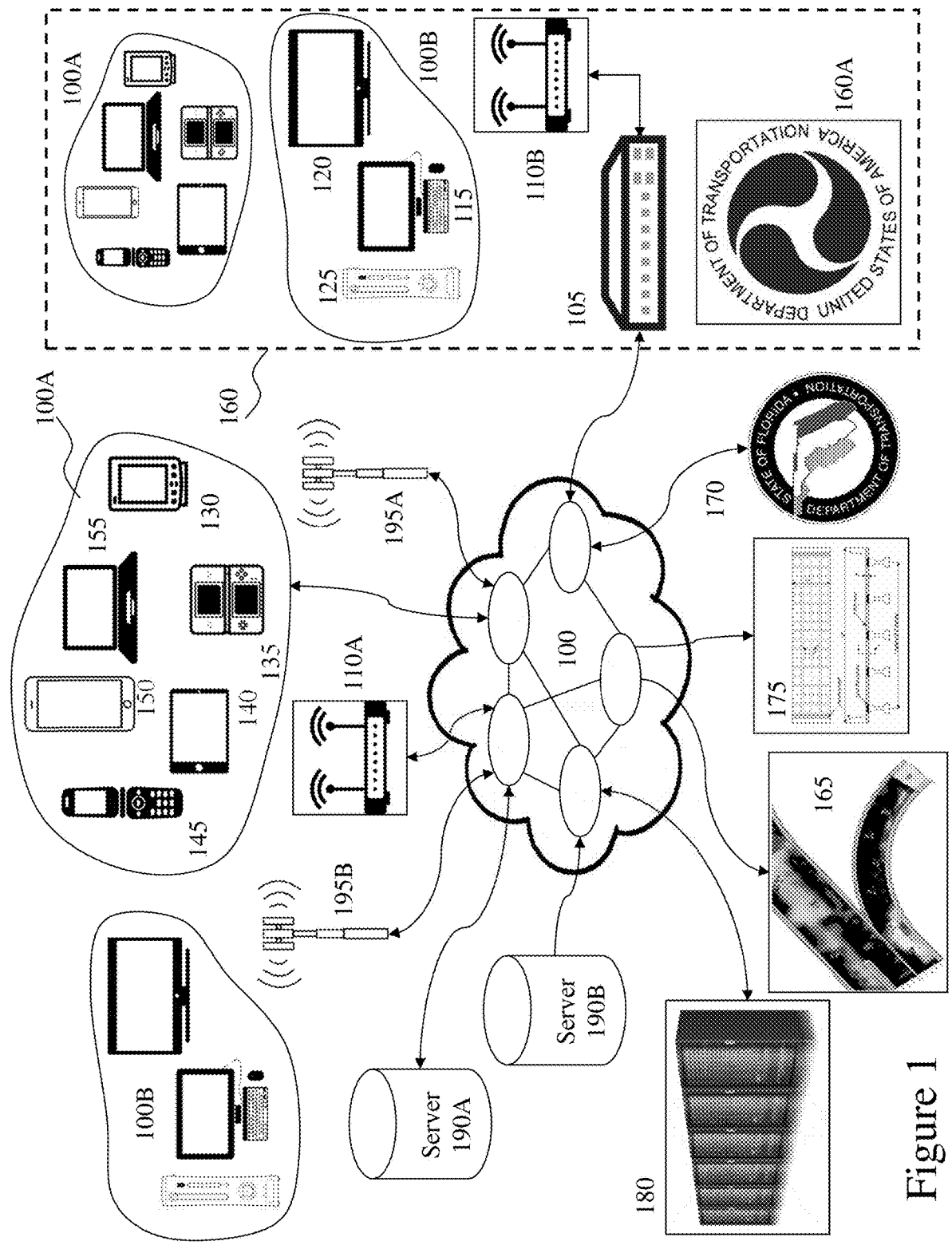
FIG. 1 depicts a network supporting communications to and from electronic devices implementing contextual based UIs according to embodiments of the invention.

The present invention is directed to sensors and more particularly to embedded sensors for construction material testing, construction material characterization, construction material monitoring and construction material selection.

The ensuing description provides exemplary embodiment(s) only, and is not intended to limit the scope, applicability or configuration of the disclosure. Rather, the ensuing description of the exemplary embodiment(s) will provide those skilled in the art with an enabling description for implementing an exemplary embodiment. It being understood that various changes may be made in the function and arrangement of elements without departing from the spirit and scope as set forth in the appended claims.

A "portable electronic device" (PED) as used herein and throughout this disclosure, refers to a wireless device that requires a battery or other independent form of energy for power. This includes devices including, but not limited to, cellular telephone, smartphone, personal digital assistant (PDA), portable computer, pager, portable multimedia player, portable gaming console, laptop computer, tablet computer, and an electronic reader.

A "fixed electronic device" (FED) as used herein and throughout this disclosure, refers to a wired and/or wireless device used which is dependent upon a form of energy for power provided through a fixed network, e.g. an electrical mains outlet coupled to an electrical utilities network. This includes devices including, but not limited to, portable computer, desktop computer, computer server, Internet enabled display, mainframe, and server cluster. Such PEDs and FEDs supporting one or more functions and/or applications including, but not limited to, data acquisition, data storage, data analysis, communications, and Internet/Web interface.

"Polyester" as used herein and throughout this disclosure may refer to, but is not limited to, category of polymers that contain the ester functional group in their main chain. This includes, but is not limited to polyesters which are naturally occurring chemicals as well as synthetics through step-growth polymerization, for example. Polyesters may be biodegradable or not. Polyesters may be a thermoplastic or thermoset or resins cured by hardeners. Polyesters may be aliphatic, semi-aromatic or aromatic. Polyesters may include, but not be limited to, those exploiting polyglycolide, polylactic acid (PLA), polycaprolactone (PCL), polyhydroxyalkanoate (PHA), polyhydroxybutyrate (PHB), polyethylene adipate (PEA), polybutylene succinate (PBS), polyethylene terephthalate (PET), polybutylene terephthalate (PBT), polytrimethylene terephthalate (PTT), and polyethylene naphthalate (PEN).

A "thermoplastic" or "thermosoftening plastic" as used herein and throughout this disclosure, refers to a category of polymers that become pliable or moldable above a specific temperature and solidify upon cooling. Thermoplastics may include, but not be limited, polycarbonate (PC), polyether sulfone (PES), polyether ether ketone (PEEK), polyethylene (PE), polypropylene (PP), poly vinyl chloride (PVC), polytetrafluoroethylene (PTFE), polyimide (PI), polyphenylsulfone (PPSU), polychlorotrifluoroethene (PCTFE or PTFCE), florinated ethylene propylene (FEP), and perfluoroalkoxy alkane (PFA).

A "metal" as used herein and throughout this disclosure may refer to, but is not limited to, material that has good electrical and thermal conductivity. Such materials may be malleable and/or fusible and/or ductile. Metals may include, but not be limited to, aluminum, nickel, copper, cobalt, chromium, silver, gold, platinum, iron, zinc, titanium, and alloys thereof such as bronze, stainless steel, stainless steel, brass, and phosphor bronze.

An "aramid" as used herein, and throughout this disclosure, refers to an aromatic polyamide. Aramids are a class of materials fibers in which the chain molecules are highly oriented along the fiber axis, so the strength of the chemical bond can be exploited. Examples include, but are not limited to fibers distributed under brand names such as Kevlar™, Technora™, Twaron™, Heracron™, Nomex™, Innegra S™ and Vectran™ as well as nylon and ultra-high molecular weight polyethylene.

A "silicone" as used herein and throughout this disclosure may refer to, but is not limited to, polymer that includes any inert, synthetic compound made up of repeating units of siloxane.

An "elastomeric" material or "elastomer" as used herein and throughout this disclosure may refer to, but is not limited to, material, generally a polymer, with viscoelasticity. Elastomers may include, but not be limited to, unsaturated rubbers such as polyisoprene, butyl rubber, ethylene propylene rubber, silicone rubber, fluorosilicone rubber, fluoroelastomers, perfluoroelastomers, and thermoplastic elastomers.

The term "flexible," as used herein, refers to the ability of a body that is capable of being bent or flexed. Something that is flexible can be, for example, resilient or malleable. The term "flexible," as used herein, refers to the ability of a body that has been subjected to an external force to return to its original size and/or shape once the external force has been removed or reduced to below a particular level.

The term "malleable," as used herein, refers to the ability of a body that has been subjected to an external force to deform and maintain, or substantially maintain, the deformed size and/or shape.

The term "elastic" as used herein, refers to or may describe or identify certain types of elastomer and/or stretchable fabrics or it may refer to the ability of a body to resist a distorting influence or stress and to return to its original size and shape when the stress is removed. Whilst solid objects will deform when sufficient force is applied a material is considered elastic and will return to its initial shape and size when the force is removed.

The term "resilient" as used herein, refers either to a material having the ability to absorb energy when it is deformed elastically, and release that energy upon unloading or to a material having the ability to resist deformation under pressure. Embodiments of the invention may employ, for example, a plastic inner ring and/or liner within which a portion of a user is inserted, e.g. a finger, wrist, etc. which supports limited deformation around which a hollow shaft motor may be employed to impart vibratory action discretely or in combination with one or more other actuators such as fluidic actuators and/or linear electrical actuators etc. The fluidic actuators may employ one or more elastic and/or elastomeric materials. Alternatively, the inner ring and/or liner may be elastic but having a higher Young's modulus that another elastic material employed within a fluidic actuator for example.

A "scaffold" or "scaffolds" as used herein, and throughout this disclosure, refers to a structure that is used to hold up, interface with, or support another material or element(s). This includes, but is not limited to, such two-dimensional (2D) structures such as substrates and films, three-dimensional (3D) structures such as geometrical objects, non-geometrical objects, combinations of geometrical and non-geometrical objects, naturally occurring structural configurations, and manmade structural configurations. A scaffold may be solid, hollow, and porous or a combination thereof. A scaffold may contain recesses, pores, openings, holes, vias, and channels or a combination thereof. A scaffold may be smooth, textured, have predetermined surface profiles and/or features. A scaffold may be intended to support one or more other materials, one or more films, a multilayer film, one type of particle, multiple types of particles etc. A scaffold may include, but not be limited to, a spine of a device and/or a framework, for example, which also supports a shell and/or a casing.

A "shell" as used herein, and throughout this disclosure, refers to a structure that is used to contain and/or surround at least partially and/or fully a number of elements within adult devices according to embodiments of the invention. A shell may include, but not limited to, a part or parts that are mounted to a scaffold or scaffolds that support elements within a device according to an embodiment of the invention.

A "casing" as used herein, and throughout this disclosure, refers to a structure surrounding a scaffold and/or shell. This includes structures typically formed from an elastomer and/or silicone to provide a desired combination of physical tactile surface properties to the device it forms part of and other properties including, but not limited to, hermeticity, liquid ingress barrier, solid particulate ingress barrier, surface sheen, and colour. A casing may include, but not limited to, a part or parts that are mounted to a scaffold or scaffolds and/or a casing or casings forming part of a device according to an embodiment of the invention.

Sensor Configurations

In order to provide construction material manufacturers, construction companies exploiting construction materials, designers, engineers, infrastructure owners, and regulators with improved data acquisition for enhanced analytics, real time monitoring, current and projected construction material characteristics, and analytics the inventors have established designs for embedded sensors or what the inventors refer to as "SMArt rocKs" (SMAKs, namely sensors) wherein SMAKs may be embedded into construction materials at various points in their life cycle from their manufacture, deployment, and post-deployment. The inventors describing several SMAK concepts within U.S. Patent Publication No. 2017/0,284,996 entitled "Embedded Wireless Monitoring Sensors", U.S. Patent Publication No. 2017/0,108,456 entitled "Electrical Methods and Systems for Concrete Testing" and U.S. Patent Publication 2018/0,238,820 entitled "Methods and Systems Relating to Construction Material Assessment."

As such these embedded sensors, may for example, be added to a concrete batch loaded onto a concrete truck at a batching plant. It is therefore possible to "tag", i.e. load into, the embedded sensor information relevant to the mix as well as delivery data etc. This information as well as other measurements made by the embedded sensors during the transportation, pouring, and placement can be accessed by wireless interface by the end user during delivery, once the concrete is delivered to the construction site, as it is poured, and during its curing, maturation processes.

As such the tagging of the SMAKs may include, but not be limited to, information such as batch identity, truck identity, date, time, location, batch mix parameters, etc. but may also include specific information such as the maturity calibration curves for the mix established by the manufacturer. Accordingly, depending upon the degree of complexity embedded into the SMAK such data may be either retrieved for remote storage and subsequently used or it may be part of the SMAKs processing of electrical measurement data such that calibration data of the concrete mix is already factored into the data provided by the SMAKs. Accordingly, the SMAKs may be added to the concrete at a manufacturing point according to the construction material. For example, this may be a concrete batching point, a production line for gypsum based sheets (namely plaster board, drywall, gypsum board), a production line for wood or fiber based products such as particle board, low density fibreboard, medium density fiberboard, etc. SMAKs may be loaded tagged already, tagged during addition, or tagged after addition. Subsequently upon delivery and employment at the construction site the SMAKs may be read for information regarding their manufacture, delivery process, etc.

Accordingly, once deployed the SMAKs may be read for acquired information from the one or more sensors within the SMAK and then subsequently, depending upon the battery—power consumption etc., periodically read for lifetime data of the construction material. In each instance the acquired data may be acquired wirelessly and stored on a user's PED or it may then be pushed to a network and therein to one or more servers. For devices wirelessly interrogating the SMAKs these may be executing a software application which presents to the user concrete parameter data either as provided from the SMAK(s) directly using the calibration curves stored within or upon the device using calibration curve data stored within the SMAK but not processed by it, stored within the device or retrieved from the data stored upon a remote server. As depicted the SMAKs may be interrogated with a PED or alternatively the data stored upon the remote server may be interrogated and accessed by a PED.

A SMAK may be enabled by a wireless signal, by a vibration measured by the SMAK exceeding a threshold, via an electrical circuit forming part of the SMAK being completed, an increase in humidity beyond a threshold, a decrease in light, etc. Accordingly, SMAKs according to embodiments of the invention may support tagging with information at deployment, the embedding of calibration data such as concrete maturity calibration curves in the sensor, and the acquisition of sensor data.

Based upon the combination of SMAKs within the construction material, their wireless interrogation, and mobile/cloud based software applications other technical enhancements may be implemented, including for example:

Weather forecast API, such that the ambient temperature prediction in conjunction with current concrete data can be used to predict/project the strength identifying quality problems earlier;

Automatic detection of construction material deployment, e.g. for concrete from an electrical connection being completed once the concrete is poured or change in the pressure, humidity, light etc. or a characteristic vibration from a nail gun or other tool for plasterboard, particle board etc. or detecting a characteristic feature within a temperature-time trend that is characteristic of concrete pouring;

Tagging the sensor using NFC with smartphone;

Data integrity and management on remote servers;

Data analytics and/or artificial intelligence on data analysis as the SMAK manufacturer may acquire data from a large number of job sites allowing additional analytics, reporting, alarms etc.;

A SMAK manufacturer may establish so-called "big data" on construction material properties and construction material cycles/processes across a large number of job sites, geographic regions, time frames etc. allowing them to provide feedback from their server based processes to the end user;

Push notifications, such as for example the concrete contractor is notified when is the time to remove the formwork based upon actual concrete curing data; and Heat optimization wherein for example closed loop feedback of the temperature history and strength development can be employed to optimize heating employed in cold climates to ensure the concrete slabs gain sufficient strength within a specific period.

In addition to measuring, for example, temperature, DC electrical conductivity, and AC electrical conductivity it would be evident that additional parameters as discussed and described within US 2017/0,284,996; US 2017/0,108,456 and US 2018/0,238,820 may be monitored including moisture content, concrete relative humidity, pH, mixture consistency, workability (slump), hydraulic pressure, segregation, cracking, penetration of external ions into concrete, dispersion of fibers, and dispersion of chemical additives and supplementary cementitious materials.

Exemplary Network and Device Configurations for Construction Material Characterisation Now referring to FIG. 1 there is depicted a network 100 supporting communications to and from electronic devices implementing contextual based UIs according to embodiments of the invention. As shown first and second user groups 100A and 100B respectively interface to a telecommunications network 100. Within the representative telecommunication architecture, a remote central exchange 180 communicates with the remainder of a telecommunication service providers network via the network 100 which may include for example long-haul OC-48/OC-192 backbone elements, an OC-48 wide area network (WAN), a Passive Optical Network, and a Wireless Link. The central exchange 180 is connected via the network 100 to local, regional, and international exchanges (not shown for clarity) and therein through network 100 to first and second wireless access points (AP) 195A and 195B respectively which provide Wi-Fi cells for first and second user groups 100A and 100B respectively. Also connected to the network 100 are first and second Wi-Fi nodes 110A and 110B, the latter of which being coupled to network 100 via router 105. Second Wi-Fi node 110B is associated with Government Body 160A and environment 160 within which are first and second user groups 100A and 100B. Second user group 100B may also be connected to the network 100 via wired interfaces including, but not limited to, DSL, Dial-Up, DOCSIS, Ethernet, G.hn, ISDN, MoCA, PON, and Power line communication (PLC) which may or may not be routed through a router such as router 105.

Within the cell associated with first AP 110A the first group of users 100A may employ a variety of portable electronic devices including for example, laptop computer 155, portable gaming console 135, tablet computer 140, smartphone 150, cellular telephone 145 as well as portable multimedia player 130. Within the cell associated with second AP 110B are the second group of users 100B which may employ a variety of fixed electronic devices including for example gaming console 125, personal computer 115 and wireless/Internet enabled television 120 as well as cable modem 105.

Also connected to the network 100 are first and second APs which provide, for example, cellular GSM (Global System for Mobile Communications) telephony services as well as 3G and 4G evolved services with enhanced data transport support. Second AP 195B provides coverage in the exemplary embodiment to first and second user groups 100A and 100B. Alternatively the first and second user groups 100A and 100B may be geographically disparate and access the network 100 through multiple APs, not shown for clarity, distributed geographically by the network operator or operators. First AP 195A as show provides coverage to first user group 100A and environment 160, which comprises second user group 100B as well as first user group 100A. Accordingly, the first and second user groups 100A and 100B may according to their particular communications interfaces communicate to the network 100 through one or more wireless communications standards such as, for example, IEEE 802.11, IEEE 802.15, IEEE 802.16, IEEE 802.20, UMTS, GSM 850, GSM 900, GSM 1800, GSM 1900, GPRS, ITU-R 5.138, ITU-R 5.150, ITU-R 5.280, and IMT-2000. It would be evident to one skilled in the art that many portable and fixed electronic devices may support multiple wireless protocols simultaneously, such that for example a user may employ GSM services such as telephony and SMS and Wi-Fi/WiMAX data transmission, VOIP and Internet access. Accordingly, portable electronic devices within first user group 100A may form associations either through standards such as IEEE 802.15 and Bluetooth as well in an ad-hoc manner.

Also connected to the network 100 are concrete mapping environment 165, State Body 170, and Bridge Structure environment 175 as well as first and second servers 190A and 190B which together with others not shown for clarity, may host according to embodiments of the inventions multiple services associated with one or more organizations, including but not limited to, a provider of the software operating system(s) and/or software application(s) associated with the electronic device(s), a provider of the electronic device, provider of one or more aspects of wired and/or wireless communications, provider of the electrical measurement devices, provider of mapping analysis software, provider of electrical measurement analysis software, global position system software, materials databases, building databases, regulatory databases, license databases, construction organizations, websites, and software applications for download to or access by FEDs, PEDs, and electrical measurement systems. First and second servers 190A and 190B may also host for example other Internet services such as a search engine, financial services, third party applications and other Internet based services.

Accordingly, it would be evident to one skilled in the art that electrical measurement systems and/or rebar corrosion analysis according to embodiments of the invention described above in respect of FIGS. 1 to 9B and 11 to 22 may be connected to a communications network such as network 100 either continuously or intermittently. It would be further evident that the electrical resistivity measurements of concrete and/or rebar together with the analysis of the measurements and their mapping may be triggered as a result of activities triggered by, for example, the Government Body 160A and/or State Body 170 in order to address regulatory requirements, safety concerns etc.

Accordingly, the engineers, workers and/or technicians who will be performing the measurements may be able to access Bridge Structure Environment 175 to obtain architect drawings, engineering data, design data, etc. relating to the concrete structure being assessed. It would be evident that other databases addressing other environments such as for example, shopping malls, road surfaces, public walkways, residential housing, and commercial buildings may be accessed where the requirements for assessment relate to these structures and the regulatory bodies may be similarly transportation or include others such as Department of Housing, Federal Highway Administration, and Bureau of Industry and Security. Where all or part of the structure being assessed has been previously assessed then data may be retrieved from the Concrete Mapping Environment for example. It would be evident that with coordinated based measurement acquisition that an engineer may view in real time a contour map of the structure being assessed as the data is acquired and accordingly may ask for additional measurements or repeated measurements to be performed. Additionally, previous contour mapping and electrical measurements may allow for targeted re-assessment of areas of concern at a different frequency to that of the overall structure.

Figure 2:
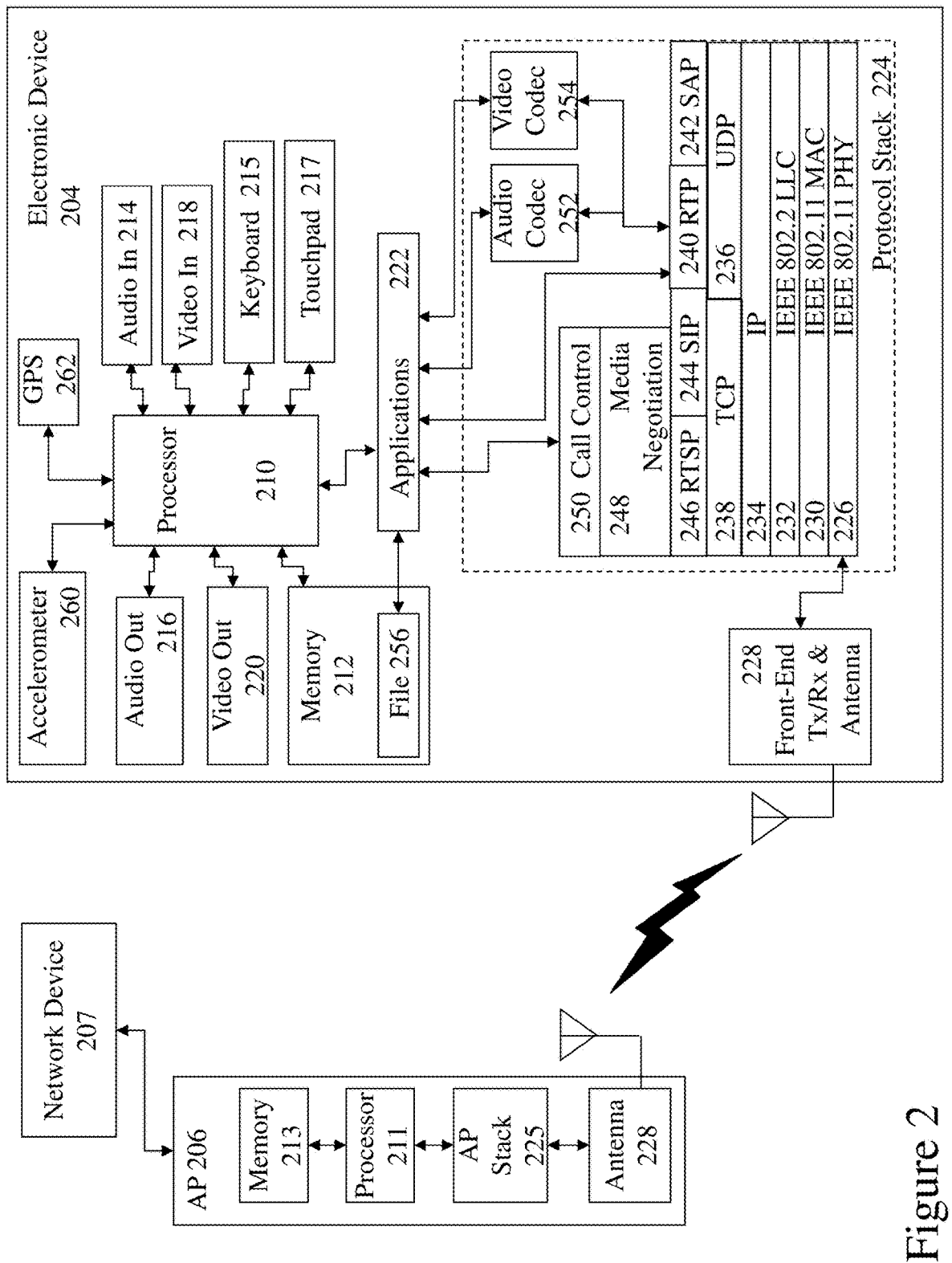
FIG. 2 depicts an electronic device and network access point supporting contextual based UIs according to embodiments of the invention.

Now referring to FIG. 2 there is depicted an electronic device 204 and network access point 207 supporting contextual based UIs according to embodiments of the invention. Electronic device 204 may for example be a portable electronic device or a fixed electronic device and may include additional elements above and beyond those described and depicted. Also depicted within the electronic device 204 is the protocol architecture as part of a simplified functional diagram of a system 200 that includes an electronic device 204, such as a smartphone 1055, an access point (AP) 206, such as first AP 110, and one or more network devices 207, such as communication servers, streaming media servers, and routers for example such as first and second servers 190A and 190B respectively. Network devices 207 may be coupled to AP 206 via any combination of networks, wired, wireless and/or optical communication links such as discussed above in respect of FIG. 1. The electronic device 204 includes one or more processors 210 and a memory 212 coupled to processor(s) 210. AP 206 also includes one or more processors 211 and a memory 213 coupled to processor(s) 211. A non-exhaustive list of examples for any of processors 210 and 211 includes a central processing unit (CPU), a digital signal processor (DSP), a reduced instruction set computer (RISC), a complex instruction set computer (CISC) and the like. Furthermore, any of processors 210 and 211 may be part of application specific integrated circuits (ASICs) or may be a part of application specific standard products (ASSPs). A non-exhaustive list of examples for memories 212 and 213 includes any combination of the following semiconductor devices such as registers, latches, ROM, EEPROM, flash memory devices, non-volatile random-access memory devices (NVRAM), SDRAM, DRAM, double data rate (DDR) memory devices, SRAM, universal serial bus (USB) removable memory, and the like.

Electronic device 204 may include an audio input element 214, for example a microphone, and an audio output element 216, for example, a speaker, coupled to any of processors 210. Electronic device 204 may include a video input element 218, for example, a video camera, and a video output element 220, for example an LCD display, coupled to any of processors 210. Electronic device 204 also includes a keyboard 215 and touchpad 217 which may for example be a physical keyboard and touchpad allowing the user to enter content or select functions within one of more applications 222. Alternatively, the keyboard 215 and touchpad 217 may be predetermined regions of a touch sensitive element forming part of the display within the electronic device 204. The one or more applications 222 that are typically stored in memory 212 and are executable by any combination of processors 210. Electronic device 204 also includes accelerometer 260 providing three-dimensional motion input to the process 210 and GPS 262 which provides geographical location information to processor 210.

Electronic device 204 includes a protocol stack 224 and AP 206 includes a communication stack 225. Within system 200 protocol stack 224 is shown as IEEE 802.11 protocol stack but alternatively may exploit other protocol stacks such as an Internet Engineering Task Force (IETF) multimedia protocol stack for example. Likewise, AP stack 225 exploits a protocol stack but is not expanded for clarity. Elements of protocol stack 224 and AP stack 225 may be implemented in any combination of software, firmware and/or hardware. Protocol stack 224 includes an IEEE 802.11-compatible PHY module 226 that is coupled to one or more Front-End Tx/Rx & Antenna 228, an IEEE 802.11-compatible MAC module 230 coupled to an IEEE 802.2-compatible LLC module 232. Protocol stack 224 includes a network layer IP module 234, a transport layer User Datagram Protocol (UDP) module 236 and a transport layer Transmission Control Protocol (TCP) module 238.

Protocol stack 224 also includes a session layer Real Time Transport Protocol (RTP) module 240, a Session Announcement Protocol (SAP) module 242, a Session Initiation Protocol (SIP) module 244 and a Real Time Streaming Protocol (RTSP) module 246. Protocol stack 224 includes a presentation layer media negotiation module 248, a call control module 250, one or more audio codecs 252 and one or more video codecs 254. Applications 222 may be able to create, maintain and/or terminate communication sessions with any of devices 207 by way of AP 206. Typically, applications 222 may activate any of the SAP, SIP, RTSP, media negotiation and call control modules for that purpose. Typically, information may propagate from the SAP, SIP, RTSP, media negotiation and call control modules to PHY module 226 through TCP module 238, IP module 234, LLC module 232 and MAC module 230.

It would be apparent to one skilled in the art that elements of the electronic device 204 may also be implemented within the AP 206 including but not limited to one or more elements of the protocol stack 224, including for example an IEEE 802.11-compatible PHY module, an IEEE 802.11-compatible MAC module, and an IEEE 802.2-compatible LLC module 232. The AP 206 may additionally include a network layer IP module, a transport layer User Datagram Protocol (UDP) module and a transport layer Transmission Control Protocol (TCP) module as well as a session layer Real Time Transport Protocol (RTP) module, a Session Announcement Protocol (SAP) module, a Session Initiation Protocol (SIP) module and a Real Time Streaming Protocol (RTSP) module, media negotiation module, and a call control module.

Portable and fixed electronic devices represented by electronic device 204 may include one or more additional wireless or wired interfaces in addition to the depicted IEEE 802.11 interface which may be selected from the group comprising IEEE 802.15, IEEE 802.16, IEEE 802.20, UMTS, GSM 850, GSM 900, GSM 1800, GSM 1900, GPRS, ITU-R 5.138, ITU-R 5.150, ITU-R 5.280, IMT-2000, DSL, Dial-Up, DOCSIS, Ethernet, G.hn, ISDN, MoCA, PON, and Power line communication (PLC).

Embedded Sensor Designs

Now referring to FIGS. 3 and 4 there are depicted first and second views 300 and 400 of a sensor according to an embodiment of the invention. In first view 300 the sensor body 320 according to an embodiment of the invention is depicted together with strap 310 and sensor cable 330. The sensor cable 330 links the sensor body 320 to one or more remote sensors tethered through the sensor cable 330. These sensors may, for example, include but not be limited to temperature sensors, vibration sensors, humidity sensors, pH sensors, ion sensors, and acoustic sensors.

As depicted in FIG. 4 the second view 400 depicts the sensor body 320, strap 310, and sensor cable 330 together with the following features:

Mechanical push button activation switch 410;

"Softened" shaped and/or rounded edges and/or corners 420 to deflect impacts from particulates/components of the material the sensor body 320 is to be embedded in and/or forces arising from pouring of the material the sensor body 320 is to be embedded in etc.;

Off-centre cable exit 430 for the sensor cable 330;

Band/strap hook 440 to which the strap 310 can be attached when the sensor is attached to an element of a structure which will be embedded within a material;

Hole 450 to provide additional attachment option;

LED indicator 460 indicating status of sensor body 320 to a user before it is embedded within a material is to monitor; and Surface label 470 for information such as two-dimensional (2D) machine readable code (e.g. a QR code, barcode etc.), product information, product branding, etc. as well as allowing space for a user to write deployment and/or site-specific content.

Optionally, within other embodiments of the invention the cable exit 430 may be disposed to the other side of the body 320 or central. Within other embodiments of the invention multiple sensor cables may be employed either each off-centre on one end of the sensor device or off-centre on opposite ends of the device, central to an axis of the device etc.

Figure 6B:
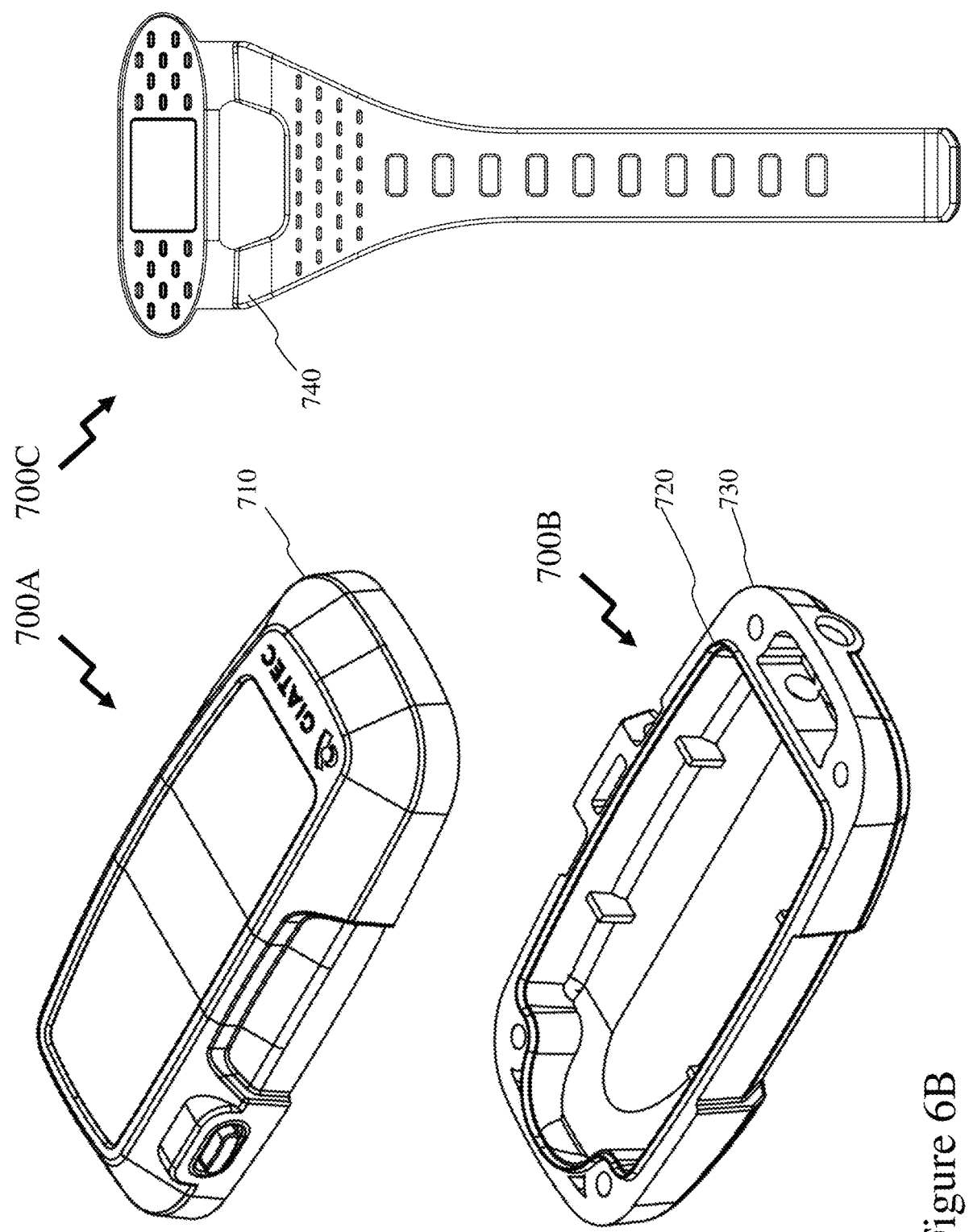

Now referring to FIGS. 5 and 6 there are depicted first and second views 500 and 600 of a sensor according to an embodiment of the invention. In first view 500 the sensor body 320 according to an embodiment of the invention is depicted together with strap 310 and sensor cable 330. The strap 310 as depicted comprises first and second holes 510 and 540 respectively to provide an alternate means of mounting the sensor body 320, grips 520 allowing a construction worker to employ the strap, which may be elastomeric or another material, whilst wearing gloves or wet hands etc. Also depicted are strap holes 530 which may be varied with different sensors according to embodiments of the invention in aspects such as size, shape, number, etc. to attach to the band/strap hook 440. The strap holes 530 and the band/strap hook 440 may be varied in dependence upon one or more factors including, for example, dimensions and/or material of an element the sensor body 320 is to be attached to, the material the sensor is to be embedded within, and whether the user is expected to be wearing gloves or not.

In second view 600 these features are also depicted together with first features 610 on the back of the strap 610 and second features 620 on the back of the sensor body 320. These first features 610 and second features 620 provide increased friction and/or adhesion to an element of a structure to which the sensor body 320 is attached. The second features 620 may for example be formed from an elastomer such as that employed for the strap 310. Further, the lower surface of the sensor body 320 incorporates a shaped portion 630 designed such that the shaped portion 630 conforms to the external geometry of an element, e.g. a rebar. Referring to Table 1 there are depicted standard U.S. rebar dimensions for which the shaped portion 630 of the sensor body 320 may be designed. Standard rebar comprising a circular rod with ribs around its outer surface. Within embodiments of the invention the shaped portion 630 of the sensor body 320 may be designed to fit one standard rebar geometry or it may be designed to fit multiple standard rebar geometries. Optionally, within another embodiment of the invention an intermediate element may be disposed between the lower surface of the sensor body 320 and the rebar or another element. Accordingly, the shaped portion 630 of the sensor body 320 may be dimensioned to fit a first set of rebar geometries, e.g. imperial bar sizes 6 to 8 whilst the intermediate element may be dimensioned for imperial bar sizes 2 to 3, 2 to 4, or 4 to 5 for example.

TABLE 1

US Standard Rebar Dimensions

| Imperial bar size | Metric bar size (soft) | Nominal diameter | |
|---|---|---|---|
| | | inch | mm |
| 2 | 6 | 0.250 = ¼ | 6.35 |
| 3 | 10 | 0.375 = ⅜ | 9.525 |
| 4 | 13 | 0.500 = ½ | 12.7 |
| 5 | 16 | 0.625 = ⅝ | 15.875 |
| 6 | 19 | 0.750 = ¾ | 19.05 |
| 7 | 22 | 0.875 = ⅞ | 22.225 |
| 8 | 25 | 1.000 = ⁸⁄₈ | 25.4 |
| 9 | 29 | 1.128 ≈ ⁹⁄₈ | 28.65 |
| 10 | 32 | 1.270 ≈ ¹⁰⁄₈ | 32.26 |
| 11 | 36 | 1.410 ≈ ¹¹⁄₈ | 35.81 |
| 14 | 43 | 1.693 ≈ ¹⁴⁄₈ | 43 |
| 18 | 57 | 2.257 ≈ ¹⁸⁄₈ | 57.3 |

For example, referring to first and second views 700A and 700B respectively in FIG. 7 and first and second images 800A and 800B in FIG. 8 depict a sensor according to an embodiment of the invention employed in conjunction with a rebar for deployment within a structure formed from concrete. First view 700A depicts a side elevation view before the strap 310 is attached to a rebar 710, second view 700B a three-dimensional (3D) perspective view before the strap 310 is attached to the rebar 710, and first image 800A an end elevation view before the strap 310 is attached to the rebar 710. Accordingly, the first features 610 on the lower surface of the strap 310 as depicted in FIG. 6 engage the rebar 710 as the strap 310 is wrapped around it and then attached to the sensor body 320. Similarly, the second features 620 on the lower surface of the sensor body 320 as depicted in FIG. 6 engage the rebar 710. Within second image 800B the sensor body 320 is depicted attached to a rebar with strap 310 whilst the sensor cable 330 is depicted as being retained in position along the rebar 710 with second straps 720, for example elastomeric wraps, cable ties etc.

Figure 10:
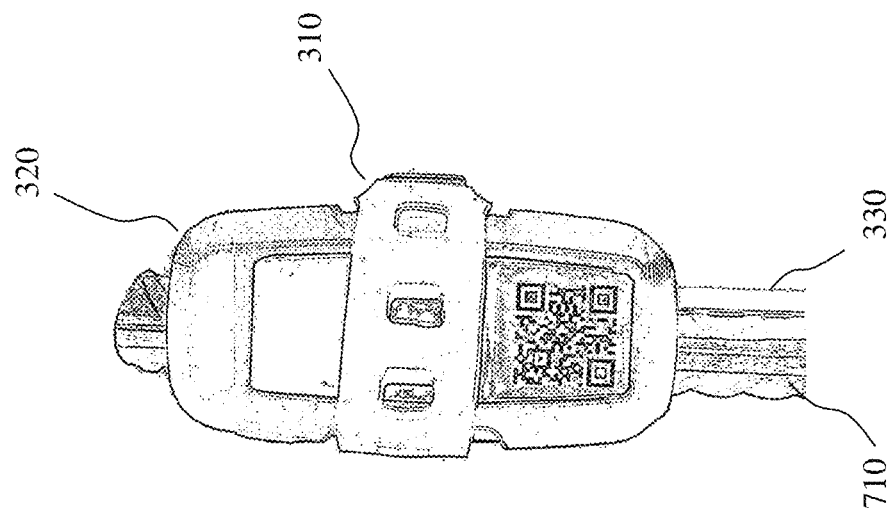
FIGS. 9 and 10 depict a sensor according to an embodiment of the invention employed in conjunction with a rebar.
Figure 9:
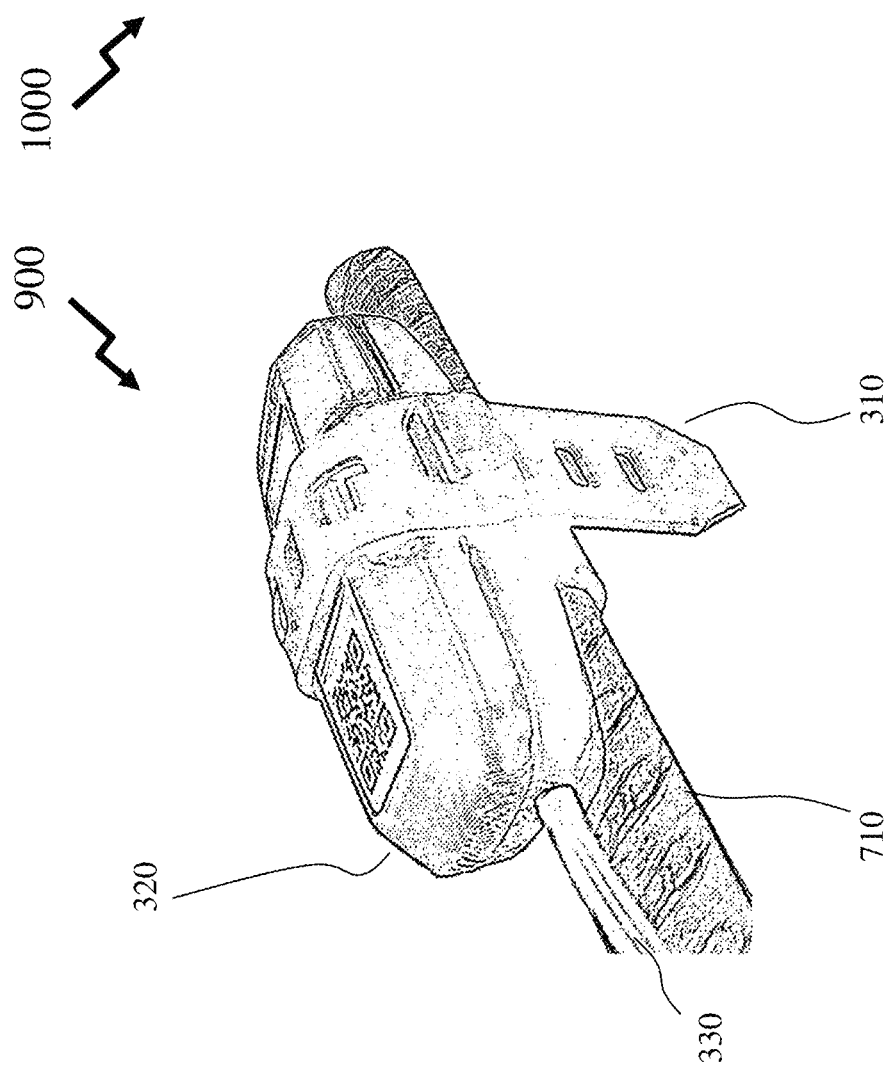

Referring to FIGS. 9 and 10 images 900 and 1000 respectively depict a sensor according to an embodiment of the invention employed in conjunction with a rebar 710 once the strap 310 has been wrapped around the rebar 710 and the sensor body 320. As evident, the sensor cable 310 is offset from the centre of the sensor body 320 such that the sensor cable 310 sits along the upper side of the rebar 710.

Now referring to FIGS. 11 and 12 there are depicted first image 1100A together with first and second images 1200A and 1200B respectively which depict a sensor according to an embodiment of the invention. As depicted the sensor comprises a sensor body 1110 together a slot 1120 within a sidebar 1150 which provides a slot for a band or strap to fit through it and be attached via the band/strap hook 1140 on the other side of the sensor body 320. Whilst FIGS. 3 to 11 depict configurations with the band/strap hook such as band/strap hook 340 and band/strap hook 1140 on the other side of the sensor body from the point of attachment of the strap and/or slot 1120 it would be evident that in other embodiments of the invention the band/strap hook may be disposed in a different position on the sensor body such as sensor body 320 or sensor body 1120. Also depicted within the sidebar 1150 are secondary attachment slots 1130, such as for example retaining straps such as elastomeric straps, rigid straps or cable ties for example, to attach the sensor body 1110 to an element of infrastructure. First and second images 1200A and 1200B respectively depict images where the slot allows management of "excess" length of an attachment means such as a strap or band.

Second image 1100B depicts a sensor according to an embodiment of the invention comprising a body 1170 with first and second hooks 1160 and 1170 respectively for attachment of straps according to embodiments of the invention.

Within embodiments of the invention a sensor may incorporate a wireless transmitter or wireless transceiver, e.g. Bluetooth, which employs a wireless antenna. Accordingly, when a sensor according to such an embodiment of the invention is embedded within a material or structure then the closer the wireless antenna is to the surface of the material or structure then either the stronger the wireless signal(s) transmitted and/or received from another device external to the material or sensor or the deeper within the material or structure the sensor according to an embodiment of the invention can be embedded. Now referring to FIG. 13A there are depicted first and second images 1300A and 1300B respectively of a sensor according to an embodiment of the invention wherein a dome or protrusion above the sensor body allows a wireless antenna forming part of the sensor to be positioned higher above a rebar or element of a structure etc. when the sensor is attached on the rebar or element of the structure etc. Similarly, referring to FIG. 14A there are depicted first and second images 1400A and 1400B respectively of a sensor according to an embodiment of the invention wherein a dome or protrusion above the sensor body allows a wireless antenna forming part of the sensor to either be positioned higher above a rebar or element of a structure etc. or radiate through an increased distance of air or an inert gas when the sensor is attached on the rebar or element of the structure etc. In other embodiments of the invention the region may be filled with an inert fluid/solid/foam filling the sensor body when the sensor is attached on an element of the structure etc. where wireless propagation through the medium is not as difficult such as with wet concrete. The design depicted in first and second images 1400A and 1400B in FIG. 14A provides an increased housing volume relative to that depicted in first and second images 1300A and 1300B in FIG. 13A.

However, for embedding sensors within wireless absorbing materials such as wet concrete the inventors have also established through appropriate design of the dome or protrusion that the amplitude of the wireless signals in the near-field can be increased thereby affecting the far-field propagation.

This is evident from FIGS. 13B and 14B. FIG. 13B depicts perspective image 1300D and cross-section 1300E for a sensor without dome or protrusion. FIG. 14B depicts perspective image 1400C and cross-section 1400D for a sensor with dome or protrusion. Accordingly, cross-section image 1300E depicts the sensor housing 1330 with antenna 1310 with first volume 1320 between the antenna 1310 and sensor housing 1330. As evident from cross-section 1400D the sensor housing 1430 above the antenna 1420 provides a larger second volume 1410. Accordingly, when deployed within a material and attached to the same depth to a substrate 1340 or substrate 1440 the increased second volume 1410 provides reduced material to the surface in comparison to the first volume 1320.

Figures 15, 16:
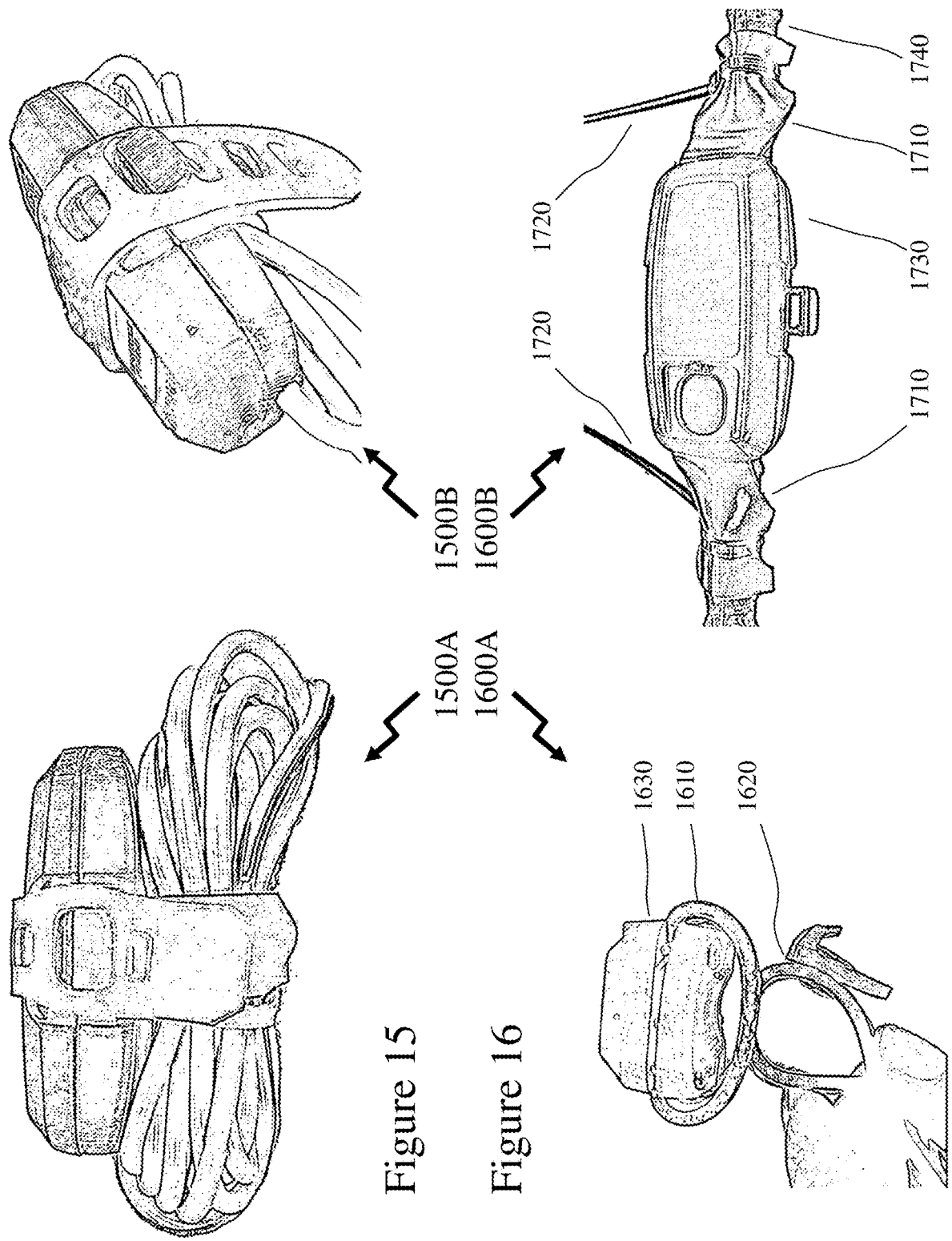
FIG. 15 depicts a sensor according to an embodiment of the invention in an exemplary shipment configuration.
FIG. 16 depicts alternate attachment strap/band variations for sensors according to embodiments of the invention.

Now referring to FIG. 15 there is depicted a sensor according to an embodiment of the invention in first and second images 1500A and 1500B respectively for an exemplary shipment configuration wherein the strap now provides a means of retaining the coiled cable sensor allowing different sensors to be shipped with different sensor cable lengths, such as 0.3 meters, 0.5 meters, 1.0 meter, and 2 meters for example (12 inches, 20 inches, 39 inches, and 6 feet 6 inches). Whilst the embodiments of the invention depicted in FIGS. 3 to 15 are depicted with a single sensor cable it would apparent to one of skill in the art that multiple sensor cables may be employed, either upon one end of the sensor body or both ends of the sensor body.

Referring to FIG. 16 there are depicted first and second images 1600A and 1600B depict alternate attachment strap/band variations for sensors according to embodiments of the invention. Within first image 1600A an upper strap 1610 is looped around and below the sensor body 1630. The upper strap 1610 is attached to a lower strap 1610, such as strap 310 depicted in FIGS. 3 to 7 respectively, may be attached to a rebar for example. The upper strap 1610 provides for movement of the sensor body 1630 relative to the rebar or structural element to absorb shocks and/or impacts or allowing the ridge sensor to move within a limited range relative to the rebar or structure.

In second image 1600B a sensor body 1730 is attached to a rebar or structural element, depicted as rebar 1740, via first and second flex members 1710 disposed at each end of the sensor body 1730 and cable tied 1720 that wrap around the rebar 1740 and retain each flex member 1710 against the rebar 1740. Alternatively, the first and second flex members 1710 may be nailed, stapled, taped, or glued to a structural member, e.g. wood, plaster board, or particle board. The first and second flex members 1710 may be flat sections of a rubber, elastomer, etc.

Figure 17:
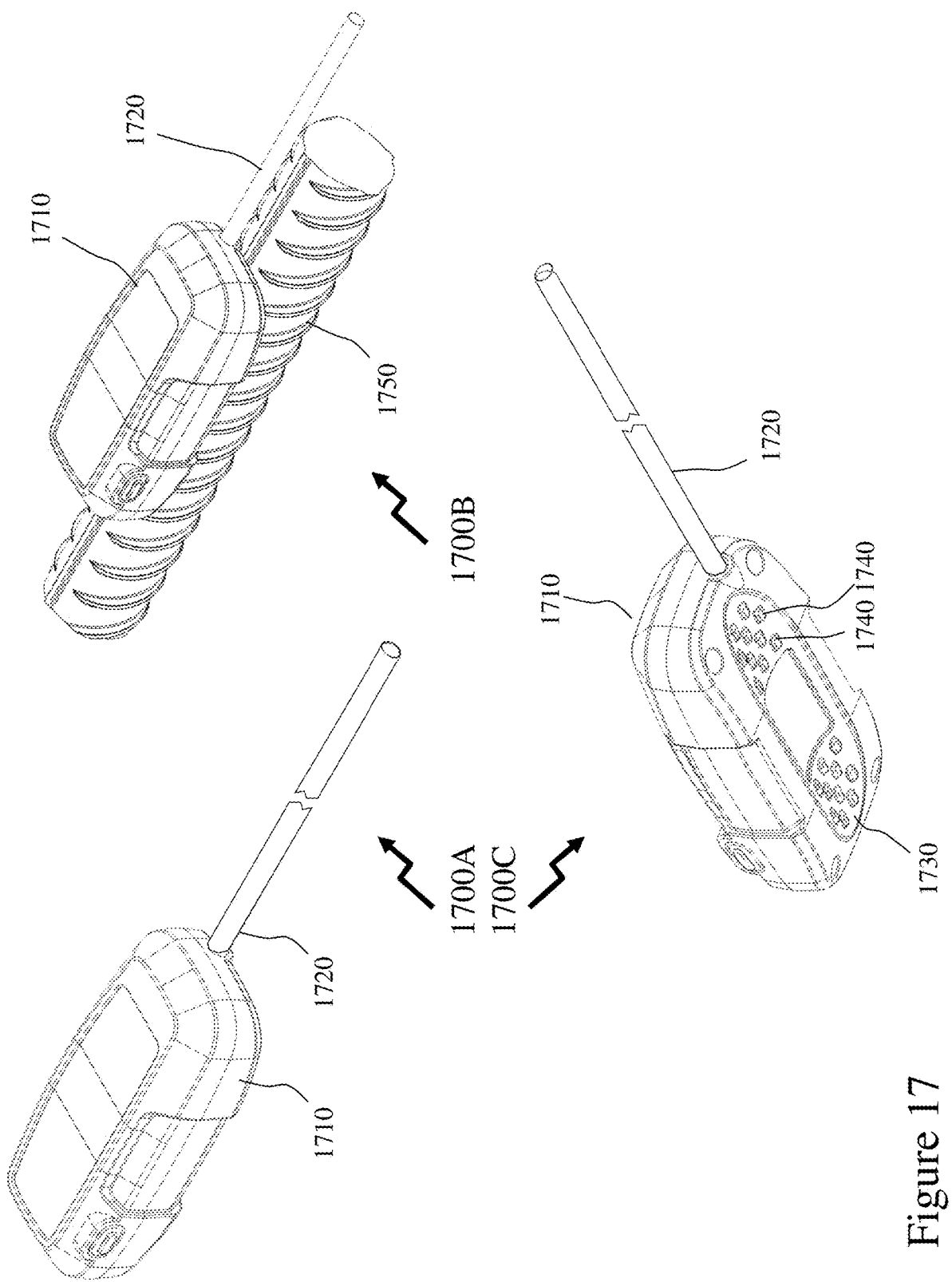
FIG. 17 depicts a sensor according to an embodiment of the invention.

Now referring to FIG. 17 there are depicted first to third images 1700A to 1700C respectively with respect to a sensor according to an embodiment of the invention. In common with the sensor depicted in FIGS. 3 to 7 respectively the sensor comprises a sensor body 1710 and a sensor cable 1720 but does not incorporate a strap forming part of the sensor. The sensor body 1710 also incorporates on the lower surface 1730 which is designed to conform to the outer surface of a structural element, such as rebar 1750, which has features 1740 for improving grip/friction between the sensor body 1710 and rebar 1750.

Figure 18:
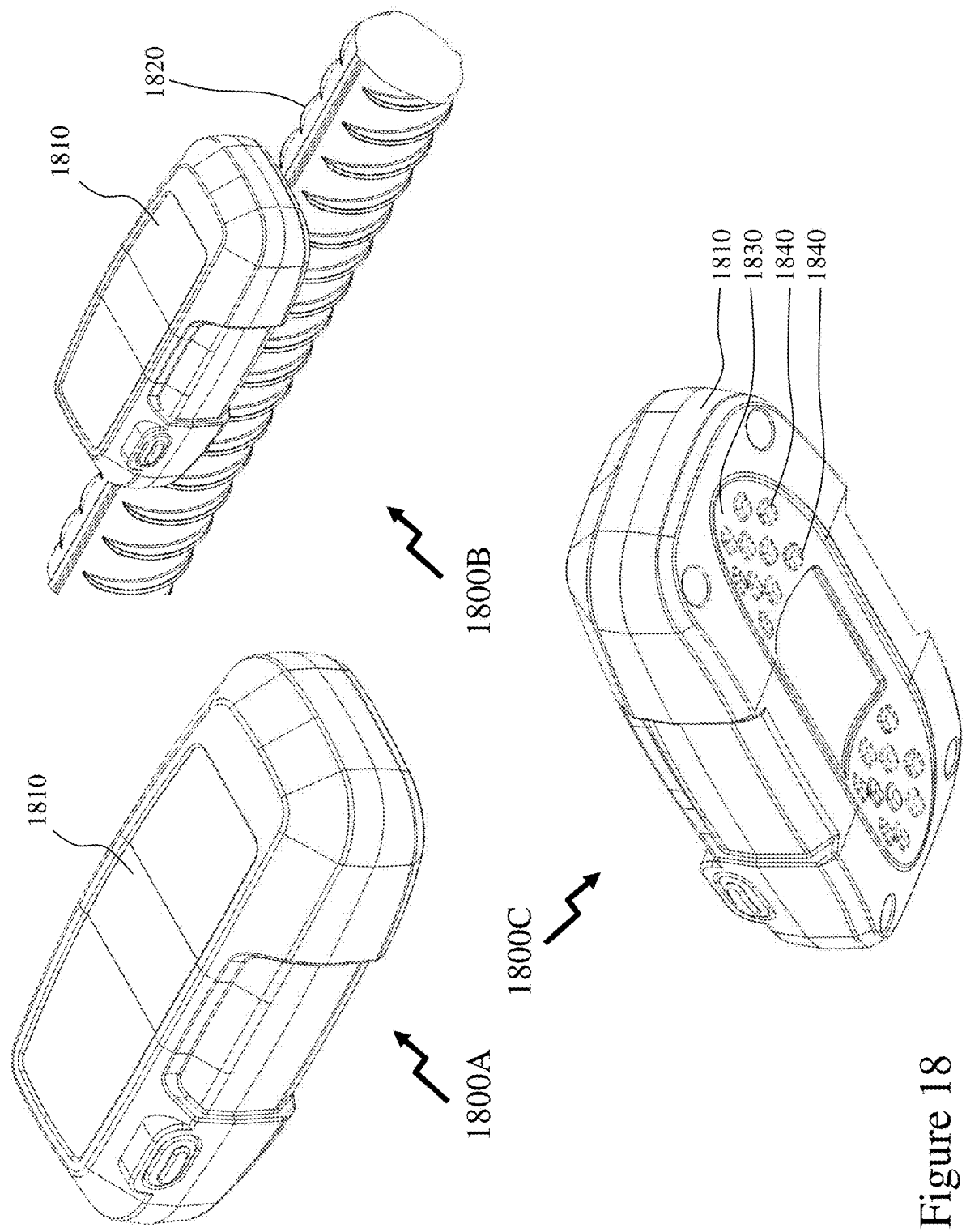
FIG. 18 depicts a sensor according to an embodiment of the invention.

With the embodiments of the invention depicted in FIGS. 3 to 17 the sensor cable couples a remote sensor to the sensor body to electronics within the sensor body. The sensor body may incorporate one or more other sensors. Referring to FIG. 18 there is depicted a sensor according to an embodiment of the invention wherein the sensor now comprises a sensor body 1710 which is self-contained with the one or more sensors integrated within it. The sensor body 1810 also incorporates on the lower surface 1830 which is designed to conform to the outer surface of a structural element, such as rebar 1820, which has features 1840 for improving grip/friction between the sensor body 1810 and rebar 1820.

Accordingly, with respect to FIGS. 3 to 18 respectively, then the following sensor related concepts may be employed within one or more embodiments of the invention with respect to a strap/band:

- an elastomeric band may be used to quickly and securely fix the device to a range of construction rebar diameters;
- an elastomeric band wraps around the rebar and the unit securing via a rigid hook on the unit housing;
- a matrix of raised details on the underside of the sensor body act to grip a rebar or other element to prevent movement and/or rotation;
- molded grip details also feature on the inner contact surface of an elastomeric band to act to grip a rebar or other element to prevent movement and/or rotation.
- a width of an elastomeric band may be adjusted/optimized where it is in contact with the rebar to reduce rotation/twisting;
- an elastomeric band features locating holes that allow for the unit to be screwed/nailed to a suitable surface, e.g. slab floor, wood form work, etc.;
- an elastomeric band features grips to aid easier installation, including the use of gloved hands or wet hands;
- a hook location and orientation promote the excess band material being directed away from the device and down into the concrete. This reduces the possibility of the band protruding up and out of the concrete surface or the material the sensor is to be embedded within; and
- an elastomeric band also acts to manage the sensor cable in packaging and shipping such that the sensor cable is managed and can remain in shipping state under install on the job site. Unit does not need to be 'unwrapped' during the tagging and identification process.

Accordingly, with respect to FIGS. 3 to 18 respectively, then the following sensor related concepts may be employed within one or more embodiments of the invention with respect to a housing of a sensor module:

- a main housing volume is optimized to provide internal clearances for best wireless, e.g. Bluetooth, antenna signal and performance;
- the sensor unit is designed to modularize assembly steps, e.g. an upper housing incorporates the sensor electronics, antenna, etc. and can be processed as one modular section before integration with the base;
- the sensor unit is design to modularize assembly steps, e.g. an upper housing incorporates the sensor electronics and can be processed as one modular section before integration with the base;
- a large top-label surface allows 2D machine readable code to be printed (e.g. QR code, barcode), product numbering etc. as well providing space for a user to write identification information;
- the sensor housing edges and corners are rounded/angled to deflect concrete (or another material to which the sensor is to be embedded within) during a pouring, casting, blown process for applying the concrete or other material;
- softened edges of the overall product volume reduce possibility of the unit being "hit" by workers onsite;
- the housing base is shaped (curved) to conform to the top surface of standard rebars giving greater stability; and
- surface texture is optimized for concrete adhesion.

Accordingly, with respect to FIGS. 3 to 18 respectively, then the following sensor-related concepts may be employed within one or more embodiments of the invention with respect to a housing of a sensor module:

- a mechanical button/switch located on the sensor can be activated easily during the tagging process one-handed and the sensor can be activated once installed on rebar (if required);
- a LED indicator located so it can be easily seen from the top orientation by users and/or workers;
- the sensor cable exit is offset from the centre of the rebar in order to promote wire installation along the edge/side of the rebar rather than the top or bottom where it might be subject to more damage and the exit location will reduce issues such as hanging wires and potential catch points;

the sensor cable is sealed into the housing to avoid moisture/material ingress which can be implemented in a number of ways including, but not limited to, local compound potting, compression gasket and over molded seal; and an autonomous detection of when the sensor comes in contact with the concrete.

Within FIGS. 13 and 14 a dome or protrusion above and around the wireless antenna location, e.g. a Bluetooth antenna, allowing the signal performance to be improved. Within the embodiments of the invention described and depicted within FIGS. 3 to 12 the wireless antenna is deployed within an internal cavity of the sensor which has been designed for improved signal performance when embedded within a material, such as concrete.

Figure 29:
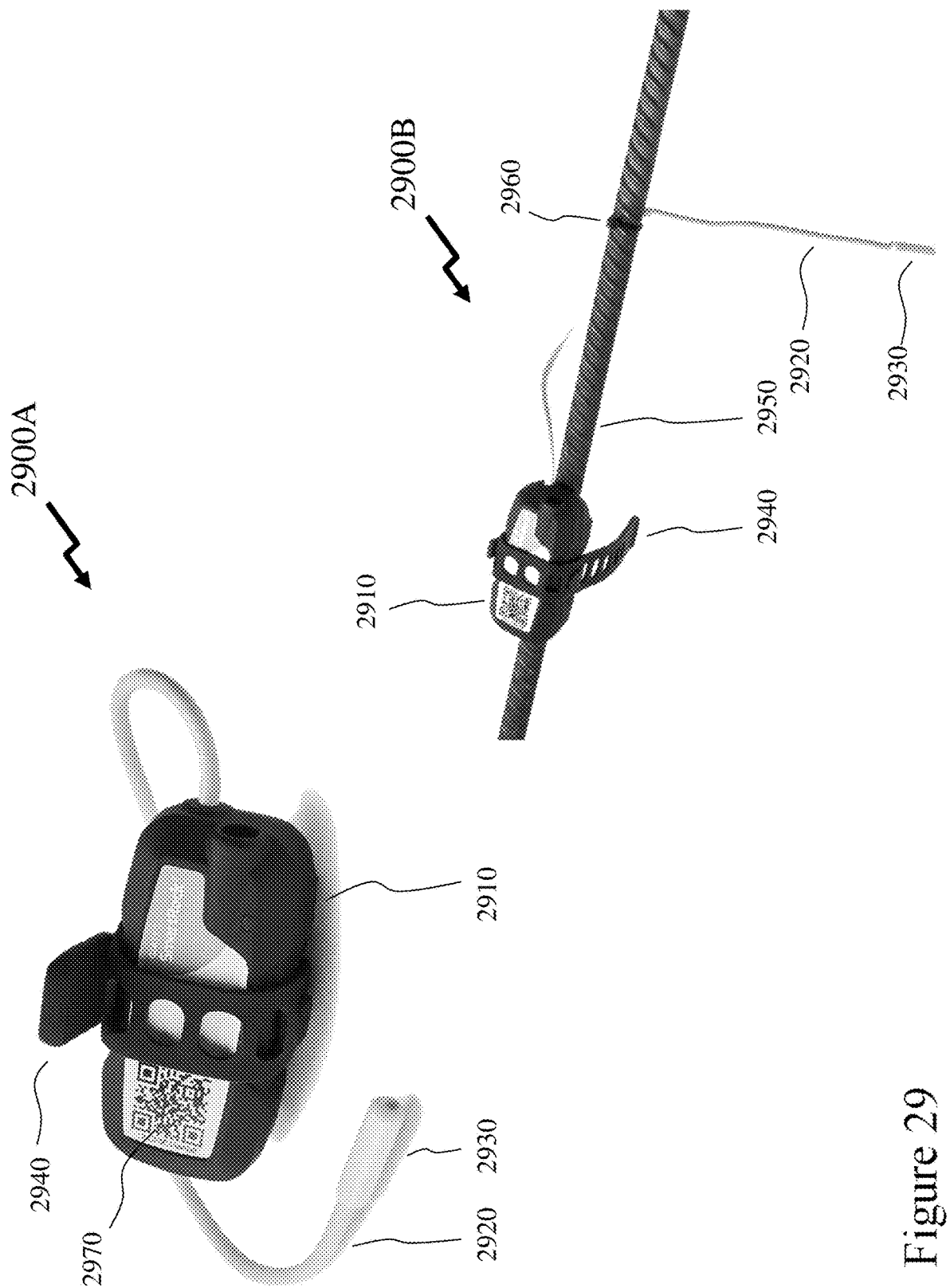
FIG. 29. depicts a sensor according to an embodiment of the invention discretely and as attached to a reinforcing bar.

Now referring to FIG. 29 there is depicted a sensor according to an embodiment of the invention discretely and as attached to a reinforcing bar exploiting some of the design features of the sensors described and depicted in FIGS. 3 to 18 but employing a discrete separate strap rather than an integrated strap. First and second views 2900A and 2900B respectively depict the sensor discretely and as attached to a reinforcing bar (rebar). As depicted in first view 2900A the sensor comprises a sensor body 2910, a sensor cable 2920, a sensor housing 2930 and a strap 2940. Also depicted is a barcode 2970 (specifically a QR code allowing the identity of the sensor to be acquired by a PED to establish wireless communications with the sensor. Accordingly, when deployed as depicted in second view 2900B the strap 2940 wraps around the sensor 2910 attaching it to the rebar 2950. The sensor cable 2950 is deployed so that a first portion extends along the rebar 2950 whilst a second portion hangs below the rebar so that the sensor housing 2930 is below the rebar 2950. When concrete is poured the sensor body 2910, sensor cable 2920 and sensor housing 2930 are embedded within the wet concrete such that the sensor housing 2930 is deeper into the concrete than the sensor housing 2910. Accordingly, by varying the first portion relative to the second portion the sensor housing 2930 on different sensors may be varied. As depicted in second view 2900B the sensor cable is tied to the rebar 2950 via a cable tie 2960. Optionally, multiple cable ties may be employed as may other means of retaining the sensor cable 2920 and/or sensor housing 2930 against the rebar 2950. Sensors may be implemented with different lengths of sensor cable 2920 such as 150 mm, 225 mm, 300 mm, 450 mm etc. (6", 9", 12", 18" etc.).

Figure 30:
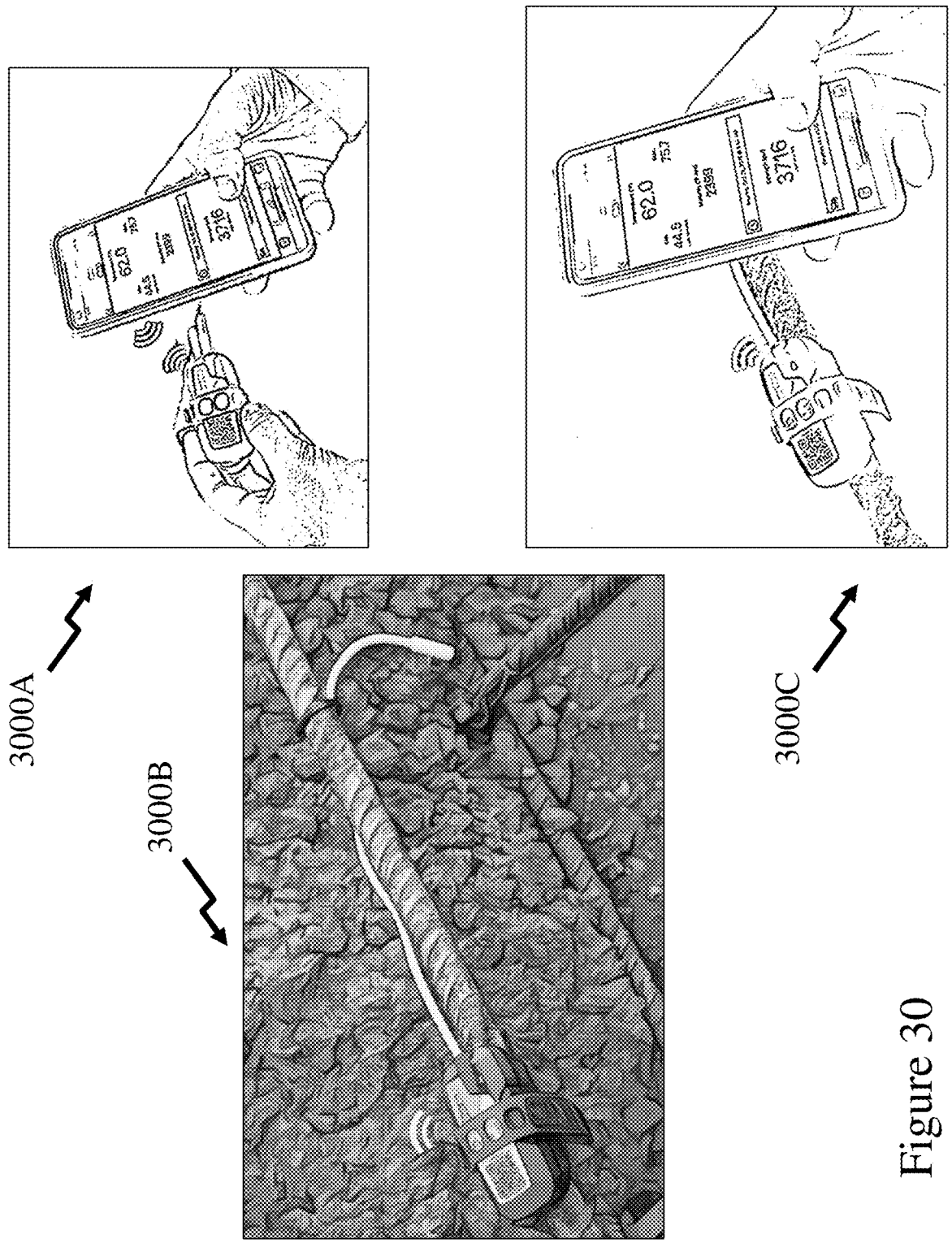
FIG. 30 depicts a sensor according to the embodiment of the invention as depicted in FIG. 29 prior to deployment, in deployed state and being read in deployed state.

Now referring to FIG. 30 there are depicted first to third views 3000A to 3000C with respect to a sensor according to the embodiment of the invention as depicted in FIG. 29 prior to deployment, in deployed state and being read in deployed state. Referring to first view 3000A a user is depicted wirelessly communicating from a smartphone, although other PEDs may be employed. Initially, the user may acquire an image of the barcode on the sensor establishing the unique identity of the sensor such that their PED can establish communications to that PED discretely even in the presence of multiple sensors within wireless range of the PED (or FED within other embodiments of the invention). Once wireless communications are established with the sensor the user's PED may transfer information to the sensor and/or acquire information from the sensor. In these instances, the sensor detects wireless communications and awakes from a sleep state. Within other embodiments of the invention the sensor housing, such as sensor housing 2930 in FIG. 29, may be stored within an opening within the sensor, such as sensor recess 3120 in FIG. 31, wherein removal of the sensor housing from the opening within the sensor triggers the sensor to awake as removal from its initial shipped state with the sensor housing deployed within the opening within the sensor body would indicate imminent deployment.

Accordingly, once data has been acquired from and/or provided to the sensor it is deployed and concrete pouring begins. As depicted in second view 3000B the sensor is attached to the rebar with the strap and the sensor cable tied to the rebar. As depicted in third view 3000C the sensor can be subsequently wirelessly communicated with to retrieve sensor data, material characteristics, etc. even when buried in the wet concrete. Second and third views 3000B and 3000C showing only partial concrete pouring to allow the rebar and sensor to be visible.

Figure 31:
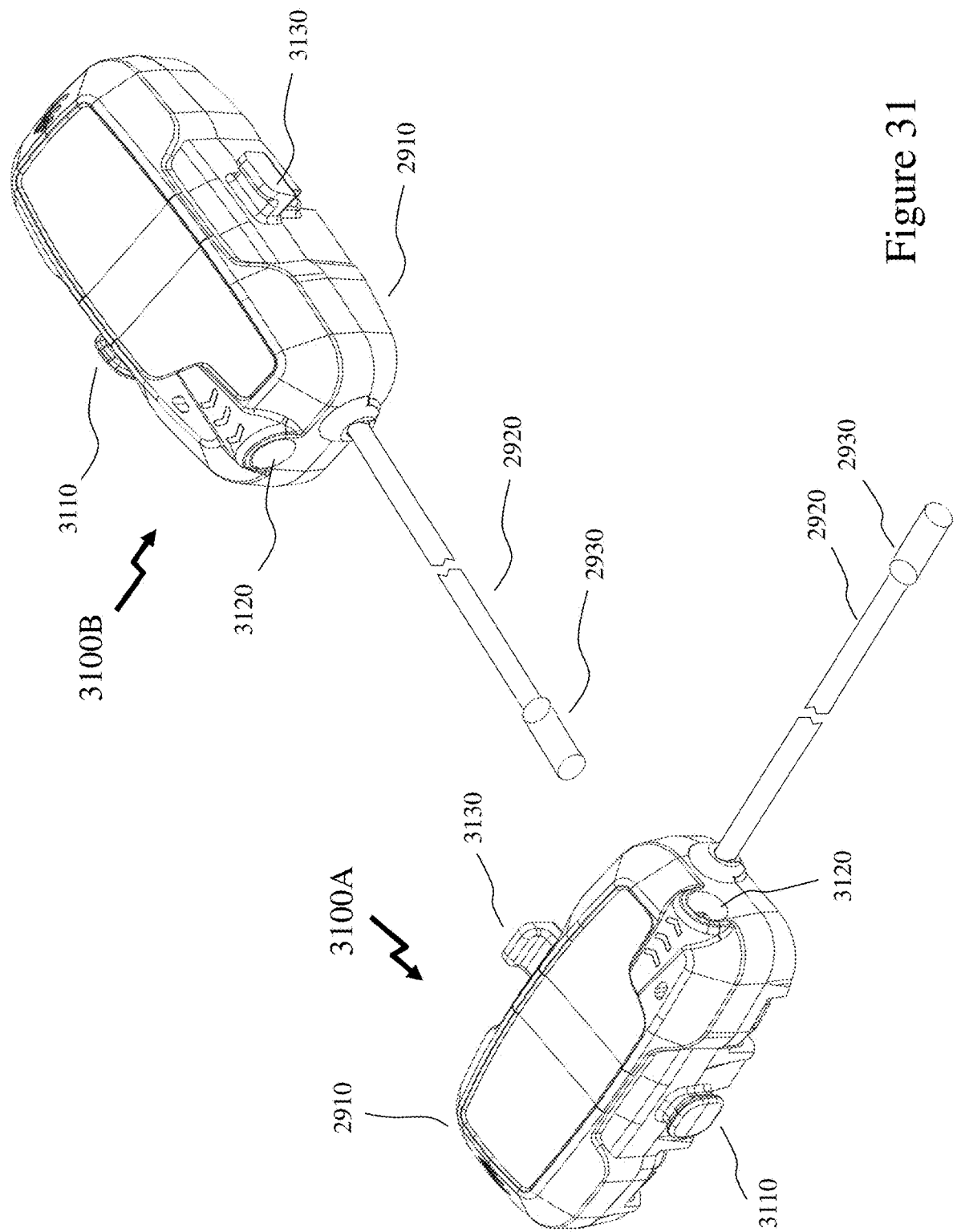
FIGS. 31 and 32 depict the sensor according to the embodiment of the invention depicted in FIG. 29 in perspective.
Figure 32:
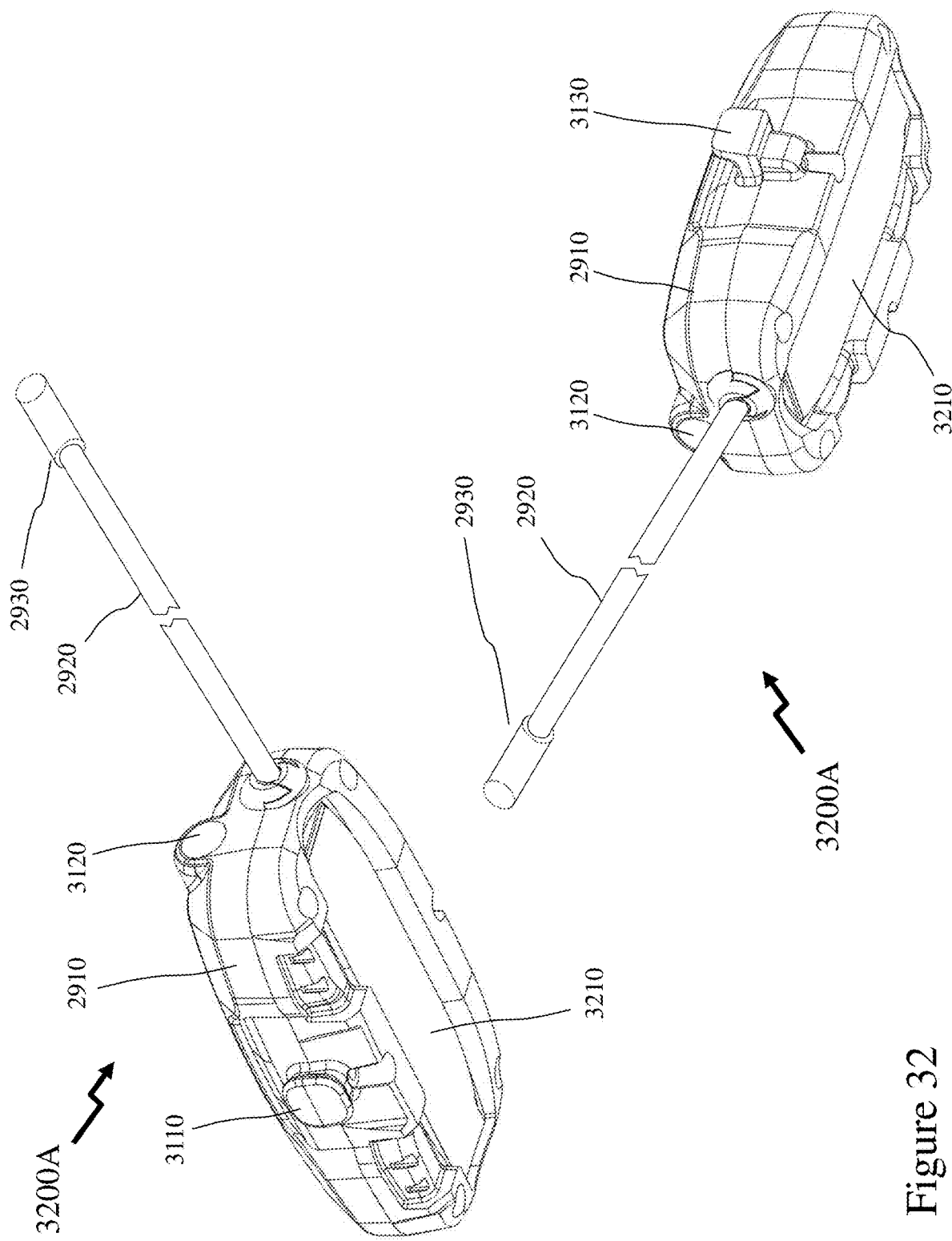

FIGS. 31 and 32 depict the sensor according to the embodiment of the invention depicted in FIG. 29 in perspective. Within FIG. 31 there are depicted first and second views 3100A and 3100B wherein each is from an upper perspective view. As depicted the sensor comprises the sensor body 2910, sensor cable 2920 and sensor housing 2930. Also depicted are the sensor recess 3120 within which the sensor housing 2930 is initially positioned at shipment within these embodiments of the invention such that as described above removal of the sensor housing 2930 from the sensor recess 3120 triggers an awakening of the sensor electronics. For example, the sensor housing 2930 may contain a small permanent magnet which when within the sensor recess 3120 causes a magnetic proximity sensor within the electronics of the sensor be in a first state, e.g. open circuit Accordingly, removal of the sensor housing 2930 from the sensor recess 3120 results in the magnetic proximity sensor being in a second state, e.g. closed circuit so that the electronics is activated, e.g. a battery connection made, or transitioned from a sleep state to an awake state. It would be evident to one of skill in the art that other methods of establishing whether the sensor housing 2930 is within or removed from the sensor recess 3120 may be employed. Optionally, once activated the electronics cannot be transitioned back upon replacement of the sensor housing 2930 within the sensor recess 3120 such that if a mechanical switch or pressure switch were employed the sensor could not be accidentally turned off again when deployed from material filling the sensor recess. However, techniques such as magnetic activation may allow removal and re-insertion such that is a sensor is activated and then not deployed it can be put back into a sleep state for subsequent use.

Also depicted in first and second views 3100A and 3100B are a first hook 3110 on one side of the sensor body 2910 and a second hook 3130 on the other side. Accordingly, the strap, not shown for clarity, is attached to the first hook 3110, wrapped around the sensor body 2910 and the structure to which the sensor is attached, e.g. rebar, and attached to the second hook 3130. The strap may be formed from an elastomeric material or formed from a non-elastic material. Optionally, with an elastomeric strap a single strap may accommodate multiple different sizes of mounting element, e.g. multiple rebar sizes. Within other embodiments of the invention the first and second hooks 3110 and 3130 may be on the same side of the body.

Now referring to FIG. 32 there are depicted first and second views 3200A and 3200B wherein each is from a lower perspective view. Accordingly, there again evident the sensor body 2910, sensor cable 2920, sensor housing 2930 as described in respect of FIG. 29 together with the first hook 3110, sensor recess 3120 and second hook 3130 described in respect of FIG. 31. However, as evident in the first and second views 3200A and 3200B respectively the bottom of the sensor has a profiled surface 3210 such that it can sit upon a rebar. It would be evident that within embodiments of the invention a common profiled surface 3210 may be employed with multiple sizes of rebar or different sensors may have different profiled surfaces 3210 tailored to different rebar sizes. Optionally, within other embodiments of the invention the profiled surface 3210 may have a geometry tailored for other mounting elements with a non-circular geometry.

Automated Pour Time Determination

Figure 19:
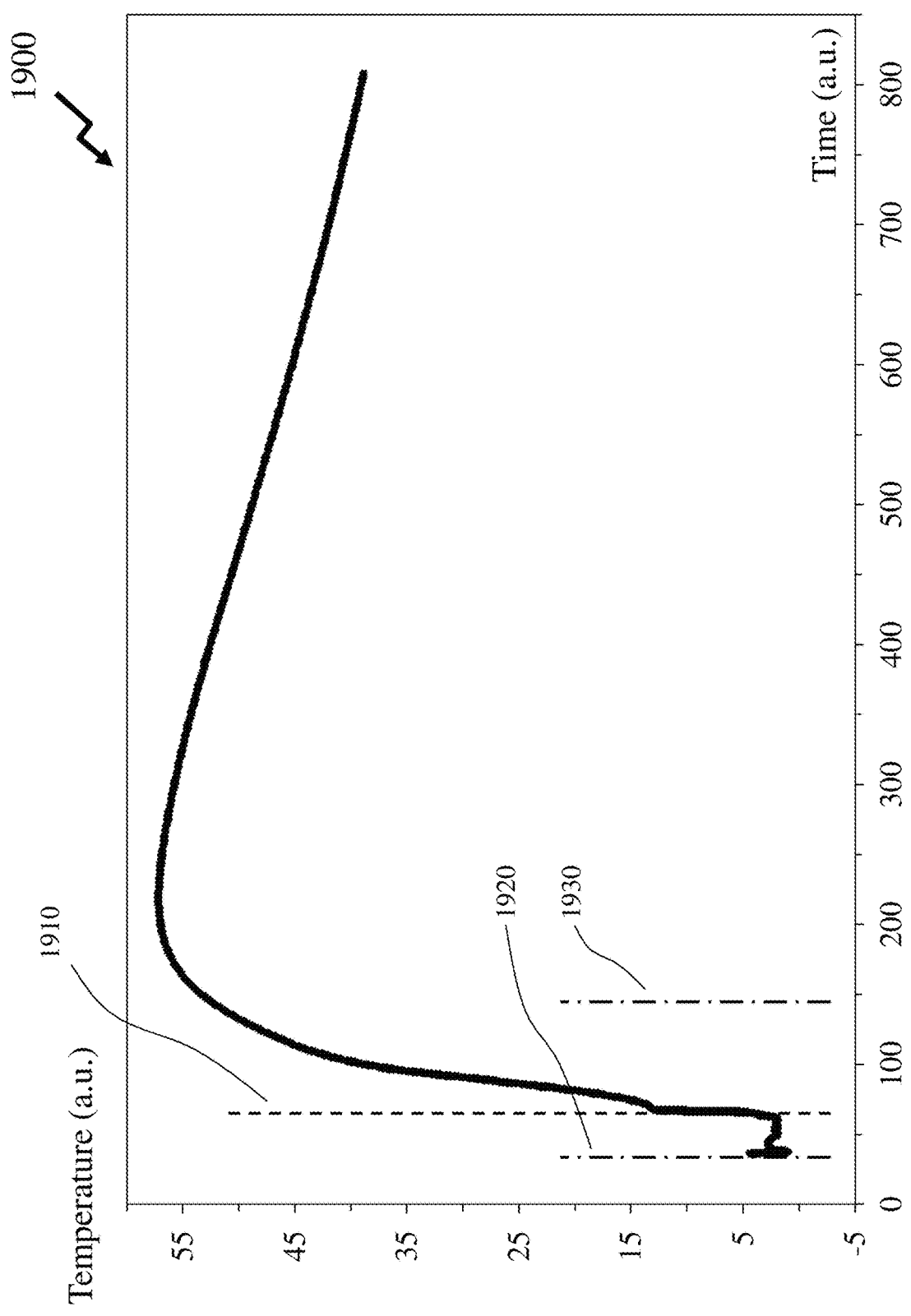
FIG. 19 depicts a plot of temperature versus time obtained with a sensor according to an embodiment of the invention depicted features characteristic of pouring time.

The inventors have established that when a temperature sensor is embedded into a material which cures, e.g. concrete, the measured temperature-time graph displays a certain behavior that is a characteristic of concrete hydration. Referring to FIG. 19 there is depicted an exemplary plot 1900 of temperature versus time together with indicator 1910 representative of the point in time that the sensor (temperature sensor) comes into contact with the material, e.g. concrete. Accordingly, the inventors have established a machine learning algorithm which processed historical data acquired from temperature sensors in which a user has labeled the correct pouring time. This machine algorithm has been employed upon thousands of temperature-time graphs wherein the labeled data was used as inputs to a convolutional neural network, although another form of algorithm such as multi-layer perceptron, recurrent neural networks, support vector machines, etc. may be employed. The network is capable of identifying features that are characteristic of concrete pouring during algorithm training. Once training is performed, whenever a user connects to the sensor using a device exploiting software established by the inventors then this algorithm is called.

Figure 20:
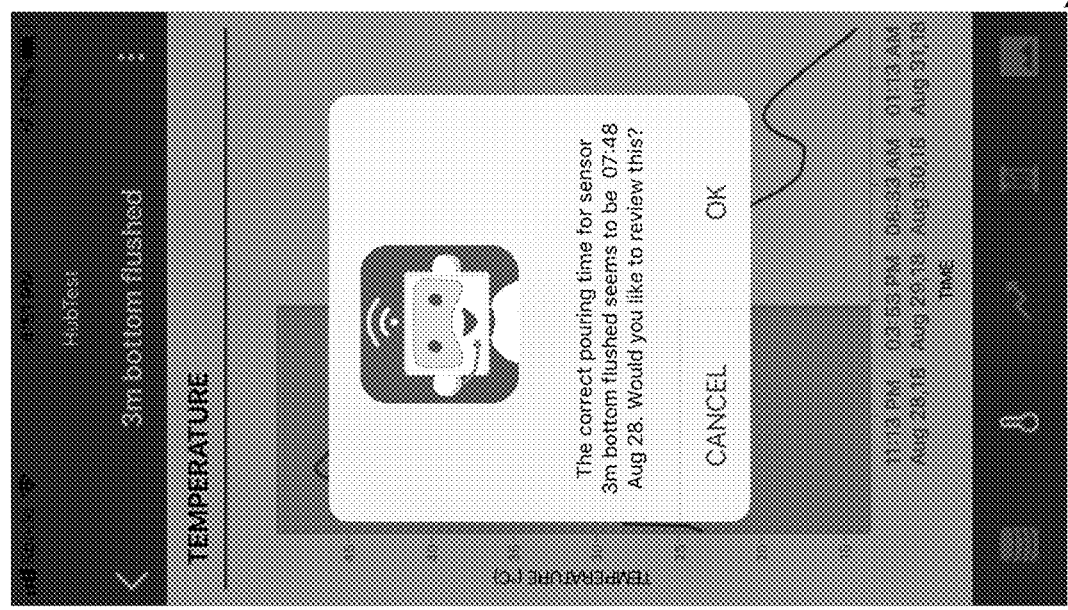
Figure 22:
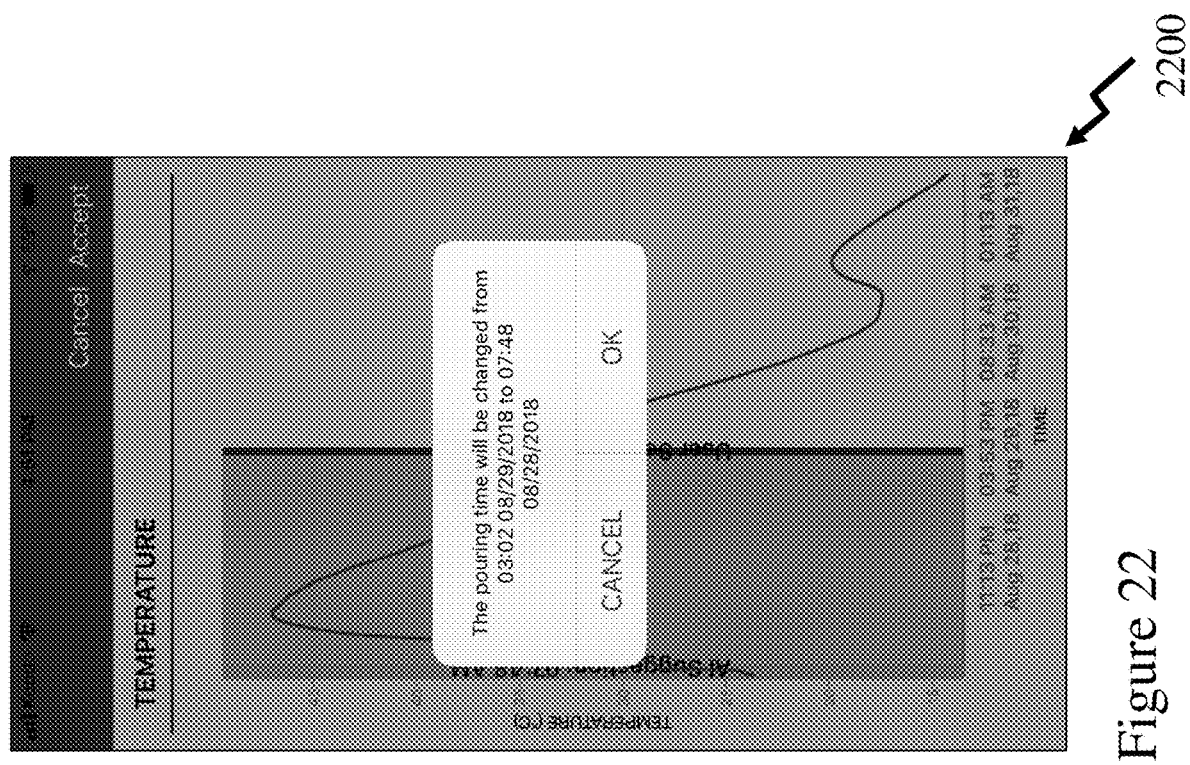

The algorithm runs over the data acquired by the sensor in order to find temperature-time behavior with features that are characteristic of concrete pouring. The algorithm having identified a region of the temperature-time data which may comprises a feature it establishes a first time point 1920 prior to the portion which may comprise a feature and a second time point 1930 after the portion which may comprise the feature. The algorithm then processes the temperature-time data between the first time point 1920 and second time point 1930 to identify if the feature is present and then establishes the time relating to the feature. If the features are found, the concrete pouring time is identified and displayed to the user, such as displayed within FIG. 20 with exemplary first screenshot 2000 of a graphical user interface for an application presenting pouring time information to a user. As depicted in FIG. 20 the user is presented with a time and date "07:48 Aug 28" for a specific sensor "3 m bottom flushed" and the option to review this or cancel.

Figure 21:
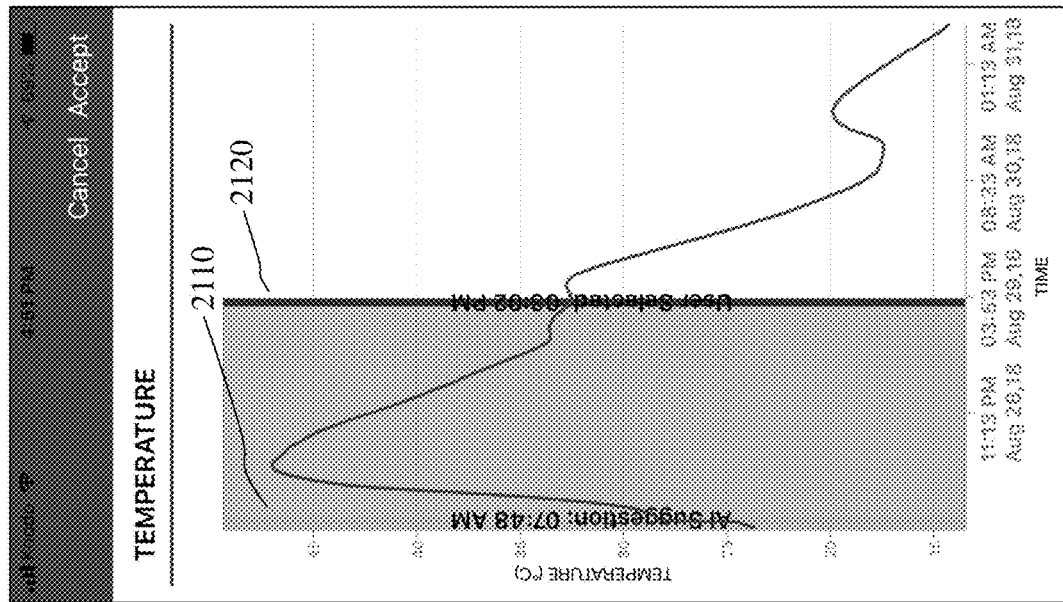
FIGS. 20 to 22 depict exemplary graphical user interfaces for an application presenting pouring time information to a user.

If the user selects "OK" then they are presented with second screenshot 2100, FIG. 21, which displays the acquired temperature versus time data from the sensor together with indicators relating to the algorithm determined pouring time 2210 and a user entered pouring time 2220. In this instance the user entered pouring time 2220 is 3:02 pm whereas the algorithm determined pouring time 2210 is 07:48 am. Accordingly, this algorithm serves to not only allow for correction of entries where the user input the wrong time, but it also saves time for the user since they can rely on the algorithm in cases where hundreds of sensors are associated with a single structure and in which every sensor has a different pouring time. Accordingly, in third screenshot 2200 in FIG. 22 the user is able to change the pouring time from a manually entered value to that determined by the algorithm. Within other embodiments of the invention the algorithm may be established to automatically determine pour time and may be executed either upon a device associated with a user, upon a remote server associated with a manufacturer of the sensor wherein data from the sensor is pushed to the cloud, etc.

Embedded Log Sensor

Tracking the history of a material, such as concrete, placed at a certain location is currently not possible. This is further complicated by the fact that over the years and decades that a concrete member/element exists that multiple companies may be associated with it and acquiring data relating to it and these may, for a variety of reasons, such as electronic hardware failures, bankruptcy, physical disasters etc. not have access to the information. Nor, generally, will a subsequent enterprise associated with a concrete member/element know all companies who have established data relating to the concrete member/element or were associated with the member/element even if they acquired no data. Accordingly, it would be beneficial to provide a system in which such tracking is possible which then becomes helpful to several stakeholders/owners and governmental bodies, for example. There is no method that exists in which a concrete member/element can be traced back to its concrete producer or the contractor that cast it or the repairs that happened to it through time except for paper trails and the like which require knowledge of each activity undertaken on a structure over its lifetime. But even these approaches suffer limitations where data is lost, activities not logged, etc.

Accordingly, the inventors have established within this concept, a low-cost sensor which is embedded within the concrete member/element and receives data from several users (e.g. concrete producers, contractors, engineers, site personnel, inspectors, etc.) regarding the concrete member/element properties and performance. The sensor also establishes a unique identifier. The sensor interacts with the user, or the cloud, through one or more wireless communication standards and receives data that is communicated to a cloud system that saves the data. This data may be concrete batch data, data acquired by other sensors relating to the concrete member/element, physical data relating to the concrete member/element, in-situ measurements, ex-situ measurements etc.

The sensor employs a battery that lasts as long as a projected lifetime for the structure with a margin to allow for delayed replacement etc. In this scenario, the sensor operates at a low power mode until activated by a wireless user request. Alternatively, the sensor can be charged through piezoelectric materials concepts or through connection to an external power supply. The sensor saves, and backs up through the cloud, data that is inputted by the user or collected by the sensor on the concrete properties throughout time. Accordingly, a range of users may input data to the sensor which subsequently uploads the data to the cloud such that it can be made available to several stakeholders throughout time (e.g. personnel doing inspection tens of years after concrete casting). Optionally, the sensor may also be provided with unique location data acquired for example from a beacon based location system such as described by the inventors.

The sensor may also track every user that connects to it, receives data from it, shares/receives shared data, reads the QR code on its body (by associating wirelessly to any local device), etc. This allows a detection of the different stakeholders and the establishment of for instance the owner of the structure, the contractor, the concrete producer, etc. It also establishes and saves the time-frame in which the structure was built, the properties of the concrete used. Accordingly, such embedded sensors may acquire a full history of the concrete member/element as well as a chain of responsibility can be established and securely stored for subsequent access at a later time. Optionally, the data being uploaded to the cloud may also be locally stored by the sensor. It would be evident that in the event of an occurrence with respect to the concrete member/element that this data may be used in disaster assessments, preventative maintenance assessments, failure analysis, litigation issues, or in tracing back the history of this concrete member/element.

Optionally, as noted above the wireless sensor may seek to automatically connect with any wireless device in its vicinity to associate them to the history it acquires. Alternatively, the sensor may contain one or more light sensors to determine whether it is in the open air rather than embedded within a material, detects either the flash of a camera or detect a visible or near-infrared machine readable scanner. In this instance, the sensor may associate with a local device comprising the scanner and/or camera to establish an identity or the sensor may include a CCD camera or alike to acquire an image above the sensor. Optionally, the sensor may contain a near-field transceiver to read a near-field enabled tag placed near it, e.g. a user's identity badge, etc. Alternatively, the sensor may contain a transceiver for reading a radio frequency identification (RFID) tag.

Ad-Hoc Embedded Sensor Networks

Amongst the limitations of embedded concrete sensors is that a user should be available on-site in order to connect to the sensor and access its data. However, the inventors have established sensors with the ability to force ad-hoc networks and identify whether one or more of the sensors is within wireless communication to a wireless gateway/hub. This gateway/hub allows data to be backed-up to the cloud such that a user can access this data from the cloud rather than having to be on-site. Accordingly, sensors according to embodiments of the invention can communicate with each other through a first wireless protocol allowing them to communicate with each other, share their data, etc. Accordingly, if a sensor according to an embodiment of the invention establishes communications to a wireless gateway/hub via a second wireless protocol wherein the wireless gateway/hub is connected to a cellular network, for example, allowing the gateway/hub to upload data acquired from the ad-hoc network of sensors to a remote server or remote cloud storage. This allows the gateway to access sensors at a further distance. For example, consider a gateway having a reach of approximately 30 meters or less (100 ft or less). However, when there are several sensors at distances of 30 meters or less (100 ft or less) from each other, the gateway only communicates with the nearest one, and then the nearest one communicates with the ones nearest to it, and the chain continues. This allows sensors at very large distances from the gateway to be communicated to and their data uploaded.

Within embodiments of the invention the first wireless protocol with which sensors communicate to one another may be ultrasound based, acoustic based, low frequency electrical based through a metallic infrastructure of the structure (e.g. rebar).

Iterative Compressive Strength Determination

In order to estimate concrete compressive strength through the maturity method, the temperature history of a certain concrete mixture needs to be monitored and the compressive strength needs to be determined at several points in time. The maturity index (which is basically the area under the temperature-time curve) is correlated to the concrete strength using functions such as that in Equation (1) where a and b are empirical constants and M is the maturity index.

$$\text{Strength} = a + b \cdot \log(M) \tag{1}$$

Through knowledge a and b which are acquired by determining both the strength and the maturity index at different points in time, the concrete strength can be estimated on-site by monitoring the concrete temperature throughout time and determining the maturity index; which is then used in Equation (1) to determine concrete strength. The process of establishing a maturity calibration however is relatively time-consuming, requires several concrete samples be taken and processed and needs to be done ahead of time. This is the main barrier facing large-scale implementation. Accordingly, in order to facilitate establishing this calibration generally on any deployment it needs to be done on-site during concrete casting.

The inventors have established an innovative concept which relates to a process in which two strength data points and the two corresponding maturity indices are determined at two different points of time. These points are typically determined at an early-age after deployment, e.g. the second day and third day after deployment for example). These points are then fitted using the maturity function to determine a and b. After a and b are determined, the maturity function is used to determine concrete strength at a third point in time and the difference between the actual and predicted strength is determined. This is used to refine the maturity function to fit the third point which increases the confidence in the calibration procedure. This iterative process is repeated several times until the confidence in the maturity function reaches a predetermined threshold, for example, at least 90% or any other chosen value. Accordingly, the maturity function is not determined ahead of time but whilst the project is in progress. This also ensures that the calibration is done for the same concrete which is actually poured rather than a sample taken from the batch prior to pouring, shot blasting etc. and performing the calibration on a similar batch in the laboratory.

It would be evident that with a sensor capable of taking measurements at a relatively high frequency, e.g. every hour, every few minutes, every minute, every few seconds, every second etc. that the process can perform a large number of iterations within a relatively short period of time. Further, where multiple sensors communicate with a local gateway, with each other or to a cloud/remote device it would be evident that the estimations from multiple sensors associated with the same pour (defined by a time frame established by the sensor manufacturer, concrete deployment enterprise, etc.).

Concrete Marketplace

Figure 23:
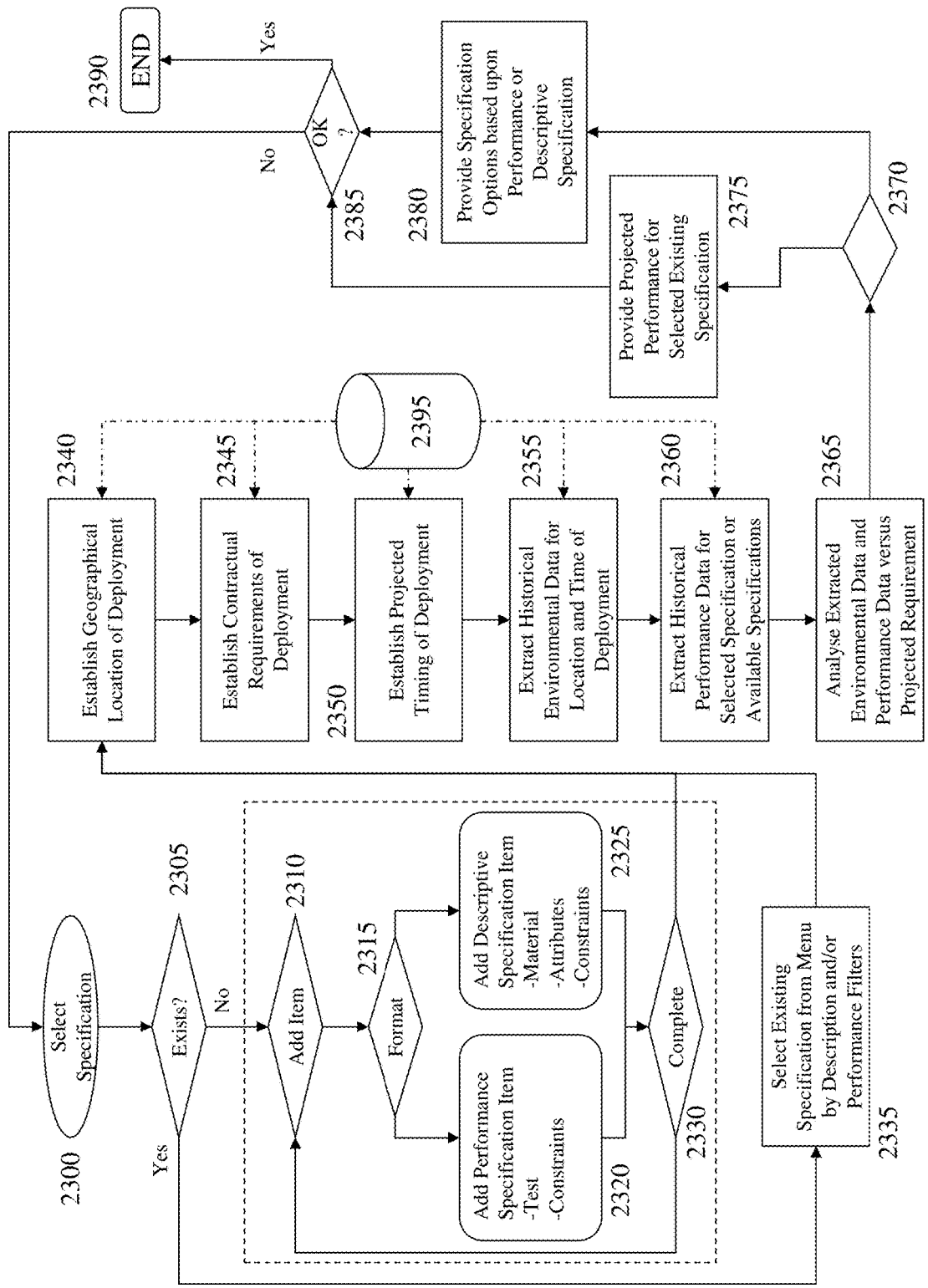
FIG. 23 depicts an exemplary process flow for the verification and/or specification of a construction material manufacturing composition based upon acquired material performance data from previous deployments acquired using sensors according to embodiments of the invention.

In order to purchase concrete, the typical prior art method is through a phone inquiry to a ready-mix concrete producer. The producer receives information from the user on the desired properties (e.g. 3-day strength or a slump/flowability criteria) and chooses a mixture that best-matches these properties. The purchaser typically only performs a few inquiries and may not reach the best option in terms of cost or performance. This can be solved using an online "market place" for concrete wherein the purchaser enters extended data to their application, deployment scenario etc. Accordingly, a purchaser may exploit an exemplary process flow such as depicted in FIG. 23 for the establishment of a manufacturing specification in respect of a construction material, such as concrete for example, exploiting acquired performance data from SMAKs and/or other performance monitoring sensors. Accordingly, the process as depicted comprises steps 2300 to 2390 in conjunction with a database 2395.

Step 2300 wherein the user initiates the process for selecting a material specification.

Step 2305 wherein a determination is made as to whether the specification already exists or not, wherein if the specification exists the process proceeds to step 2335 otherwise it proceeds to step 2310.

Steps 2310 to 2330 wherein the process of construction of a particular material specification containing a number of items is presented. Upon addition of an item through steps 2310 to 2325 the process determines in step 2310 whether the specification is complete or not and proceeds to step 2340 upon completion or step 2310 if not. Within some embodiments of the invention the determination of whether the completion has occurred is based upon selecting a number of items until a total number items desired is achieved. Optionally, the determination is made by the user or through a combination of the process and user. For example, the user may be guided to choose a base material (e.g. type of cement), a number of additives in predetermined classes of additive (e.g. aggregate, admixture, etc.) wherein selection of at least one in each as the process moves sequentially from one to another class would mean completion of the specification. Accordingly, the process will loop until the appropriate number of specification items are defined and/or the user denotes completion.

An initial decision is made in step 2315 as to whether the specification item to be created will be descriptively based or performance-based. A descriptive specification item may reference a specific material or materials and the materials attributes and/or constraints while a performance-based specification item would be established through the physical and/or chemical characteristics of the construction material either after completion of production or upon installation and thereafter. Accordingly, these are performed in steps 2320 and 2325. In this manner the construction material may be specified in terms of final target performance rather than by specific brand, identity and/or composition. Within this series of steps 2310 to 2330 the user may also establish one or more quantifiable properties and/or standard tests and may include predetermined dependent variables and/or constraints of which the construction material must satisfy. These would typically be provided to the user from a database such as database 2395. Where the specification items are listed descriptively then the item may include the material and its material quantifiable property or properties such as water/cement ratio, a set of material attributes, and/or constraints which the materials should fall within.

Once defined, either descriptively or by performance, the specification item is preferably complete and added to the concrete specification being built. The list of completed specification items may be compared to the total number of items that are to be defined for the current specification and if all of the items have not been completed, the next specification item should be defined. Each additional item can be either descriptive or performance-based again and a concrete specification may therefore contain a mix of both descriptive and performance-based specification items. Once all of the items for a particular concrete specification have been properly defined and constrained the specification is stored.

Step 2335 wherein if the decision in step 2305 was to select an existing specification then the user proceeds to make the selection from a menu using description and/or performance filters, for example.

Step 2340 wherein upon selection of the established specification or completion of the new specification the process establishes the geographical location for the deployment of the construction material. This may, for example, be by user entry or alternatively through means such as association of the construction material specification to a project wherein the data for the project includes this and other information as required including, but not limited to, that in steps 2345 to 2360. Alternatively, the user's location may be established in dependence upon an electronic address, e.g. an Internet Protocol Address, and hostname in a manner similar to that employed in geo-targeting advertisements to users upon PEDs and/or FEDs.

Step 2345 wherein the contractual requirements associated with the deployment are established. These may, for example, be a restriction on how long formwork can be left up after construction material is poured, how much material is required, time limits for delivery and pouring as the location may be within a busy downtown core, an issue from another aspect of the project etc.

Step 2350 wherein projected timing of the project is established such as when formwork will be established, when pouring should be started, when pouring should be complete, etc. are extracted from the database 2395

Step 2355 wherein historical data relating to the location and the projected time of deployment are extracted from the database 2395.

Step 2360 wherein historical performance data for the selected specification or available specifications based upon the performance and/or descriptive specification items is extracted from the database 2395.

Step 2365 wherein the extracted historical data relating to location, time, historical environmental data, historical performance data etc. are processed to establish a projected set of construction material characteristics at one or more predetermined points in time.

Step 2370 wherein the process determines whether the user selected an existing specification and proceeds to step 2375 or provided specification options and proceeds to step 2380.

Step 2375 wherein the user is provided with projected performance of the selected existing specification based upon the location, time, historical environmental data, historical performance data etc.

Step 2380 wherein the user is provided with specification options based upon the target characteristics defined by the performance and/or specification items selected by the user being matched against the available construction material specifications based upon the location, time, historical environmental data, historical performance data etc.

Step 2385 wherein the user determines whether to stop the process wherein the process proceeds to step 2390 or to iterate and the process returns to step 2300. Optionally, in the subsequent iterations the user may be provided with options to adjust the project related data such as whether a deployment is undertaken earlier or later, whether an additive should be employed, etc.

Optionally, the process automatically performs the determination in step 2385 based upon the projected performance meeting the required performance requirements. Optionally, the process may extract the target performance specification items from the database 2395 based upon selection of the project by the user within another process step and therein perform a construction material selection automatically.

Figure 24:
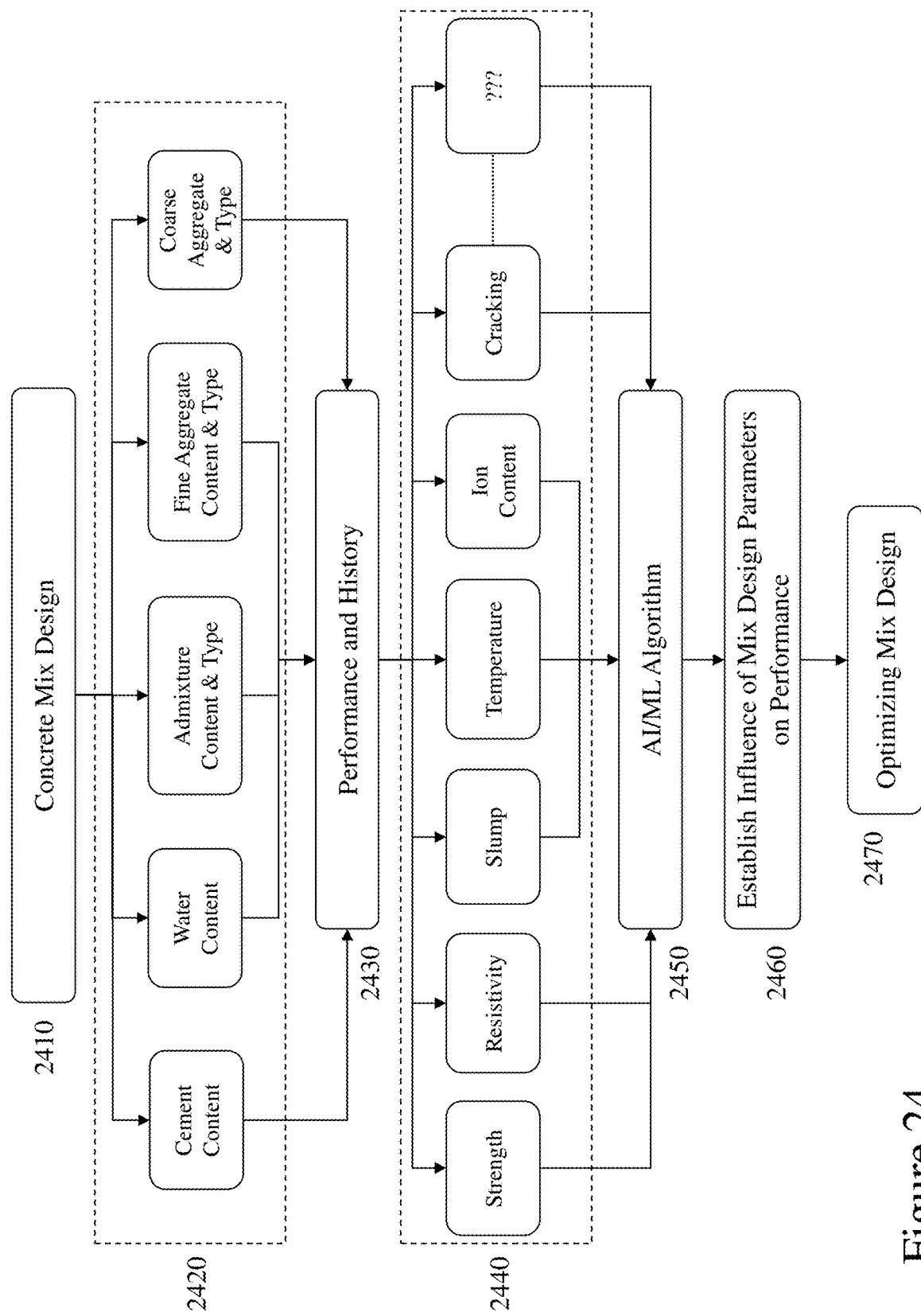
FIG. 24 depicts an exemplary process flow for optimizing a manufacturing specification for a construction material according to an embodiment of the invention exploiting machine learning and artificial intelligence.

It would also be evident that the acquisition of data relating to multiple construction materials, e.g. a concrete mix, also allows for optimization of a concrete mix as a discrete process for a manufacturer as opposed to the determination of a mix design for a specific project as described and depicted in FIG. 24. Such an exemplary process flow is depicted in FIG. 24 for optimizing a manufacturing specification for a construction material according to an embodiment of the invention exploiting machine learning and artificial intelligence comprising first to seventh blocks 2410 to 2470 respectively, these being:

First block 2410 wherein a user can select a concrete mix design;

Second block 2420 wherein the concrete mix elements are established such as cement content, water content, admixture content and type, fine aggregate content and type, and coarse aggregate content and type;

Third block 2430; wherein the performance data and history for the selected mix are extracted from the stored data within the remote servers which can comprise the data acquired from embedded sensors, partially embedded sensors, third-party sources such as environmental data etc., as well as data established at the time of concrete mix production and transportation;

Fourth block 2440 wherein the extracted performance data and history are analysed to extract different properties of the concrete such as strength, resistivity, slump, temperature, ion content, cracking etc.

Fifth block 2450 wherein artificial intelligence (AI)/machine learning (ML) algorithms and/or processes are employed to process the extracted data;

Sixth block 2460 wherein the analysis performed by the AI/ML algorithms is assessed to establish the influence of mix design parameters on the performance of the concrete mix as variations in mix preparation, mix transportation, deployment, life cycle etc. can be determined and/or evaluated; and Seventh block 2470 wherein amendments to the concrete mix can be determined to optimize the mix such as for improved long term strength, reduced chloride ions, reduced time before formwork removal, reduced impact of ambient environment etc.

The process described and depicted in respect of FIG. 24 may be fully automated or it may require user input such as identification of which aspects of performance of the mix are to be assessed/optimized. Further, the analysis may be filtered such as for geographic location, season, type of infrastructure element, etc.

Figure 25:
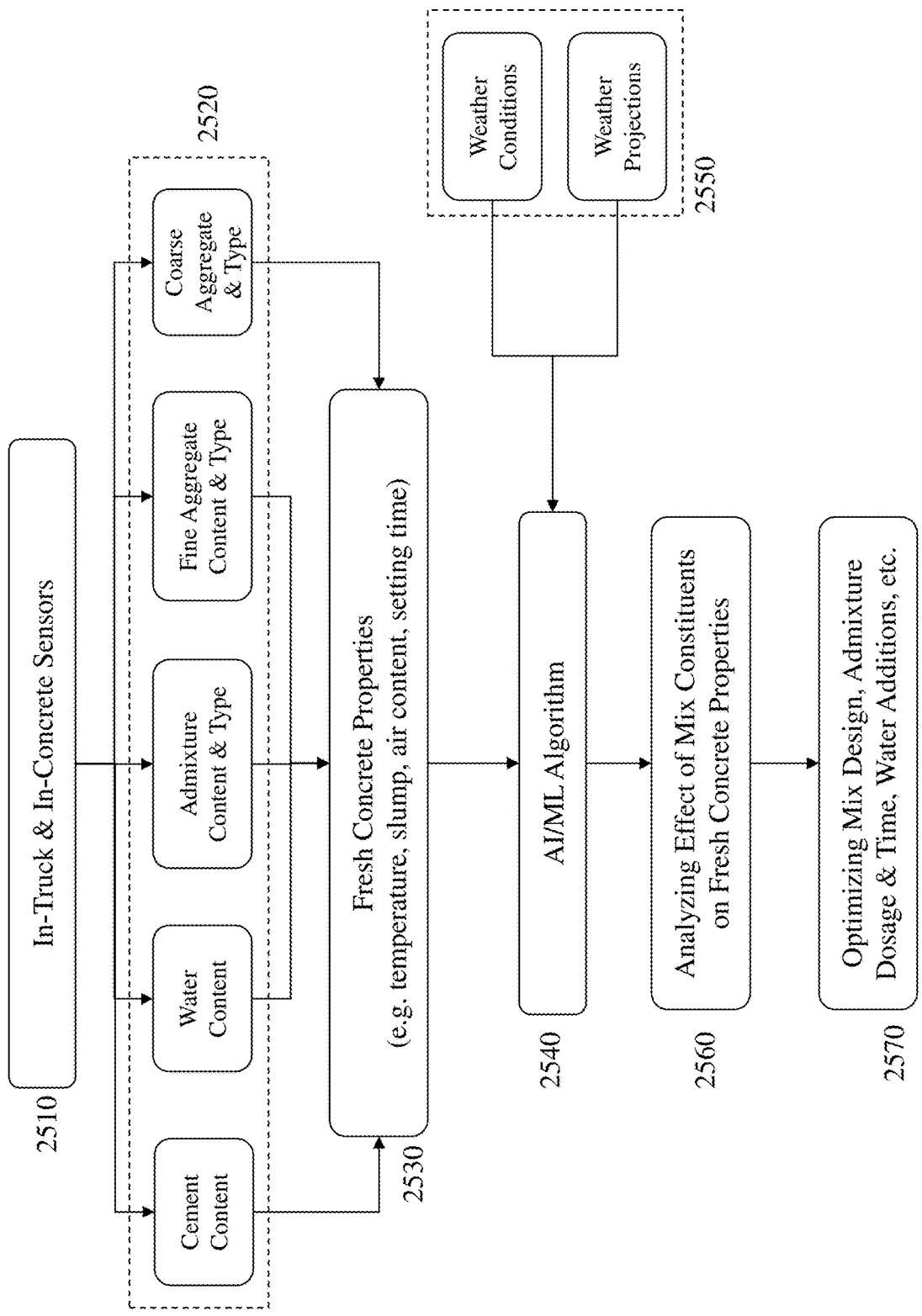
FIG. 25 depicts an exemplary process flow for optimizing a construction material during transportation according to an embodiment of the invention exploiting machine learning and artificial intelligence.

Optionally, a variant process may be implemented such as depicted in FIG. 25 wherein analysis is performed in respect of transportation of the construction material, e.g. concrete mix. In many concrete mix designs and deployments one or more admixtures are added to the concrete. These may be added at various points including, but not limited to, concrete batching, in truck, during deployment, and after deployment. Accordingly, FIG. 25 depicts an exemplary process for assessing admixtures, water etc. both in terms of which to add to the construction material based upon acquired historical data relating to their addition, delivery, performance etc. also determine when to add a particular admixture to a construction material batch and the quantity to add. For example, the analysis may determine that an admixture improving the low temperature pouring characteristics and initial curing of concrete is best added thirty minutes prior to pouring. Further, as this may be problematic for some or all deliveries the admixture(s) may be preloaded into one or more dispensers which are automatically triggered based upon downloading of a program to the concrete truck from the database for a specific delivery batch. In this manner, the admixture(s) are automatically added rather than when the truck driver can stop and add them. Equally, such analysis may determine that a batch having been loaded for two hours reaches a point where subsequent deployment will result in reduced performance or that the current projected environmental conditions will require all loads to be poured within a predetermined period of time if the concrete is required as a single contiguous block rather than multiple layers as a second pour is made upon a curing previous pour etc.

Accordingly, the exemplary process flow comprises first to seventh blocks 2510 to 2570 respectively, these being:

First block 2510 wherein data acquired from in-truck and in-concrete sensors such as described above is collected and stored within the one or more remote servers storing information relating to the sensors as well as that established from concrete batch manufacturing plants, sensors embedded within the infrastructure elements, semi-embedded sensors associate with infrastructure elements, etc.;

Second block 2520 wherein data relating to the mix transported for which data exists at the various points such as batching, truck loading, pouring, curing, ongoing life cycle monitoring etc. are retrieved and associated with the in-truck and in-concrete sensor data;

Third block 2530 wherein the fresh concrete properties such as temperature, slump, air content, setting time etc. are retrieved and associated with the data existing at the various points such as batching, truck loading, pouring, curing, ongoing life cycle monitoring etc. are retrieved and associated with the in-truck and in-concrete sensor data;

Fourth block 2540 wherein a plurality of artificial intelligence (AI)/machine learning (ML) algorithms and/or processes are employed upon the data in conjunction with data from other sources such as weather conditions and weather projections extracted from fifth block 2550;

Sixth block 2560 wherein the analysed effects of the mix constituents on the fresh concrete properties are established against the fresh concrete properties; and Seventh block 2570 wherein optimizations of the mix design, admixture dosage and time, water additions etc. are established.

Each of the exemplary processes described and depicted above exploits the acquisition of data from embedded sensors within the infrastructure.

Accordingly, the specifications within a database such as that employed in respect of FIG. 23 are those provided by one or more producers. Accordingly, the database includes mixture performance characteristics which may include: flowability/slump, strength versus time, air content, permeability, chloride diffusivity characteristics, etc. This database works as the back-end of a website to which a purchaser logs in to access. Optionally, website may be associated with a subscription service provided by one or more of the concrete producers, a sensor manufacturer, an industry organization, a regulatory authority etc. The purchaser enters as described in steps 2310 to 2330 several characteristics of the concrete required (such as a target strength of x at y days). The characteristics are matched to the database and several mixtures are identified. Then as described within steps 2340 to 2365 the identified mixes are then employed to refine the selection(s) in dependence upon the environmental, geographical factors etc. Accordingly, a mix may be rejected as the projected environmental conditions preclude it whilst another mix may be preferred.

Whilst the process flow depicted in FIG. 23 simply terminates after the user selects to end it based upon their being provided either in step 2375, with projected performance of the selected existing specification based upon the location, time, historical environmental data, historical performance data etc., or in step 2380, with specification options based upon the target characteristics defined by the performance and/or specification items selected by the user being matched against the available construction material specifications based upon the location, time, historical environmental data, historical performance data etc., where the process flow forms part of an online marketplace then the user upon determining a mixture is provided with the means to communicate to a producer through one or more means, such as electronic mail, electronic messaging, phone, website etc. Within embodiments of the invention accessing the website and subsequent steps of purchasing etc. may be integrated into project planning tools, supply chain management tools etc.

Artificial Intelligence/Machine Learning in Material Life Cycle

As discussed above in respect of FIG. 23 in step 2360 historical performance data from sensors is extracted for a selected specification or available specification. Further, as discussed above in FIG. 24 a process flow for optimizing a manufacturing specification for a construction material according to an embodiment of the invention exploiting machine learning and artificial intelligence is presented. Also, as discussed above in respect of FIG. 25 an exemplary process for assessing admixtures, water etc. both in terms of which to add to the construction material based upon acquired historical data relating to their addition, delivery, performance etc. is described as well as determining when to add a particular admixture to a construction material batch and the quantity to add.

Accordingly, with the increasing use and deployment of sensors a substantial volume of data is collected and is poorly utilized. Further, a large volume of data collected throughout the service-life of concrete, from batching until demolition, is poorly utilized in the process of concrete design and specification. It is generally understood that several factors can affect the performance of concrete, including, but not limited to, mixture constituents, mixture constituent proportions, cement chemical composition, raw materials source, ambient conditions, distance from plant to site/traffic conditions, etc. Most of these pieces of information are known to concrete producers, while the concrete performance is measured on-site using quality assurance/quality control (QA/QC) methods using embedded sensors or well-established test methods (such as the slump test to determine concrete flowability). Although concrete producers may perform simple statistical analyses to detect anomalies for instance, this data is not combined and analyzed in a streamlined manner in order to, for example, predict concrete strength from mixture composition and ambient conditions. Due to the number of variables in this system and due to the complexity of establishing models to provide such estimates, the method of designing concrete mixtures has been largely based on experience, i.e. what worked for the last similar project will work for this one. This generally leads to losses in materials, energy and time due to the overly conservative choices as well as failure to identify anomalies, issues etc.

Accordingly, the inventors have established that it would be beneficial to provide a platform which provides:
- centralised acquisition and storage of data collected from concrete producers regarding concrete mixture composition, cement chemical composition, raw materials type and source;
- centralised acquisition and storage of data collected from embedded sensors, such as strength and temperature;
- centralised acquisition and storage of QA/QC data collected from tests done on-site (such as slump/flowability); and
- centralised acquisition and storage of data collected such as GPS location of concrete truck, GPS location of plant and jobsite and ambient humidity and temperature conditions.

Accordingly, this data is analyzed using machine learning algorithms in order to predict one or more factors, including, but not limited to:
- concrete performance (such as strength, flowability, etc.);
- perform mix optimization (to meet QA/QC results at a lower cost);
- detect anomalies; and
- project concrete deterioration.

An exemplary system according to an embodiment of the invention is composed of several components that are used for data collection and processing. These components comprising:
- sensors that are used for data-collection on site where the acquired data may include, nit not be limited to, concrete temperature, concrete humidity, concrete strength and sensor location;
- a cloud platform component that collects and combines the data from the sensors;
- a cloud platform component that collects data from the user on the concrete mixture design and QA/QC results;
- a cloud platform that collects data on the surrounding conditions such as ambient (current and forecasted) temperature and humidity as well as traffic and location;
- machine learning algorithm(s) that combine all of the collected data and perform algorithm training on the dataset(s); and
- a cloud platform that receives data from the user, inputs it into the machine learning algorithm and displays predictions of compressive strength, slump, air content, temperature, permeability and other concrete properties and/or QA/QC results as would be readily understood by a person having ordinary skill in the art.

The collected data is divided, for example, into independent and dependent variables. The dependent variables include, but are not limited to:
- mixture constituents' volumetric proportions;
- cement chemical composition;
- sand/gravel type and mineralogy;
- chemical admixtures type and content;
- current and projected ambient humidity and temperature;
- concrete production, transition and placement conditions on construction jobsite; and
- cost.

The independent variables include, but are not limited to:
- strength;
- workability;
- air content; and
- permeability.

The acquired data is collected and fed into one or more artificial neural network algorithms that determines correlations between the dependent and independent variables, in a process termed algorithm training. After performing training, the one or more artificial neural network algorithms are able to determine the concrete performance (dependent variables) through a knowledge of the mixture characteristics and external conditions (independent variables). Whilst the inventors describe embodiments exploiting artificial neural networks it would be evident that other approaches may be employed including, but not be limited to, decision trees, random forests, support vector machines, etc.

Within embodiments of the invention the one or more artificial neural network algorithms may also determine a required mixture recipe (independent variables) to achieve some QA criteria (dependent variables).

Within embodiments of the invention the one or more artificial neural network algorithms may also allow for detection of anomalies in one or more aspects of the manufacturing, transport, deployment, use life-cycle as well as provide guidance to the user on best-practices for their mixes using the historical data.

Artificial Intelligence Mix Verification and Mix Optimization

Within embodiments of the invention described above in respect of FIGS. 23 to 25 different methodologies with respect to exploiting machine learning and artificial intelligence for:

- verification and/or specification of a construction material manufacturing composition based upon acquired material performance data from previous deployments acquired using sensors according to embodiments of the invention;
- optimizing a manufacturing specification for a construction material; and
- optimizing a construction material during transportation.

Within other embodiments of the invention machine learning and artificial intelligence may be employed to adjust a construction material for cost reduction and/or waste reduction. As described above and below in respect of SMAKs according to embodiments of the invention may be deployed within a construction material wherein the data they acquire relating to the construction material which is subsequently extracted and/or transmitted to a remote cloud based database. Such a cloud database may also obtain other data such as concrete mixture proportions either directly through user inputs, transfers from other databases such as those associated with the construction material supplier for example, or data acquired from the embedded sensors which had the construction material data stored within them. This additional data may also include a target strength which may be similarly input by an end user, such as an engineer, designer or specifier associated with the project to which deployment of the construction material relates or by the construction material manufacturer. As described with respect to SMAKs and databases within embodiments of the invention the construction material strength may be established via a method such as the maturity method either by algorithms in execution upon the SMAKs themselves or the remote cloud infrastructure.

Accordingly, within an embodiment of the invention such as described herein or below with respect to FIG. 28 the construction material strength, predicted and/or actual, may be compared with the target strength. Where the actual strength is below the target strength by a predetermined percentage or amount then it has been described that an alarm or communication may be triggered indicating an issue with the construction material. However, where the actual strength differs from the target strength but is higher then such an alarm is not triggered as the construction material strength exceeds the design strength or target strength. However, within an embodiment of the invention where the actual strength exceeds the target strength by a predetermined percentage or amount then a user notification may be triggered to a user or users indicating, for example, "Potential exists for mixture optimization and cement savings."

Accordingly, within an embodiment of the invention a machine learning algorithm or artificial learning algorithm may be employed, such as a multi-layer perceptron algorithm, which is trained on the historical strength data and construction material mixture proportion/composition data may be triggered/employed to calculate a percentage savings in cement, for example where the construction material is concrete, in order to reduce the construction material strength so that meets the specified target strength. Accordingly, a variance process is performed predicting strength for the same mixture proportions but for varying contents of the construction materials, e.g. cement for concrete. The content versus strength is used to calculate the percent decrease in the element of the content desired to allow the construction material to meet the design strength with minimal waste and/or cost. Accordingly, the variance analysis may assess those elements within the material composition having the highest cost. Subsequently, following these adjustments and realization of the savings, the strength is again monitored for further new cases of deployment of the construction material pouring, using the modified mixture, in order to compare the percentage saving and strength suggested by the algorithm with the actual savings achieved. This subsequent analysis may be employed for further algorithm training, e.g. further determination of weights in the multi-layer perceptron model where this is employed, allowing such suggestions to increase in accuracy and value as time proceeds.

Within embodiments of the invention this process may be executed prior to the construction material reaching its target strength using mathematical fitting of the temperature versus time data, for example, together with knowledge of the location and/or ambient weather forecast. Accordingly, embodiments of the invention exploit early predictions of concrete strength and therefore provide early suggestions of cement savings. For example, an initial concrete pour of foundations and/or lower levels of a building may provide sufficient data and early prediction that subsequent concrete pours employ adjust material compositions. Within another embodiment of the invention the target may be to achieve a minimum strength within a predetermined period of time in order to allow for increased speed of construction. Accordingly, the "cost" of a material composition may be established, for example, in terms of overall cost, material excess to that required to meet threshold performance (e.g. wasted cost/material), cost of project duration, etc.

Figure 28:
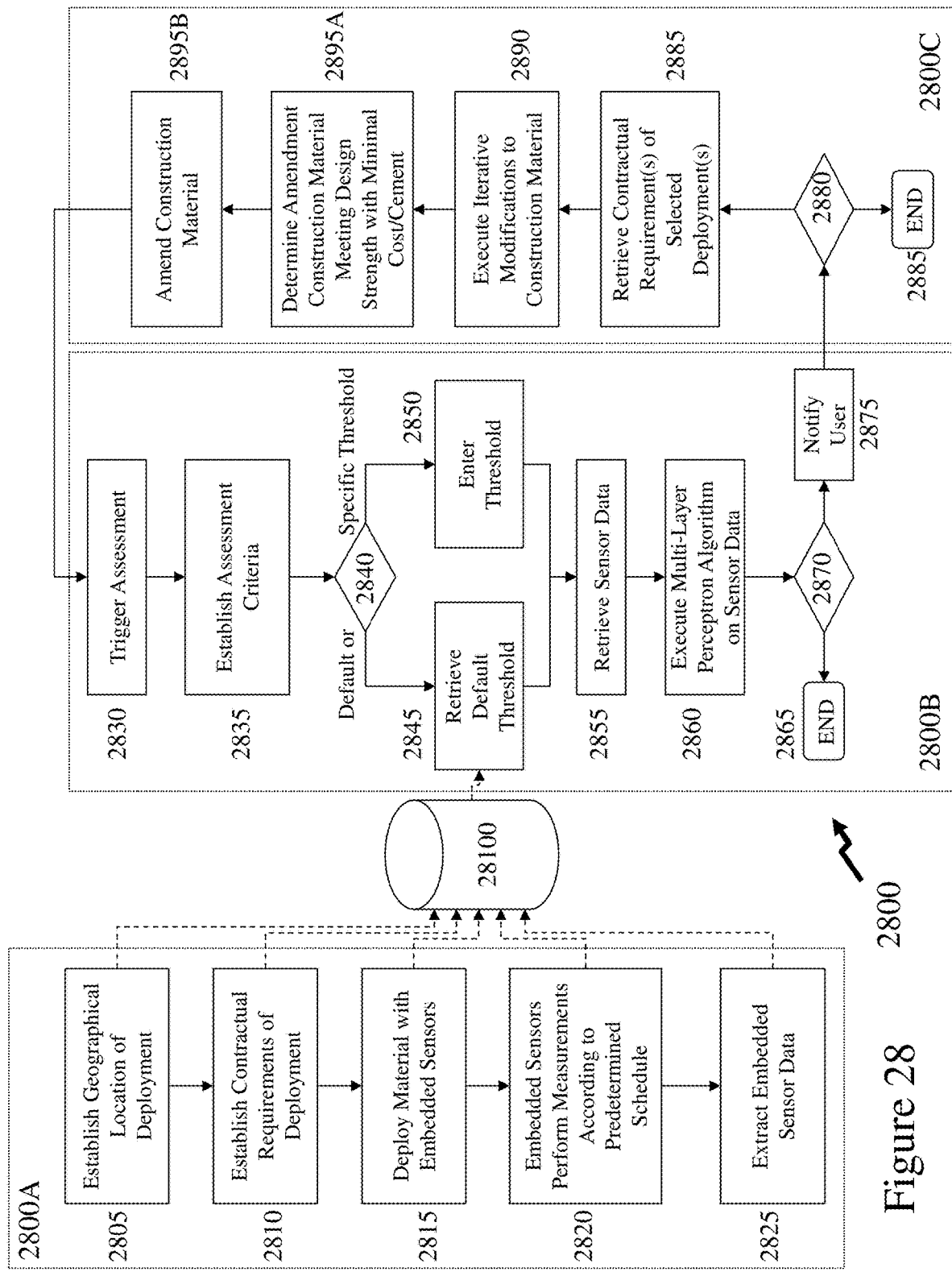
FIG. 28 depicts an exemplary process flow for optimizing a construction material for reduced cost/waste based upon embedded sensor data exploiting machine learning and artificial intelligence.

Referring to FIG. 28 there is depicted an exemplary process flow 2800 for optimizing a construction material for reduced cost/waste based upon embedded sensor data exploiting machine learning and artificial intelligence. As depicted the process flow 2800 comprises a first sub-flow 2800A, a second sub-flow 2800B, and a third sub-flow 2800C. Within first sub-flow 2800A there are depicted first to fifth steps 2805 to 2825 relating to the deployment of SMAKs according to embodiments of the invention together with extraction of data from these SMAKs within a construction material. Accordingly, these steps comprise:

First step 2805 wherein a geographical location of a deployment of SMAKs according to embodiments of the invention in conjunction with a construction material is established and communicated to a remove server 28100. This may be established by a designer, architect, owner of a structure being constructed, supplier of the construction material, contractor etc.

Second step 2810 wherein contractual requirements of the deployment are established and communicated to the remote server 28100. Such requirements may include, but not be limited to, the target strength of the concrete, a minimum strength at a predetermined point in time, etc. This may be established by a designer, architect, owner of a structure being constructed, supplier of the construction material, contractor etc.

Third step 2815 comprises deployment of the construction material with the embedded sensors wherein data relating to the deployment and/or SMAKs is communicated to the remote server 28100. This may be established by a supplier of the construction material, contractor etc. or it may be automatically acquired by data loggers, wireless interrogation, or wireless data acquisition for example.

Fourth step 2820 wherein the embedded sensors perform measurements according to a predetermined schedule.

Fifth step 2825 wherein the acquired data of the SMAKs and/or predicted material characteristics of a construction material is extracted. This data may be automatically acquired by data loggers, wireless interrogation, or wireless data acquisition for example and communicated to the remote server 28100.

Within second sub-flow 2800B there are depicted first to tenth steps 2830 to 2875 respectively relating to the assessment of data acquired from SMAKs according to embodiments of the invention to determine whether an opportunity for optimization exists. Accordingly, these steps comprise:

First step 2830 wherein an assessment process is triggered. This may be automatically triggered, for example based upon the remote server 28100 determining that SMAK data relating to a deployment for which contractual requirements exist has been acquired by the remote server 28100, or manually triggered by a user, e.g. a designer, an architect, a supplier of the construction material, etc.

Second step 2835 wherein the assessment criteria are established, for example, target strength or strength at a predetermined time post-deployment from which the second sub-process 2800B proceeds to third step 2940.

Third step 2940 determines whether a threshold between an achieved and/or predicted parameter versus a target for that parameter should be automatically established within the analysis of second sub-flow 2800B or be established by a user. If the determination is automatic then the second sub-flow 2800B proceeds to fourth step 2845 wherein the second sub-flow 2800B extracts the threshold from the remote server 28100 otherwise it proceeds to fifth step 2850 wherein the user enters the threshold.

Sixth step 2855 wherein the second sub-flow 2800B extracts the SMAK data for the deployment or deployments that the user wishes to analyse. These deployment or deployments may, for example, be determined specifically by user entry of them or they may be determined based upon the user selecting one or more filters including, but not limited to, a geographical region of deployment, a type of construction, a construction material, a time of year, material supplier, and production location.

Seventh step 2860 wherein the second sub-flow 2800B executes a machine learning or artificial intelligence algorithm using the extract data in sixth step 2855 together with the target material parameter(s), threshold etc.

In eighth step 2870 the second sub-flow 2800B determines whether there results of the analysis performed in sixth step 2860 indicate an optimization is available or not. If not, the process proceeds to ninth step 2865 and it and the process flow 2800 end. If an optimization is available then the process proceeds to tenth step 2875 and notifies one or more users.

Alternatively, within second step 2835 rather than target strength or strength at a predetermined point in time other measurements may be employed including, for example, a specified slump versus actual measured slump or a specified air content versus actual measured air content. These values can be added to the application/sensor/server by user-input."

Within third sub-flow 2800C there are depicted first to sixth steps 2880 to 2895B respectively relating to the optimization of a construction material based upon a determination from the second sub-flow 2800B indicates an optimization option exists. Accordingly, these steps comprise:

First step 2880 wherein a user based upon the notification of the opportunity for an optimization of the construction material may decide whether to perform the optimization or not. If the user elects not to proceed the process proceeds to second step 2885 wherein the third sub-flow 2800C and process flow 2800 end. If the user decides to perform an optimization then the process proceeds to third step 2885.

Third step 2890 wherein the third sub-flow 2800C extracts the contractual requirement(s) of the deployment(s). These may be those employed in second sub-flow 2800B or they may be those determined from a subsequent establishment process (not depicted).

Fourth step 2890 wherein the third sub-flow 2800C performs a process of iteratively assessing modifications to the construction material to determine resulting performance against the contractual requirements for the deployment or deployments being assessed.

Fifth step 2895A determines whether any of the assessed modifications/amendments to the construction material meet the contractual requirements with minimal material.

Sixth step 2895B wherein an amended construction material composition meeting the contractual requirements with minimal material is selected, either automatically or based upon user input. From sixth step 2895B in third sub-flow 2800C the process loops back to first step 2830 of second sub-flow 2800B.

The process loop feedback from sixth step 2895B in third sub-flow 2800C the process loops back to first step 2830 of second sub-flow 2800B results in the process flow 2800 performing an ongoing construction material optimization. Whilst the embodiment of the invention described within process flow 2800 relates to instances of the construction material parameter(s) exceeding the target specifications it would be evident that additional steps (not depicted for clarity) may be included which upon determination that the construction material parameter(s) do not exceed the target specifications such that the user or alternate user(s) are notified of the failure to meet target specifications. A failure may equally trigger a variant of third sub-flow 2800C wherein the construction material composition is assessed for variations which will result in the construction material exceeding the target specifications.

Formation Factor

It is known, see for example Hilhorst in "*Conductivity Sensor*" (*Soil Sci. Soc. Am. J.* 2000, 64, 1922-1925), that a linear relationship exists between the conductivity and permittivity of porous dielectric materials (e.g. concrete), with an intercept that is indicative of the material permittivity at zero conductivity. Accordingly, this relationship allows a determination of pore solution conductivity (the conductivity occupying the pore structure of concrete) at any point in time, through Equation (2) where $\sigma_p$ is the pore solution conductivity, $\sigma_b$ is the bulk material conductivity, $\varepsilon_p$ is the pore solution permittivity (which is assumed to be a constant), $\varepsilon_b$ is the bulk material permittivity and $\varepsilon(\sigma_b=0)$ is the permittivity of the material when its conductivity reaches zero. The challenge is to find $\varepsilon(\sigma_b=0)$ which is material dependent.

$$\sigma_p = \frac{\varepsilon_p \sigma_b}{\varepsilon_b - \varepsilon(\sigma_b = 0)} \quad (2)$$

If this value is determined, the pore solution conductivity can be directly determined whenever the bulk conductivity and permittivity are known. In order to determine $\varepsilon(\sigma_b=0)$ and subsequently calculate the pore solution conductivity, bulk conductivity and permittivity need to be determined at several saturation levels in order to find $\varepsilon(\sigma_b=0)$ through extrapolation (which is not generally practical in the field, especially with concrete. Using this determined value $\varepsilon(\sigma_b=0)$, whenever permittivity and conductivity are measured, Equation (2) above can be used to determine pore solution conductivity at the time the permittivity and conductivity measurements are taken.

Over time concrete hardens and develops microstructures and since the bulk conductivity and permittivity change through time due to concrete hydration, decrease in porosity, refinement of microstructure, change in pore solution conductivity, or naturally due to drying, the bulk conductivity and permittivity are naturally changing throughout time. Accordingly, by employing an embedded sensor, the bulk conductivity and permittivity can be measured at several points in time. Based upon these measurements the intercept, $\varepsilon(\sigma_b=0)$, can be determined through extrapolation of the permittivity-conductivity relationship. Once the intercept is determined then Equation (2) can be used with the measured permittivity and conductivity to determine the pore solution conductivity at any point in time. Accordingly, this can then be used to determine the formation factor.

Figure 26:
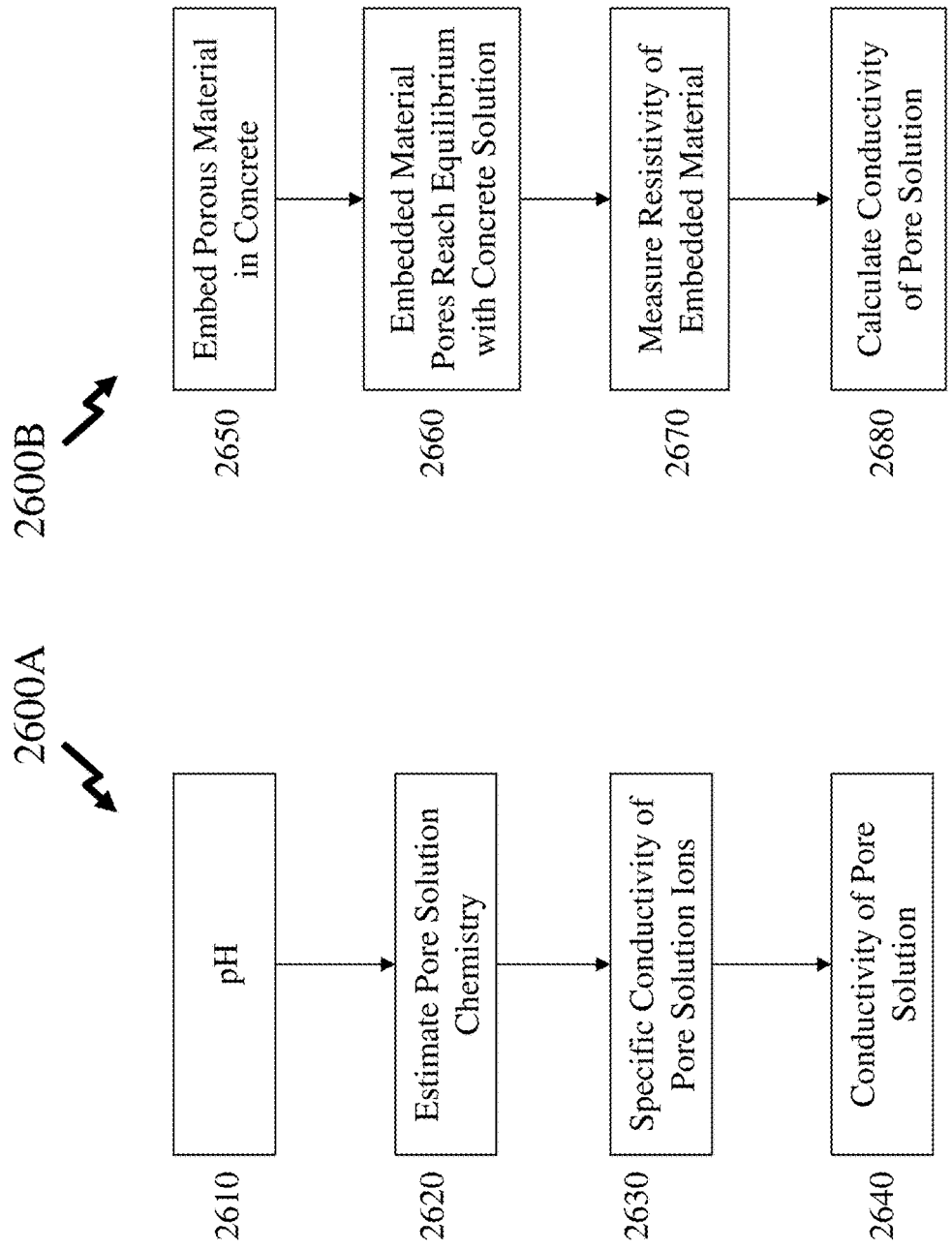
FIG. 26 depicts exemplary process flows for determining the conductivity of a solution associated with a construction material exploiting embodiments of the invention through either pH measurements or embedding a porous material forming part of a sensor within the construction material.

For example, referring to FIG. 26 there are depicted exemplary first and second process flows 2600A and 2600B respectively for determining the conductivity of a solution associated with a construction material exploiting embodiments of the invention through either pH measurements or embedding a porous material forming part of a sensor within the construction material. These employing a sensor, what the inventors refer to as SMArt roKs (SMAK) according to an embodiment of the invention. Considering the pH based route then this is depicted in first process flow 2600A comprising first to fourth steps 2610 to 2640 respectively, these being:

First step 2610 wherein the SMAK acquires a pH measurement using a pH sensor such as an ISFET for example;
Second step 2620 wherein the pore solution chemistry is estimated for the construction material either generally or in dependence upon the pH measured;
Third step 2630 wherein for the pore solution chemistry established; and
Fourth step 2640 wherein the pore solution conductivity is established.

It would be evident that steps 2620 and 2630 may have been performed previously and that step 2610 therefore in the measurement of the pH leads to establishing the pore solution conductivity in step 2640 from a lookup table, application of one or more algorithms previously established etc. As with the consideration of maturity curves etc. discussed above such lookup table(s), algorithms etc. may be stored within the SMAK allowing direct establishment of the pore solution conductivity by the SMAK which is communicated to any scanning device and therein to the cloud-based storage etc. or the raw pH value is acquired by the scanning device and the calculations performed upon it or remotely within the cloud-based application(s) associated with the acquisition, processing, and storage of data relating to SMAKs within construction materials. Alternatively, as described the pore solution chemistry and pore solution ion conductivities are established in real time either generally or specifically in dependence upon the pH.

It may be noted that the dielectric constant of the construction material is dependent upon the water content as water has a dielectric constant of 81 versus approximately 2-4 for dry concrete when measured using microwave/RF propagation also allows for measurement data relating to the pore solution conductivity where the measurements are performed below approximately 10 GHz versus those performed above this frequency. Below this frequency the loss factor of the construction material can be significantly impacted by the increase of pore solution conductivity arising from ions such as chloride for example. Whilst the ionic content of the pores does not significantly affect dielectric constant, although there is some dependence, the loss factor which causes attenuation can be changed due to the increase in ohmic conductivity. In cement mortar, both conductivity and dielectric constant increase with larger amount of chloride and sodium ions. This affect can also change with the water/cement (w/c) ratio as the impact on pore structure from chloride ions, within materials such as Portland cement based mortar, varies with w/c ratio. Accordingly, additional data relating to pore solution conductivity and pore size can be determined from the loss within a microwave/RF based dielectric constant measurement.

Now referring to second process flow 2600B a methodology based upon measuring the conductivity of the solution within the construction material is presented comprising first to fourth steps 2650 to 2680 respectively. These comprising:

First step 2650 wherein the SMAK is embedded within the construction material, e.g. concrete, as described in respect of SMAKs previously but the SMAK now includes a porous material in direct contact with the construction material;
Second step 2660 wherein the embedded porous material reaches equilibrium with the pores within the construction material;
Third step 2670 wherein for the resistivity of pore solution is measured; and
Fourth step 2680 wherein the pore solution conductivity is determined in dependence upon the resistivity.

Accordingly, if the pore solution changes then the equilibrium state with the embedded porous material will subsequently adjust such that the ongoing resistivity allows for ongoing determination in respect of changes in the pore solution of the construction material.

Figure 27:
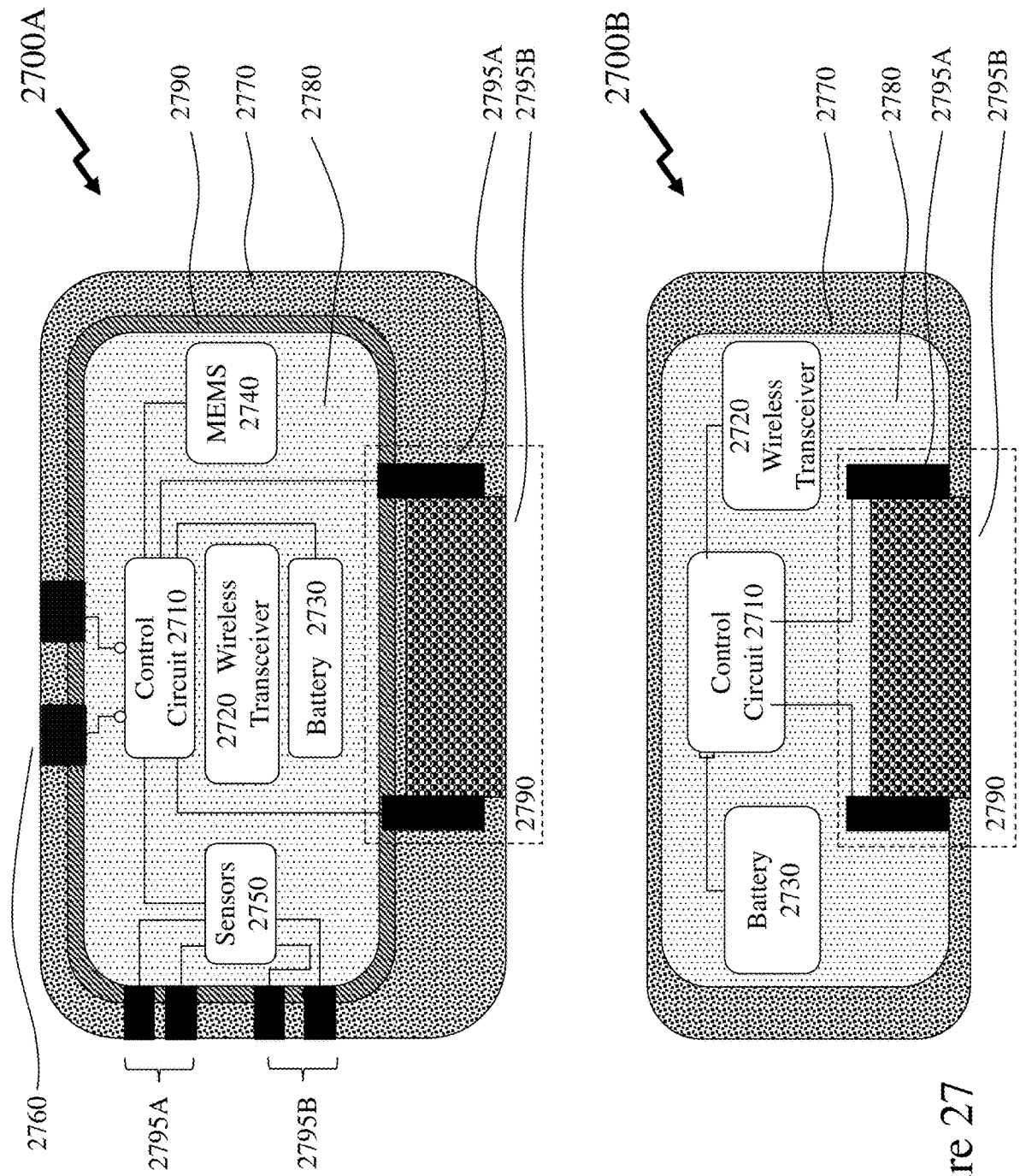
FIG. 27 depicts exemplary sensor designs according to embodiments of the invention.

Referring to FIG. 27 there are depicted exemplary SMAK designs 2700A and 2700B according to embodiments of the invention. In first SMAK design 2700A the SMAK comprises the control circuit 2710, wireless transceiver 2720, battery 2730, MEMS 2740, and sensors 2750 which are coupled to first and second SENsor INTerfaces (SENINTs) 2795A and 2795B. The control circuit 2710 is also coupled to contacts 2760 and a resistivity sensor 2790 comprising a porous material 2795B and contacts 2795A. The porous material 2795B is exposed to the external environment such that when embedded within the construction material the porous material 2795B can reach equilibrium with the solution portion of the construction material. Accordingly, the control circuit 2710 can establish resistivity measurements for the resistivity sensor 2790. As depicted the SMAK comprises an intermediate casing 2790 which encapsulates the sensor filler 2780, e.g. a foam, air, etc. and is surrounded by an outer shell 2770. As depicted the porous material 2795B is entirely external to the intermediate casing 2790 and only contacts 2795A extend through it for the resistivity sensor 2790 although other contacts 2760 and first and second SENINTs 2795A and 2795B also do.

In second SMAK design 2700B the SMAK is reduced in complexity to the control circuit 2710, wireless transceiver 2720, and battery 2730 together with the resistivity sensor 2790 comprising porous material 2795B and contacts 2795A. In this embodiment the porous material 2795B is not outside an intermediate casing and is depicted as being within both the outer shell 2770 and filler 2780 although it would be evident that according to the filler 2780 that the outer shell 2770 may be omitted.

Optionally, a SMAK comprising a porous sensor 2790 may be stored such that the porous material is sealed prior to use such as by the use of a peel-off cover or sealing the SMAK within a bag discretely or in combination with a material such as a desiccant or solution of predetermined and known composition. Optionally, a solution may be added to the porous material 2795B prior to deployment, e.g. deionized water.

Materials

Whilst within the preceding Figures the body of the sensor has not been described or depicted in detail the outer surface of the sensor may be smooth, contoured, grooved, ribbed, and/or comprise bumps and/or features. Optionally, the contours may extend further across the upper surface of the sensor or they may be limited to predetermined regions of the sensor. Optionally, the depth, spacing, and number of grooves, ribs, bumps, etc. may vary as well as their surface profile from symmetric to asymmetric etc. Optionally, the upper surface may be smooth, or it may be profiled by the distribution of features across upper surface regions in some embodiments of the invention. Optionally different regions of the sensor may have different structures such as features, grooves, smooth areas etc.

The sensor according to an embodiment of the invention may be provided in a range of physical sizes such that, for example, the length of the member inserted portion may be 12.5 mm, 15 mm, 25 mm, 35 mm, 40 mm, and 50 mm for example (0.5", 0.6", 1", 1.4", 1.6", 2", 2.5", 3", 4", 5", 6" or 8") and it's lateral/vertical dimensions may be, for example, 6.25 mm, 10 mm, 12.5 mm, 15 mm, and 25 mm for example (0.25", 0.4", 0.5", 0.6", or 1"). Whilst the sensors depicted previously in FIGS. 3 to 18 have been depicted as being principally rectangular and having an aspect ratio of approximately 3:1 it would be evident that other dimensions, aspect ratios, cross-section geometries etc. may be employed without departing from the scope of the invention.

Typically, the construction of a sensor according to an embodiment of the invention such as depicted within embodiments of the invention described in respect of FIGS. 3 to 18 employs a body comprising an upper portion and a lower portion although other embodiments of the invention may employ one or more scaffolds/resilient elements which provide rigidity to the required portions of the sensor which may be surrounded by a shell and then a casing. Whilst the casing and shell may be transparent or semi-transparent over portions or all of the sensor it is common for the sensor to be opaque. An outer casing may be coloured based upon single colour tones as well as single colour, binary colour, multiple colour etc. According to the complexity acceptable then the outer casing may be formed from a variety of colours and/or be patterned for a specific design. Typically, such colours may be part of a silicone, elastomer, or plastic employed in forming the casing although in other embodiments of the invention the casing may be coloured once formed and a protective fluid proof, non-toxic, non-abrasive coating formed atop these applied colours.

Optionally, a casing for a sensor according to an embodiment of the invention the ADDEV will be formed from a non-toxic, hypoallergenic silicone to provide a safe smooth surface although some regions of the sensor may be coated, textured and/or finished with a variation from that of the remainder of the casing in order to enhance or promote retention of the sensor against an element to which the sensor is intended to be deployed with, e.g. rebar, wooden framing, plasterboard, etc. Optionally, the outer surface of the casing will be formed to provide low friction as well as resistance to lubricants, chemicals, etc. that may or may not be employed.

Optionally, a sensor according to an embodiment of the invention may comprise an outer body or shell comprising a single chamber or a plurality of chambers and may be formed from one-piece part or multiple piece parts which are connected via the casing and/or discrete or connected by a central portion with different degrees of rigidity.

Embodiments of the invention with respect to the sensor may employ a "sticky" surface for the outer surface engaging a recipient's body (e.g. being formed from a low durometer silicone for example) so that the surface is designed to "stick", so it stays in place. This "sticky" surface may be smooth or textured for grip. Examples of materials may be those with durometer ideal Shore A10 or lower, Shore A5 or lower, or Shore A1. Within embodiments of the invention the footprint of the casing may be significantly larger than the shell (mechanical assembly) footprint, larger than the shell print, approximately the same as the shell footprint, and smaller than the shell footprint. Where the shell footprint is larger than the shell footprint its mechanical structure may be such that it does not droop under its weight/gravity when held free, droops a small amount, droops a moderate amount, or droops completely according to the desired characteristics. In embodiments of the invention the casing around the shell may act like a thin sheet (<<1 mm thick), like a fabric or material, like a sheet (~1 mm), a thick sheet (>1 mm).

Within embodiments of the invention the casing, for example formed from silicone, is the only material surrounding the casing and the surface profile is derived from applying the casing to the contoured surface of the shell. In other embodiments of the invention the surface profile is derived from multiple applications of a single material forming the casing. In other embodiments of the invention an additional material or materials are disposed between the shell and the casing. This, may for example, be a preform formed from the same material as the casing such that the casing is applied as a single or multiple dip coating for example, a preform formed from another silicone of different characteristics to the casing, a preform formed from a plastic, a preform formed from a low density foam, from a medium density foam, or a high density foam. Alternatively, a combination of materials may be employed such as two or more plastics, two or more foams, a foam and a plastic, a foam and a silicone, a form and metal. The materials may be layered, inserted, embedded, etc. without departing from the scope of the invention. However, a characteristic of these materials is the transmission of vibratory motion arising from the active elements within the sensor according to embodiments of the invention. Within passive embodiments this characteristic of material selection is removed.

Embodiments of the invention may exploit a single material for the outer casing or body, or they may employ multiple materials. Such materials may include a plastic, a thermoplastic, a polyester either discretely or in combination with one or more aramids. Optionally, an upper body portion may be jointed to a lower body portion by an elastomeric material or a silicone. Optionally, seals may employ a rubber, a synthetic rubber or an elastomeric material. Embodiments of the invention may exploit a scaffold only, a scaffold with a casing, a scaffold with a shell, and a scaffold with a casing and a shell.

Specific details are given in the above description to provide a thorough understanding of the embodiments. However, it is understood that the embodiments may be practiced without these specific details. For example, circuits may be shown in block diagrams in order not to obscure the embodiments in unnecessary detail. In other instances, well-known circuits, processes, algorithms, structures, and techniques may be shown without unnecessary detail in order to avoid obscuring the embodiments.

Implementation of the techniques, blocks, steps and means described above may be done in various ways. For example, these techniques, blocks, steps and means may be implemented in hardware, software, or a combination thereof. For a hardware implementation, the processing units may be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, other electronic units designed to perform the functions described above and/or a combination thereof.

Also, it is noted that the embodiments may be described as a process which is depicted as a flowchart, a flow diagram, a data flow diagram, a structure diagram, or a block diagram. Although a flowchart may describe the operations as a sequential process, many of the operations can be performed in parallel or concurrently. In addition, the order of the operations may be rearranged. A process is terminated when its operations are completed but could have additional steps not included in the figure. A process may correspond to a method, a function, a procedure, a subroutine, a subprogram, etc. When a process corresponds to a function, its termination corresponds to a return of the function to the calling function or the main function.

Furthermore, embodiments may be implemented by hardware, software, scripting languages, firmware, middleware, microcode, hardware description languages and/or any combination thereof. When implemented in software, firmware, middleware, scripting language and/or microcode, the program code or code segments to perform the necessary tasks may be stored in a machine readable medium, such as a storage medium. A code segment or machine-executable instruction may represent a procedure, a function, a subprogram, a program, a routine, a subroutine, a module, a software package, a script, a class, or any combination of instructions, data structures and/or program statements. A code segment may be coupled to another code segment or a hardware circuit by passing and/or receiving information, data, arguments, parameters and/or memory contents. Information, arguments, parameters, data, etc. may be passed, forwarded, or transmitted via any suitable means including memory sharing, message passing, token passing, network transmission, etc.

For a firmware and/or software implementation, the methodologies may be implemented with modules (e.g., procedures, functions, and so on) that perform the functions described herein. Any machine-readable medium tangibly embodying instructions may be used in implementing the methodologies described herein. For example, software codes may be stored in a memory. Memory may be implemented within the processor or external to the processor and may vary in implementation where the memory is employed in storing software codes for subsequent execution to that when the memory is employed in executing the software codes. As used herein the term "memory" refers to any type of long term, short term, volatile, nonvolatile, or other storage medium and is not to be limited to any particular type of memory or number of memories, or type of media upon which memory is stored.

Moreover, as disclosed herein, the term "storage medium" may represent one or more devices for storing data, including read only memory (ROM), random access memory (RAM), magnetic RAM, core memory, magnetic disk storage mediums, optical storage mediums, flash memory devices and/or other machine readable mediums for storing information. The term "machine-readable medium" includes but is not limited to portable or fixed storage devices, optical storage devices, wireless channels and/or various other mediums capable of storing, containing or carrying instruction(s) and/or data.

The methodologies described herein are, in one or more embodiments, performable by a machine which includes one or more processors that accept code segments containing instructions. For any of the methods described herein, when the instructions are executed by the machine, the machine performs the method. Any machine capable of executing a set of instructions (sequential or otherwise) that specify actions to be taken by that machine are included. Thus, a typical machine may be exemplified by a typical processing system that includes one or more processors. Each processor may include one or more of a CPU, a graphics-processing unit, and a programmable DSP unit. The processing system may further include a memory subsystem including main RAM and/or a static RAM, and/or ROM. A bus subsystem may be included for communicating between the components. If the processing system requires a display, such a display may be included, e.g., a liquid crystal display (LCD). If manual data entry is required, the processing system also includes an input device such as one or more of an alphanumeric input unit such as a keyboard, a pointing control device such as a mouse, and so forth.

The memory includes machine-readable code segments (e.g. software or software code) including instructions for performing, when executed by the processing system, one of more of the methods described herein. The software may reside entirely in the memory, or may also reside, completely or at least partially, within the RAM and/or within the processor during execution thereof by the computer system. Thus, the memory and the processor also constitute a system comprising machine-readable code.

In alternative embodiments, the machine operates as a standalone device or may be connected, e.g., networked to other machines, in a networked deployment, the machine may operate in the capacity of a server or a client machine in server-client network environment, or as a peer machine in a peer-to-peer or distributed network environment. The machine may be, for example, a computer, a server, a cluster of servers, a cluster of computers, a web appliance, a distributed computing environment, a cloud computing environment, or any machine capable of executing a set of instructions (sequential or otherwise) that specify actions to be taken by that machine. The term "machine" may also be taken to include any collection of machines that individually or jointly execute a set (or multiple sets) of instructions to perform any one or more of the methodologies discussed herein.

The foregoing disclosure of the exemplary embodiments of the present invention has been presented for purposes of illustration and description. It is not intended to be exhaustive or to limit the invention to the precise forms disclosed. Many variations and modifications of the embodiments described herein will be apparent to one of ordinary skill in the art in light of the above disclosure. The scope of the invention is to be defined only by the claims appended hereto, and by their equivalents.

Further, in describing representative embodiments of the present invention, the specification may have presented the method and/or process of the present invention as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process of the present invention should not be limited to the performance of their steps in the order written, and one skilled in the art can readily appreciate that the sequences may be varied and still remain within the spirit and scope of the present invention.

What is claimed is:

1. A sensor device comprising:
a body comprising an electronic circuit and either a wireless transmitter or a wireless transceiver operating according to a predetermined wireless standard;
a cable connecting one or more sensors externally disposed with respect to the body to the electronic circuit;
a strap attached at a first predetermined location on the body;
a hook disposed at a second predetermined location on the body; and
either:
a plurality of features upon at least one of an upper surface of the strap and a lower surface of the strap to enhance grip to a user manipulating the strap; or:
a plurality of features upon a lower surface of the strap proximal the end of the strap where it attaches to the body, the features for engaging a surface of an element the sensor device is to be attached to when the strap is wrapped around the element.

2. A sensor device comprising:
a body comprising an electronic circuit and either a wireless transmitter or a wireless transceiver operating according to a predetermined wireless standard;
one or more slots within a sidebar disposed on a first side of the body, each slot having a dimension to accept either an elastomeric strap or a retaining strap; wherein
a bottom surface of the body comprises:
a contoured portion dimensioned to engage one or more elements to which the sensor device is to be attached when the strap is wrapped around the element; and
a plurality of features disposed upon the contoured portion, the features for engaging a surface of an element the sensor device is to be attached to when the strap is wrapped around the element.

3. The sensor device according to claim 2, wherein
the element is a reinforcing bar; and
the surface of the reinforcing bar the plurality of features engage against are ribs of the reinforcing bar.

4. A sensor device comprising:
a body comprising an electronic circuit and either a wireless transmitter or a wireless transceiver operating according to a predetermined wireless standard;
an antenna disposed within the body supporting operation at microwave or radio frequency frequencies according to the predetermined wireless standard;
a first flex member attached at a first end of the body; and
a second flex member attached at a second end of the body; wherein
a bottom surface of the body comprises:
a contoured portion dimensioned to engage one or more elements to which the sensor device is to be attached when the strap is wrapped around the element; and
a plurality of features disposed upon the contoured portion, the features for engaging a surface of an element the sensor device is to be attached to when the strap is wrapped around the element.

5. A sensor device comprising:
a body comprising an electronic circuit and either a wireless transmitter or a wireless transceiver operating according to a predetermined wireless standard; wherein
the body forms a first portion of the sensor device and is formed from one or more resilient materials;
a second portion of the sensor device formed from an elastomeric material comprising a first region and a second region;
the second region of the sensor device is attached to the first portion of the sensor device such that the second region of the second portion of the sensor device is attached to a bottom surface of the first portion of the sensor device;
the first region of the second portion of the sensor device extends to one side of the body;
the first region provides a strap for attaching the body to a reinforcing bar;
the bottom surface of the first portion of the sensor device is contoured to surround a predetermined portion of the reinforcing bar; and
the second region of the second portion of the sensor device comprises a plurality of first features for engaging a surface of the reinforcing bar when the sensor device is attached to the reinforcing bar.

6. The sensor device according to claim 5, wherein
the sensor device is attached to the reinforcing bar by wrapping the first region of the second portion of the sensor device around the reinforcing bar and attaching it to a hook comprising part of the body of the sensing device.

7. The sensor device according to claim 5, wherein
a portion of the strap towards the first portion of the sensor device but not beneath the first portion of the sensor device comprises a plurality of second features for engaging the surface of the reinforcing bar when the sensor device is attached to the reinforcing bar.

8. A sensor device comprising:
a body comprising an electronic circuit and either a wireless transmitter or a wireless transceiver operating according to a predetermined wireless standard; wherein
a cable connecting one or more sensors externally disposed with respect to the body to the electronic circuit;
a first hook disposed at a first predetermined location on the body for attachment of a first portion of a strap;
a second hook disposed at a second predetermined location on the body for the attachment of a second portion of the strap; and
a sensor recess disposed within the body; wherein
when a housing disposed at an end of the cable distal to the body is disposed within the sensor recess the electronic circuit is in a first state; and
when a housing disposed at an end of the cable distal to the body is not disposed within the sensor recess the electronic circuit is in a second state.

9. The sensor device according to claim 8, wherein either:
the first state is powered off and the second state is powered on;
or:
the first state is a sleep state and the second state is an awake state.

10. The sensor device according to claim 8, wherein
the housing includes a magnet; and
the electronic circuit includes a magnetic proximity switch.

11. A sensor device comprising:
a body comprising an electronic circuit and either a wireless transmitter or a wireless transceiver operating according to a predetermined wireless standard;
a cable connecting one or more sensors externally disposed with respect to the body to the electronic circuit;
a strap attached at a first predetermined location on the body;
a hook disposed at a second predetermined location on the body; wherein
a bottom surface of the body comprises:
a contoured portion dimensioned to engage one or more elements to which the sensor device is to be attached when the strap is wrapped around the element; and
a plurality of features disposed upon the contoured portion, the features for engaging a surface of an element the sensor device is to be attached to when the strap is wrapped around the element.

12. The sensor device according to claim 11, wherein
the element is a reinforcing bar; and
the surface of the reinforcing bar the plurality of features engage against are ribs of the reinforcing bar.

* * * * *